(12) United States Patent
Mayse et al.

(10) Patent No.: US 10,149,714 B2
(45) Date of Patent: *Dec. 11, 2018

(54) SYSTEMS, ASSEMBLIES, AND METHODS FOR TREATING A BRONCHIAL TREE

(71) Applicant: Holaira, Inc., Plymouth, MN (US)

(72) Inventors: Martin L. Mayse, Wayzata, MN (US); Steven C. Dimmer, Bellevue, WA (US)

(73) Assignee: Nuvaira, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/427,685

(22) Filed: Feb. 8, 2017

(65) Prior Publication Data
US 2017/0143421 A1    May 25, 2017

Related U.S. Application Data

(63) Continuation of application No. 13/592,075, filed on Aug. 22, 2012, now Pat. No. 9,668,809, which is a
(Continued)

(51) Int. Cl.
*A61B 18/14* (2006.01)
*A61B 8/12* (2006.01)
(Continued)

(52) U.S. Cl.
CPC ............ *A61B 18/1477* (2013.01); *A61B 8/12* (2013.01); *A61B 18/1206* (2013.01);
(Continued)

(58) Field of Classification Search
CPC ............ A61B 18/1492; A61B 18/1485; A61B 2018/00577; A61B 2018/00017;
(Continued)

(56) References Cited

U.S. PATENT DOCUMENTS 612,724 A    10/1898  Hamilton
1,155,169 A   9/1915  John
(Continued)

FOREIGN PATENT DOCUMENTS

CA    2419228 A1    8/2004
CN    1700880 A    11/2005
(Continued)

OTHER PUBLICATIONS

Abbott., "Present Concepts Relative to Autonomic Nerve Surgery in the Treatment of Pulmonary Disease," American Journal of Surgery, 1955, vol. 90, pp. 479-489.
(Continued)

*Primary Examiner* — Thomas Giuliani
(74) *Attorney, Agent, or Firm* — Patterson Thuente Pedersen, P.A.

(57) ABSTRACT

Systems, assemblies, and methods to treat pulmonary diseases are used to decrease nervous system input to distal regions of the bronchial tree within the lungs. Treatment systems damage nerve tissue to temporarily or permanently decrease nervous system input. The treatment systems are capable of heating nerve tissue, cooling the nerve tissue, delivering a flowable substance that cause trauma to the nerve tissue, puncturing the nerve tissue, tearing the nerve tissue, cutting the nerve tissue, applying pressure to the nerve tissue, applying ultrasound to the nerve tissue, applying ionizing radiation to the nerve tissue, disrupting cell membranes of nerve tissue with electrical energy, or delivering long acting nerve blocking chemicals to the nerve tissue.

24 Claims, 21 Drawing Sheets

Related U.S. Application Data continuation of application No. 13/452,664, filed on Apr. 20, 2012, now Pat. No. 8,808,280, which is a continuation of application No. 13/245,522, filed on Sep. 26, 2011, now Pat. No. 8,226,638, which is a continuation of application No. 12/463,304, filed on May 8, 2009, now Pat. No. 8,088,127.

(60) Provisional application No. 61/155,449, filed on Feb. 25, 2009, provisional application No. 61/106,490, filed on Oct. 17, 2008, provisional application No. 61/052,082, filed on May 9, 2008.

(51) Int. Cl.

| | | |
|---|---|---|
| *A61B 18/12* | (2006.01) | |
| *A61B 18/18* | (2006.01) | |
| *A61B 18/24* | (2006.01) | |
| *A61B 34/20* | (2016.01) | |
| *A61B 18/02* | (2006.01) | |
| *A61B 17/00* | (2006.01) | |
| *A61B 18/00* | (2006.01) | |
| *A61N 7/02*  | (2006.01) | |

(52) U.S. Cl.
CPC ...... *A61B 18/1482* (2013.01); *A61B 18/1492* (2013.01); *A61B 18/18* (2013.01); *A61B 18/1815* (2013.01); *A61B 18/24* (2013.01); *A61B 34/20* (2016.02); *A61B 18/02* (2013.01); *A61B 2017/00022* (2013.01); *A61B 2018/00011* (2013.01); *A61B 2018/0022* (2013.01); *A61B 2018/00023* (2013.01); *A61B 2018/00214* (2013.01); *A61B 2018/00541* (2013.01); *A61B 2018/00577* (2013.01); *A61B 2018/0212* (2013.01); *A61B 2018/143* (2013.01); *A61B 2018/1432* (2013.01); *A61B 2018/1861* (2013.01); *A61N 7/022* (2013.01)

(58) Field of Classification Search
CPC .......... A61B 2018/00023; A61B 2018/00541; A61B 2018/0022; A61B 2018/00267; A61B 2018/00214; A61B 2018/00434; A61B 2018/0212; A61B 2018/0262; A61B 1/2676
USPC .............................................. 606/41, 46, 47
See application file for complete search history.

(56) References Cited

U.S. PATENT DOCUMENTS

| | | |
|---|---|---|
| 1,207,479 A | 12/1916 | Holger |
| 1,216,183 A | 2/1917 | Charles |
| 1,695,107 A | 12/1928 | Kahl |
| 2,072,346 A | 3/1937 | Smith |
| 2,279,714 A | 4/1942 | Meyerhof et al. |
| 3,320,957 A | 5/1967 | Sokolik |
| 3,568,659 A | 3/1971 | James |
| 3,667,476 A | 6/1972 | Henry |
| 3,692,029 A | 9/1972 | Edwin |
| 3,918,449 A | 11/1975 | Pistor |
| 3,946,745 A | 3/1976 | Hsiang-Lai et al. |
| 3,949,743 A | 4/1976 | Shanbrom |
| 3,995,617 A | 12/1976 | Watkins et al. |
| 4,078,864 A | 3/1978 | Howell |
| 4,095,602 A | 6/1978 | Leveen |
| 4,116,589 A | 9/1978 | Rishton |
| 4,129,129 A | 12/1978 | Amrine |
| 4,154,246 A | 5/1979 | Leveen |
| 4,277,168 A | 7/1981 | Oku |
| 4,305,402 A | 12/1981 | Katims |
| 4,351,330 A | 9/1982 | Scarberry |
| 4,461,283 A | 7/1984 | Doi |
| 4,502,490 A | 3/1985 | Evans et al. |
| 4,503,855 A | 3/1985 | Maslanka |
| 4,503,863 A | 3/1985 | Katims |
| 4,512,762 A | 4/1985 | Spears |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,573,481 A | 3/1986 | Bullara |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,643,186 A | 2/1987 | Rosen et al. |
| 4,646,737 A | 3/1987 | Hussein et al. |
| 4,649,924 A | 3/1987 | Taccardi |
| 4,649,935 A | 3/1987 | Charmillot et al. |
| 4,658,836 A | 4/1987 | Turner |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don et al. |
| 4,709,698 A | 12/1987 | Johnston et al. |
| 4,739,759 A | 4/1988 | Rexroth et al. |
| 4,754,065 A | 6/1988 | Levenson et al. |
| 4,754,752 A | 7/1988 | Ginsburg et al. |
| 4,765,322 A | 8/1988 | Charmillot et al. |
| 4,765,959 A | 8/1988 | Fukasawa |
| 4,767,402 A | 8/1988 | Kost et al. |
| 4,772,112 A | 9/1988 | Zider et al. |
| 4,773,899 A | 9/1988 | Spears |
| 4,779,614 A | 10/1988 | Moise |
| 4,784,135 A | 11/1988 | Blum et al. |
| 4,790,305 A | 12/1988 | Zoltan et al. |
| 4,799,479 A | 1/1989 | Spears |
| 4,802,492 A | 2/1989 | Grunstein |
| 4,808,164 A | 2/1989 | Hess |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,881,542 A | 11/1989 | Schmidt et al. |
| 4,895,557 A | 1/1990 | Moise et al. |
| 4,902,129 A | 2/1990 | Siegmund et al. |
| 4,904,472 A | 2/1990 | Belardinelli et al. |
| 4,906,229 A | 3/1990 | Wampler |
| 4,907,589 A | 3/1990 | Cosman |
| 4,908,012 A | 3/1990 | Moise et al. |
| 4,920,978 A | 5/1990 | Colvin |
| 4,944,722 A | 7/1990 | Carriker et al. |
| 4,945,910 A | 8/1990 | Budyko et al. |
| 4,955,377 A | 9/1990 | Lennox et al. |
| 4,967,765 A | 11/1990 | Turner et al. |
| 4,969,865 A | 11/1990 | Hwang et al. |
| 4,976,709 A | 12/1990 | Sand |
| 4,976,710 A | 12/1990 | Mackin |
| 4,985,014 A | 1/1991 | Orejola |
| 4,989,604 A | 2/1991 | Fang |
| 4,991,603 A | 2/1991 | Cohen et al. |
| 4,992,474 A | 2/1991 | Skidmore et al. |
| 5,005,559 A | 4/1991 | Blanco et al. |
| 5,007,908 A | 4/1991 | Rydell |
| 5,009,636 A | 4/1991 | Wortley et al. |
| 5,009,936 A | 4/1991 | Yamanaka et al. |
| 5,010,892 A | 4/1991 | Colvin et al. |
| 5,019,075 A | 5/1991 | Spears et al. |
| 5,027,829 A | 7/1991 | Larsen |
| 5,030,645 A | 7/1991 | Kollonitsch |
| 5,036,848 A | 8/1991 | Hewson |
| 5,053,033 A | 10/1991 | Clarke |
| 5,054,486 A | 10/1991 | Yamada |
| 5,056,519 A | 10/1991 | Vince |
| 5,056,529 A | 10/1991 | De Groot |
| 5,057,107 A | 10/1991 | Parins et al. |
| 5,074,860 A | 12/1991 | Gregory et al. |
| 5,078,716 A | 1/1992 | Doll |
| 5,084,044 A | 1/1992 | Quint |

(56) References Cited

U.S. PATENT DOCUMENTS

| | | |
|---|---|---|
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,106,360 A | 4/1992 | Ishiwara et al. |
| 5,107,830 A | 4/1992 | Younes |
| 5,107,835 A | 4/1992 | Thomas |
| 5,109,846 A | 5/1992 | Thomas |
| 5,114,423 A | 5/1992 | Kasprzyk et al. |
| 5,116,864 A | 5/1992 | March et al. |
| 5,117,828 A | 6/1992 | Metzger et al. |
| 5,123,413 A | 6/1992 | Hasegawa et al. |
| 5,126,375 A | 6/1992 | Skidmore et al. |
| 5,135,480 A | 8/1992 | Bannon et al. |
| 5,135,517 A | 8/1992 | McCoy |
| 5,139,029 A | 8/1992 | Fishman et al. |
| 5,151,100 A | 9/1992 | Abele et al. |
| 5,152,286 A | 10/1992 | Sitko et al. |
| 5,158,536 A | 10/1992 | Sekins et al. |
| 5,165,420 A | 11/1992 | Strickland |
| 5,167,223 A | 12/1992 | Koros et al. |
| 5,170,802 A | 12/1992 | Mehra |
| 5,170,803 A | 12/1992 | Hewson et al. |
| 5,174,288 A | 12/1992 | Bardy et al. |
| 5,188,602 A | 2/1993 | Nichols |
| 5,190,540 A | 3/1993 | Lee |
| 5,191,883 A | 3/1993 | Lennox et al. |
| 5,213,576 A | 5/1993 | Abiuso et al. |
| 5,215,103 A | 6/1993 | Desai |
| 5,224,491 A | 7/1993 | Mehra |
| 5,225,445 A | 7/1993 | Skidmore et al. |
| 5,231,996 A | 8/1993 | Bardy et al. |
| 5,232,444 A | 8/1993 | Just et al. |
| 5,234,456 A | 8/1993 | Silvestrini |
| 5,239,982 A | 8/1993 | Trauthen |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,271,383 A | 12/1993 | Wilk |
| 5,281,218 A | 1/1994 | Imran |
| 5,286,254 A | 2/1994 | Shapland et al. |
| 5,292,331 A | 3/1994 | Boneau |
| 5,293,869 A | 3/1994 | Edwards et al. |
| 5,309,910 A | 5/1994 | Edwards et al. |
| 5,311,866 A | 5/1994 | Kagan et al. |
| 5,313,943 A | 5/1994 | Houser et al. |
| 5,324,255 A | 6/1994 | Passafaro et al. |
| 5,324,284 A | 6/1994 | Imran |
| 5,331,947 A | 7/1994 | Shturman |
| 5,343,936 A | 9/1994 | Beatenbough et al. |
| 5,344,398 A | 9/1994 | Hara |
| 5,345,936 A | 9/1994 | Pomeranz et al. |
| 5,348,554 A | 9/1994 | Imran et al. |
| 5,366,443 A | 11/1994 | Eggers et al. |
| 5,368,591 A | 11/1994 | Lennox et al. |
| 5,370,644 A | 12/1994 | Langberg |
| 5,370,675 A | 12/1994 | Edwards et al. |
| 5,370,679 A | 12/1994 | Atlee, III |
| 5,372,603 A | 12/1994 | Acker et al. |
| 5,374,287 A | 12/1994 | Rubin |
| 5,379,765 A | 1/1995 | Kajiwara et al. |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,405,362 A | 4/1995 | Kramer et al. |
| 5,405,366 A | 4/1995 | Fox et al. |
| 5,409,483 A | 4/1995 | Campbell et al. |
| 5,409,710 A | 4/1995 | Leonard |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,422,362 A | 6/1995 | Vincent et al. |
| 5,423,744 A | 6/1995 | Gencheff et al. |
| 5,423,811 A | 6/1995 | Imran et al. |
| 5,425,023 A | 6/1995 | Haraguchi et al. |
| 5,425,703 A | 6/1995 | Feiring |
| 5,425,811 A | 6/1995 | Mashita |
| 5,431,696 A | 7/1995 | Atlee, III |
| 5,433,730 A | 7/1995 | Alt |
| 5,437,665 A | 8/1995 | Munro |
| 5,443,470 A | 8/1995 | Stern et al. |
| 5,454,782 A | 10/1995 | Perkins |
| 5,454,840 A | 10/1995 | Krakovsky et al. |
| 5,456,667 A | 10/1995 | Ham et al. |
| 5,458,596 A | 10/1995 | Lax et al. |
| 5,465,717 A | 11/1995 | Imran et al. |
| 5,470,352 A | 11/1995 | Rappaport |
| 5,471,982 A | 12/1995 | Edwards et al. |
| 5,474,530 A | 12/1995 | Passafaro et al. |
| 5,478,309 A | 12/1995 | Sweezer et al. |
| 5,478,578 A | 12/1995 | Arnold et al. |
| 5,496,271 A | 3/1996 | Burton et al. |
| 5,496,304 A | 3/1996 | Chasan |
| 5,496,311 A | 3/1996 | Abele et al. |
| 5,496,312 A | 3/1996 | Klicek |
| 5,500,011 A | 3/1996 | Desai |
| 5,505,728 A | 4/1996 | Ellman et al. |
| 5,505,730 A | 4/1996 | Edwards |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,540,730 A | 7/1996 | Terry, Jr. et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,553,611 A | 9/1996 | Budd et al. |
| 5,558,073 A | 9/1996 | Pomeranz et al. |
| 5,562,608 A | 10/1996 | Sekins et al. |
| 5,571,074 A | 11/1996 | Buckman, Jr. et al. |
| 5,571,088 A | 11/1996 | Lennox et al. |
| 5,574,059 A | 11/1996 | Regunathan et al. |
| 5,578,072 A | 11/1996 | Barone et al. |
| 5,582,609 A | 12/1996 | Swanson et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,620,463 A | 4/1997 | Drolet |
| 5,623,940 A | 4/1997 | Daikuzono |
| 5,624,392 A | 4/1997 | Saab |
| 5,624,439 A | 4/1997 | Edwards et al. |
| 5,626,618 A | 5/1997 | Ward et al. |
| 5,630,425 A | 5/1997 | Panescu et al. |
| 5,630,794 A | 5/1997 | Lax et al. |
| 5,630,813 A | 5/1997 | Kieturakis |
| 5,634,471 A | 6/1997 | Fairfax et al. |
| 5,641,326 A | 6/1997 | Adams |
| 5,647,870 A | 7/1997 | Kordis et al. |
| 5,658,278 A | 8/1997 | Imran et al. |
| 5,658,322 A | 8/1997 | Fleming |
| 5,658,549 A | 8/1997 | Akehurst et al. |
| 5,660,175 A | 8/1997 | Dayal |
| 5,662,108 A | 9/1997 | Budd et al. |
| 5,669,930 A | 9/1997 | Igarashi |
| 5,669,932 A | 9/1997 | Fischell et al. |

(56) References Cited

U.S. PATENT DOCUMENTS

| | | |
|---|---|---|
| 5,674,472 A | 10/1997 | Akehurst et al. |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,687,723 A | 11/1997 | Avitall |
| 5,688,267 A | 11/1997 | Panescu et al. |
| 5,690,692 A | 11/1997 | Fleming |
| 5,693,078 A | 12/1997 | Desai et al. |
| 5,694,934 A | 12/1997 | Edelman |
| 5,695,471 A | 12/1997 | Wampler |
| 5,699,799 A | 12/1997 | Xu et al. |
| 5,702,386 A | 12/1997 | Stern et al. |
| 5,707,218 A | 1/1998 | Maher et al. |
| 5,707,336 A | 1/1998 | Rubin |
| 5,707,352 A | 1/1998 | Sekins et al. |
| 5,707,400 A | 1/1998 | Terry, Jr. et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,727,569 A | 3/1998 | Benetti et al. |
| 5,728,094 A | 3/1998 | Edwards |
| 5,730,128 A | 3/1998 | Pomeranz et al. |
| 5,730,704 A | 3/1998 | Avitall |
| 5,730,726 A | 3/1998 | Klingenstein |
| 5,730,741 A | 3/1998 | Horzewski et al. |
| 5,733,316 A | 3/1998 | Tierney et al. |
| 5,733,319 A | 3/1998 | Neilson et al. |
| 5,735,846 A | 4/1998 | Panescu et al. |
| 5,740,808 A | 4/1998 | Panescu et al. |
| 5,741,248 A | 4/1998 | Stern et al. |
| 5,746,224 A | 5/1998 | Edwards |
| 5,752,518 A | 5/1998 | McGee et al. |
| 5,755,714 A | 5/1998 | Murphy-Chutorian |
| 5,755,753 A | 5/1998 | Knowlton |
| 5,759,158 A | 6/1998 | Swanson |
| 5,765,568 A | 6/1998 | Sweezer, Jr. |
| 5,766,605 A | 6/1998 | Sanders et al. |
| 5,769,846 A | 6/1998 | Edwards et al. |
| 5,772,590 A | 6/1998 | Webster, Jr. |
| 5,779,669 A | 7/1998 | Haissaguerre et al. |
| 5,779,698 A | 7/1998 | Clayman et al. |
| 5,782,239 A | 7/1998 | Webster, Jr. |
| 5,782,797 A | 7/1998 | Schweich, Jr. et al. |
| 5,782,827 A | 7/1998 | Gough et al. |
| 5,782,848 A | 7/1998 | Lennox |
| 5,782,899 A | 7/1998 | Imran |
| 5,792,064 A | 8/1998 | Panescu et al. |
| 5,795,303 A | 8/1998 | Swanson et al. |
| 5,800,375 A | 9/1998 | Sweezer et al. |
| 5,800,486 A | 9/1998 | Thome et al. |
| 5,807,306 A | 9/1998 | Shapland et al. |
| 5,810,757 A | 9/1998 | Sweezer, Jr. et al. |
| 5,810,807 A | 9/1998 | Ganz et al. |
| 5,814,078 A | 9/1998 | Zhou et al. |
| 5,817,028 A | 10/1998 | Anderson |
| 5,817,073 A | 10/1998 | Krespi |
| 5,820,554 A | 10/1998 | Davis et al. |
| 5,820,589 A | 10/1998 | Torgerson et al. |
| 5,823,189 A | 10/1998 | Kordis |
| 5,827,277 A | 10/1998 | Edwards |
| 5,833,651 A | 11/1998 | Donovan et al. |
| 5,836,874 A | 11/1998 | Swanson et al. |
| 5,836,905 A | 11/1998 | Lemelson et al. |
| 5,836,947 A | 11/1998 | Fleischman et al. |
| 5,837,001 A | 11/1998 | Mackey |
| 5,843,075 A | 12/1998 | Taylor |
| 5,843,077 A | 12/1998 | Edwards |
| 5,843,088 A | 12/1998 | Barra et al. |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. |
| 5,855,577 A | 1/1999 | Murphy-Chutorian et al. |
| 5,860,974 A * | 1/1999 | Abele ............... A61B 8/12 600/374 |
| 5,863,291 A | 1/1999 | Schaer |
| 5,865,791 A | 2/1999 | Whayne et al. |
| 5,868,740 A | 2/1999 | Leveen et al. |
| 5,871,443 A | 2/1999 | Edwards et al. |
| 5,871,483 A | 2/1999 | Jackson et al. |
| 5,871,523 A | 2/1999 | Fleischman et al. |
| 5,873,852 A | 2/1999 | Vigil et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,027 A | 4/1999 | Tu et al. |
| 5,891,135 A | 4/1999 | Jackson et al. |
| 5,891,136 A | 4/1999 | McGee et al. |
| 5,891,138 A | 4/1999 | Tu et al. |
| 5,891,182 A | 4/1999 | Fleming |
| 5,893,847 A | 4/1999 | Kordis |
| 5,893,887 A | 4/1999 | Jayaraman |
| 5,897,554 A | 4/1999 | Chia et al. |
| 5,899,882 A | 5/1999 | Waksman et al. |
| 5,902,268 A | 5/1999 | Saab |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,908,839 A | 6/1999 | Levitt et al. |
| 5,911,218 A | 6/1999 | DiMarco |
| 5,916,235 A | 6/1999 | Guglielmi |
| 5,919,147 A | 7/1999 | Jain |
| 5,919,172 A | 7/1999 | Golba, Jr. |
| 5,924,424 A | 7/1999 | Stevens et al. |
| 5,928,228 A | 7/1999 | Kordis et al. |
| 5,931,806 A | 8/1999 | Shimada |
| 5,931,835 A | 8/1999 | Mackey |
| 5,935,079 A | 8/1999 | Swanson et al. |
| 5,941,869 A | 8/1999 | Patterson et al. |
| 5,951,494 A | 9/1999 | Wang et al. |
| 5,951,546 A | 9/1999 | Lorentzen |
| 5,954,661 A | 9/1999 | Greenspon et al. |
| 5,954,662 A | 9/1999 | Swanson et al. |
| 5,954,717 A | 9/1999 | Behl et al. |
| 5,956,501 A | 9/1999 | Brown |
| 5,957,919 A | 9/1999 | Laufer |
| 5,957,961 A | 9/1999 | Maguire et al. |
| 5,964,223 A | 10/1999 | Baran |
| 5,964,753 A | 10/1999 | Edwards |
| 5,964,796 A | 10/1999 | Imran |
| 5,971,983 A | 10/1999 | Lesh |
| 5,972,026 A | 10/1999 | Laufer et al. |
| 5,976,175 A | 11/1999 | Hirano et al. |
| 5,976,709 A | 11/1999 | Kageyama et al. |
| 5,979,456 A | 11/1999 | Magovern |
| 5,980,563 A | 11/1999 | Tu et al. |
| 5,984,917 A | 11/1999 | Fleischman et al. |
| 5,984,971 A | 11/1999 | Faccioli et al. |
| 5,989,545 A | 11/1999 | Foster et al. |
| 5,991,650 A | 11/1999 | Swanson et al. |
| 5,992,419 A | 11/1999 | Sterzer et al. |
| 5,993,462 A | 11/1999 | Pomeranz et al. |
| 5,995,873 A | 11/1999 | Rhodes |
| 5,997,534 A | 12/1999 | Tu et al. |
| 5,999,855 A | 12/1999 | DiMarco |
| 6,001,054 A | 12/1999 | Regulla et al. |
| 6,003,517 A | 12/1999 | Sheffield et al. |
| 6,004,269 A | 12/1999 | Crowley et al. |
| 6,006,134 A | 12/1999 | Hill et al. |
| 6,006,755 A | 12/1999 | Edwards |
| 6,008,211 A | 12/1999 | Robinson et al. |
| 6,009,877 A | 1/2000 | Edwards |
| 6,010,500 A | 1/2000 | Sherman et al. |
| 6,012,457 A | 1/2000 | Lesh |
| 6,014,579 A | 1/2000 | Pomeranz et al. |
| 6,016,437 A | 1/2000 | Tu et al. |
| 6,023,638 A | 2/2000 | Swanson |
| 6,024,740 A | 2/2000 | Lesh et al. |

(56) References Cited

U.S. PATENT DOCUMENTS

| | | |
|---|---|---|
| 6,029,091 A | 2/2000 | De et al. |
| 6,033,397 A | 3/2000 | Laufer et al. |
| 6,036,687 A | 3/2000 | Laufer et al. |
| 6,036,689 A | 3/2000 | Tu et al. |
| 6,039,731 A | 3/2000 | Taylor et al. |
| 6,043,273 A | 3/2000 | Duhaylongsod |
| 6,045,549 A | 4/2000 | Smethers et al. |
| 6,045,550 A | 4/2000 | Simpson et al. |
| 6,050,992 A | 4/2000 | Nichols |
| 6,052,607 A | 4/2000 | Edwards et al. |
| 6,053,172 A | 4/2000 | Hovda et al. |
| 6,053,909 A | 4/2000 | Shadduck |
| 6,056,744 A | 5/2000 | Edwards |
| 6,056,745 A | 5/2000 | Panescu et al. |
| 6,056,769 A | 5/2000 | Epstein et al. |
| 6,060,454 A | 5/2000 | Duhaylongsod |
| 6,063,078 A | 5/2000 | Wittkampf |
| 6,063,768 A | 5/2000 | First |
| 6,071,280 A | 6/2000 | Edwards et al. |
| 6,071,281 A | 6/2000 | Burnside et al. |
| 6,071,282 A | 6/2000 | Fleischman |
| 6,081,749 A | 6/2000 | Ingle et al. |
| 6,083,249 A | 7/2000 | Familoni |
| 6,083,255 A | 7/2000 | Laufer et al. |
| 6,087,394 A | 7/2000 | Duhaylongsod |
| 6,090,104 A | 7/2000 | Webster, Jr. |
| 6,091,995 A | 7/2000 | Ingle et al. |
| 6,092,528 A | 7/2000 | Edwards |
| 6,097,985 A | 8/2000 | Kasevich et al. |
| 6,101,412 A | 8/2000 | Duhaylongsod |
| 6,102,886 A | 8/2000 | Lundquist et al. |
| 6,106,524 A | 8/2000 | Eggers et al. |
| 6,117,101 A | 9/2000 | Diederich et al. |
| 6,123,702 A | 9/2000 | Swanson et al. |
| 6,123,703 A | 9/2000 | Tu et al. |
| 6,123,718 A | 9/2000 | Tu et al. |
| 6,125,301 A | 9/2000 | Capel |
| 6,127,410 A | 10/2000 | Duhaylongsod |
| 6,129,726 A | 10/2000 | Edwards et al. |
| 6,135,997 A | 10/2000 | Laufer et al. |
| 6,139,527 A | 10/2000 | Laufer et al. |
| 6,139,571 A | 10/2000 | Fuller et al. |
| 6,139,845 A | 10/2000 | Donovan |
| 6,141,589 A | 10/2000 | Duhaylongsod |
| 6,142,993 A | 11/2000 | Whayne et al. |
| 6,143,013 A | 11/2000 | Samson et al. |
| 6,143,277 A | 11/2000 | Ashurst et al. |
| 6,149,647 A | 11/2000 | Tu et al. |
| 6,152,143 A | 11/2000 | Edwards |
| 6,152,899 A | 11/2000 | Farley et al. |
| 6,152,953 A | 11/2000 | Hipskind |
| 6,159,194 A | 12/2000 | Eggers et al. |
| 6,163,716 A | 12/2000 | Edwards et al. |
| 6,174,323 B1 | 1/2001 | Biggs et al. |
| 6,179,833 B1 | 1/2001 | Taylor |
| 6,183,468 B1 | 2/2001 | Swanson et al. |
| 6,197,013 B1 | 3/2001 | Reed et al. |
| 6,198,970 B1 | 3/2001 | Freed et al. |
| 6,200,311 B1 | 3/2001 | Danek et al. |
| 6,200,332 B1 | 3/2001 | Del |
| 6,200,333 B1 | 3/2001 | Laufer |
| 6,203,562 B1 | 3/2001 | Ohkubo |
| 6,210,013 B1 | 4/2001 | Bousfield |
| 6,210,355 B1 | 4/2001 | Edwards et al. |
| 6,210,367 B1 | 4/2001 | Carr |
| 6,212,432 B1 | 4/2001 | Matsuura |
| 6,212,433 B1 | 4/2001 | Behl |
| 6,214,002 B1 | 4/2001 | Fleischman et al. |
| 6,216,043 B1 | 4/2001 | Swanson et al. |
| 6,216,044 B1 | 4/2001 | Kordis |
| 6,216,704 B1 | 4/2001 | Ingle et al. |
| 6,217,576 B1 | 4/2001 | Tu et al. |
| 6,226,543 B1 | 5/2001 | Gilboa et al. |
| 6,230,052 B1 | 5/2001 | Wolff et al. |
| 6,231,595 B1 | 5/2001 | Dobak, III |
| 6,235,024 B1 | 5/2001 | Tu |
| 6,238,392 B1 | 5/2001 | Long |
| 6,240,307 B1 | 5/2001 | Beatty et al. |
| 6,241,727 B1 | 6/2001 | Tu et al. |
| 6,245,040 B1 | 6/2001 | Inderbitzen et al. |
| 6,245,065 B1 | 6/2001 | Panescu et al. |
| 6,251,368 B1 | 6/2001 | Akehurst et al. |
| 6,253,762 B1 | 7/2001 | Britto |
| 6,254,598 B1 | 7/2001 | Edwards et al. |
| 6,254,599 B1 | 7/2001 | Lesh et al. |
| 6,258,083 B1 | 7/2001 | Daniel et al. |
| 6,258,087 B1 | 7/2001 | Edwards et al. |
| 6,264,653 B1 | 7/2001 | Falwell |
| 6,265,379 B1 | 7/2001 | Donovan |
| 6,269,813 B1 | 8/2001 | Fitzgerald et al. |
| 6,270,476 B1 | 8/2001 | Santoianni et al. |
| 6,273,886 B1 | 8/2001 | Edwards et al. |
| 6,273,907 B1 | 8/2001 | Laufer |
| 6,283,987 B1 | 9/2001 | Laird et al. |
| 6,283,988 B1 | 9/2001 | Laufer et al. |
| 6,283,989 B1 | 9/2001 | Laufer et al. |
| 6,287,304 B1 | 9/2001 | Eggers et al. |
| 6,296,639 B1 | 10/2001 | Truckai et al. |
| 6,299,633 B1 | 10/2001 | Laufer |
| 6,302,870 B1 | 10/2001 | Jacobsen et al. |
| 6,303,509 B1 | 10/2001 | Chen et al. |
| 6,306,423 B1 | 10/2001 | Donovan et al. |
| 6,315,173 B1 | 11/2001 | Di et al. |
| 6,315,778 B1 | 11/2001 | Gambale et al. |
| 6,317,615 B1 | 11/2001 | Kenknight et al. |
| 6,322,559 B1 | 11/2001 | Daulton et al. |
| 6,322,584 B2 | 11/2001 | Ingle et al. |
| 6,325,798 B1 | 12/2001 | Edwards et al. |
| 6,327,503 B1 | 12/2001 | Familoni |
| 6,338,727 B1 | 1/2002 | Noda et al. |
| 6,338,836 B1 | 1/2002 | Kuth et al. |
| 6,341,236 B1 | 1/2002 | Osorio et al. |
| 6,346,104 B2 | 2/2002 | Daly et al. |
| 6,355,031 B1 | 3/2002 | Edwards et al. |
| 6,356,786 B1 | 3/2002 | Rezai et al. |
| 6,356,787 B1 | 3/2002 | Rezai et al. |
| 6,357,447 B1 | 3/2002 | Swanson et al. |
| 6,358,245 B1 | 3/2002 | Edwards et al. |
| 6,358,926 B2 | 3/2002 | Donovan |
| 6,361,554 B1 | 3/2002 | Brisken |
| 6,363,937 B1 | 4/2002 | Hovda et al. |
| 6,366,814 B1 | 4/2002 | Boveja et al. |
| 6,379,352 B1 | 4/2002 | Reynolds et al. |
| 6,383,509 B1 | 5/2002 | Donovan et al. |
| 6,394,956 B1 | 5/2002 | Chandrasekaran et al. |
| 6,402,744 B2 | 6/2002 | Edwards et al. |
| 6,405,732 B1 | 6/2002 | Edwards et al. |
| 6,409,723 B1 | 6/2002 | Edwards |
| 6,411,852 B1 | 6/2002 | Danek et al. |
| 6,414,018 B1 | 7/2002 | Duhaylongsod |
| 6,416,511 B1 | 7/2002 | Lesh et al. |
| 6,416,740 B1 | 7/2002 | Unger |
| 6,423,058 B1 | 7/2002 | Edwards et al. |
| 6,423,105 B1 | 7/2002 | Iijima et al. |
| 6,424,864 B1 | 7/2002 | Matsuura |
| 6,425,877 B1 | 7/2002 | Edwards |
| 6,425,887 B1 | 7/2002 | McGuckin et al. |
| 6,425,895 B1 | 7/2002 | Swanson et al. |
| 6,432,092 B2 | 8/2002 | Miller |
| 6,436,130 B1 | 8/2002 | Philips et al. |
| 6,438,423 B1 | 8/2002 | Rezai et al. |
| 6,440,128 B1 | 8/2002 | Edwards et al. |
| 6,440,129 B1 | 8/2002 | Simpson |
| 6,442,435 B2 | 8/2002 | King et al. |
| 6,447,505 B2 | 9/2002 | McGovern et al. |
| 6,447,785 B1 | 9/2002 | Donovan |
| 6,448,231 B2 | 9/2002 | Graham |
| 6,451,013 B1 | 9/2002 | Bays et al. |
| 6,458,121 B1 | 10/2002 | Rosenstock et al. |
| 6,460,545 B2 | 10/2002 | Kordis |
| 6,464,680 B1 | 10/2002 | Brisken et al. |
| 6,464,697 B1 | 10/2002 | Edwards et al. |
| 6,475,160 B1 | 11/2002 | Sher |
| 6,480,746 B1 | 11/2002 | Ingle et al. |

(56) References Cited

U.S. PATENT DOCUMENTS

| | | |
|---|---|---|
| 6,485,416 B1 | 11/2002 | Platt et al. |
| 6,488,673 B1 * | 12/2002 | Laufer .................. A61B 18/00 604/516 |
| 6,488,679 B1 | 12/2002 | Swanson et al. |
| 6,491,710 B2 | 12/2002 | Satake |
| 6,493,589 B1 | 12/2002 | Medhkour et al. |
| 6,494,880 B1 | 12/2002 | Swanson et al. |
| 6,496,737 B2 | 12/2002 | Rudie et al. |
| 6,496,738 B2 | 12/2002 | Carr |
| 6,506,399 B2 | 1/2003 | Donovan |
| 6,510,969 B2 | 1/2003 | Di et al. |
| 6,514,246 B1 | 2/2003 | Swanson et al. |
| 6,514,290 B1 | 2/2003 | Loomas |
| 6,519,488 B2 | 2/2003 | Kenknight et al. |
| 6,522,913 B2 | 2/2003 | Swanson et al. |
| 6,524,555 B1 | 2/2003 | Ashurst et al. |
| 6,526,320 B2 | 2/2003 | Mitchell |
| 6,526,976 B1 | 3/2003 | Baran |
| 6,529,756 B1 | 3/2003 | Phan et al. |
| 6,532,388 B1 | 3/2003 | Hill et al. |
| 6,533,780 B1 | 3/2003 | Laird et al. |
| 6,536,427 B2 | 3/2003 | Davies et al. |
| 6,544,226 B1 | 4/2003 | Gaiser et al. |
| 6,544,262 B2 | 4/2003 | Fleischman |
| 6,546,928 B1 | 4/2003 | Ashurst et al. |
| 6,546,932 B1 | 4/2003 | Nahon et al. |
| 6,546,934 B1 | 4/2003 | Ingle et al. |
| 6,547,776 B1 | 4/2003 | Gaiser et al. |
| 6,547,788 B1 | 4/2003 | Maguire et al. |
| 6,549,808 B1 | 4/2003 | Gisel et al. |
| 6,551,274 B2 | 4/2003 | Heiner |
| 6,551,310 B1 | 4/2003 | Ganz et al. |
| 6,558,333 B2 | 5/2003 | Gilboa et al. |
| 6,558,378 B2 | 5/2003 | Sherman et al. |
| 6,558,381 B2 | 5/2003 | Ingle et al. |
| 6,562,034 B2 | 5/2003 | Edwards et al. |
| 6,572,612 B2 | 6/2003 | Stewart et al. |
| 6,575,623 B2 | 6/2003 | Werneth |
| 6,575,969 B1 | 6/2003 | Rittman, III et al. |
| 6,582,427 B1 | 6/2003 | Goble et al. |
| 6,582,430 B2 | 6/2003 | Hall |
| 6,587,718 B2 | 7/2003 | Talpade |
| 6,587,719 B1 | 7/2003 | Barrett et al. |
| 6,587,731 B1 | 7/2003 | Ingle et al. |
| 6,589,235 B2 | 7/2003 | Wong et al. |
| 6,589,238 B2 | 7/2003 | Edwards et al. |
| 6,593,130 B1 | 7/2003 | Sen et al. |
| 6,599,311 B1 | 7/2003 | Biggs et al. |
| 6,601,581 B1 | 8/2003 | Babaev |
| 6,603,996 B1 | 8/2003 | Beatty et al. |
| 6,610,054 B1 | 8/2003 | Edwards et al. |
| 6,610,083 B2 | 8/2003 | Keller et al. |
| 6,610,713 B2 | 8/2003 | Tracey |
| 6,613,002 B1 | 9/2003 | Clark et al. |
| 6,613,045 B1 | 9/2003 | Laufer et al. |
| 6,620,159 B2 | 9/2003 | Hegde |
| 6,620,415 B2 | 9/2003 | Donovan |
| 6,622,047 B2 | 9/2003 | Barrett et al. |
| 6,623,742 B2 | 9/2003 | Voet |
| 6,626,855 B1 | 9/2003 | Weng et al. |
| 6,626,903 B2 | 9/2003 | McGuckin et al. |
| 6,629,535 B2 | 10/2003 | Ingle et al. |
| 6,629,951 B2 | 10/2003 | Laufer et al. |
| 6,632,440 B1 | 10/2003 | Quinn et al. |
| 6,633,779 B1 | 10/2003 | Schuler et al. |
| 6,634,363 B1 | 10/2003 | Danek et al. |
| 6,635,054 B2 | 10/2003 | Fjield et al. |
| 6,635,056 B2 | 10/2003 | Kadhiresan et al. |
| 6,638,273 B1 | 10/2003 | Farley et al. |
| 6,640,119 B1 | 10/2003 | Budd et al. |
| 6,640,120 B1 | 10/2003 | Swanson et al. |
| 6,645,200 B1 | 11/2003 | Koblish et al. |
| 6,645,496 B2 | 11/2003 | Aoki et al. |
| 6,647,617 B1 | 11/2003 | Beatty et al. |
| 6,648,881 B2 | 11/2003 | Kenknight et al. |
| 6,649,161 B1 | 11/2003 | Donovan |
| 6,652,517 B1 | 11/2003 | Hall et al. |
| 6,652,548 B2 | 11/2003 | Evans et al. |
| 6,656,960 B2 | 12/2003 | Puskas |
| 6,658,279 B2 | 12/2003 | Swanson et al. |
| 6,663,622 B1 | 12/2003 | Foley et al. |
| 6,666,858 B2 | 12/2003 | Lafontaine |
| 6,669,693 B2 | 12/2003 | Friedman |
| 6,671,533 B2 | 12/2003 | Chen et al. |
| 6,673,068 B1 | 1/2004 | Berube |
| 6,673,070 B2 | 1/2004 | Edwards et al. |
| 6,675,047 B1 | 1/2004 | Konoplev et al. |
| 6,676,686 B2 | 1/2004 | Naganuma |
| 6,681,136 B2 | 1/2004 | Schuler et al. |
| 6,692,492 B2 | 2/2004 | Simpson et al. |
| 6,692,494 B1 | 2/2004 | Cooper et al. |
| 6,699,180 B2 | 3/2004 | Kobayashi |
| 6,699,243 B2 | 3/2004 | West et al. |
| 6,708,064 B2 | 3/2004 | Rezai |
| 6,711,436 B1 | 3/2004 | Duhaylongsod |
| 6,712,074 B2 | 3/2004 | Edwards et al. |
| 6,712,812 B2 | 3/2004 | Roschak et al. |
| 6,712,814 B2 | 3/2004 | Edwards et al. |
| 6,714,822 B2 | 3/2004 | King et al. |
| 6,719,685 B2 | 4/2004 | Fujikura et al. |
| 6,719,694 B2 | 4/2004 | Weng et al. |
| 6,723,053 B2 | 4/2004 | Ackerman et al. |
| 6,723,091 B2 | 4/2004 | Goble et al. |
| 6,728,562 B1 | 4/2004 | Budd et al. |
| 6,735,471 B2 | 5/2004 | Hill et al. |
| 6,735,475 B1 | 5/2004 | Whitehurst et al. |
| 6,740,321 B1 | 5/2004 | Donovan |
| 6,743,197 B1 | 6/2004 | Edwards |
| 6,743,413 B1 | 6/2004 | Schultz et al. |
| 6,749,604 B1 | 6/2004 | Eggers et al. |
| 6,749,606 B2 | 6/2004 | Keast et al. |
| 6,752,765 B1 | 6/2004 | Jensen et al. |
| 6,755,026 B2 | 6/2004 | Wallach |
| 6,755,849 B1 | 6/2004 | Gowda et al. |
| 6,767,347 B2 | 7/2004 | Sharkey et al. |
| 6,767,544 B2 | 7/2004 | Brooks et al. |
| 6,770,070 B1 | 8/2004 | Balbierz |
| 6,772,013 B1 | 8/2004 | Frank et al. |
| 6,773,711 B2 | 8/2004 | Voet et al. |
| 6,776,991 B2 | 8/2004 | Naumann |
| 6,777,423 B2 | 8/2004 | Banholzer et al. |
| 6,778,854 B2 | 8/2004 | Puskas |
| 6,780,183 B2 | 8/2004 | Jimenez et al. |
| 6,786,889 B1 | 9/2004 | Musbach et al. |
| 6,802,843 B2 | 10/2004 | Truckai et al. |
| 6,805,131 B2 | 10/2004 | Kordis |
| 6,819,956 B2 | 11/2004 | DiLorenzo |
| 6,826,420 B1 | 11/2004 | Beatty et al. |
| 6,826,421 B1 | 11/2004 | Beatty et al. |
| 6,827,931 B1 | 12/2004 | Donovan |
| 6,836,688 B2 | 12/2004 | Ingle et al. |
| 6,837,888 B2 | 1/2005 | Ciarrocca et al. |
| 6,838,429 B2 | 1/2005 | Paslin |
| 6,838,434 B2 | 1/2005 | Voet |
| 6,838,471 B2 | 1/2005 | Tracey |
| 6,840,243 B2 | 1/2005 | Deem et al. |
| 6,841,156 B2 | 1/2005 | Aoki et al. |
| 6,843,998 B1 | 1/2005 | Steward et al. |
| 6,846,312 B2 | 1/2005 | Edwards et al. |
| 6,847,849 B2 | 1/2005 | Mamo et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,861,058 B2 | 3/2005 | Aoki et al. |
| 6,866,662 B2 | 3/2005 | Fuimaono et al. |
| 6,871,092 B2 | 3/2005 | Piccone |
| 6,872,206 B2 | 3/2005 | Edwards et al. |
| 6,872,397 B2 | 3/2005 | Aoki et al. |
| 6,878,156 B1 | 4/2005 | Noda |
| 6,881,213 B2 | 4/2005 | Ryan et al. |
| 6,885,888 B2 | 4/2005 | Rezai |
| 6,890,347 B2 | 5/2005 | Machold et al. |
| 6,893,436 B2 | 5/2005 | Woodard et al. |
| 6,893,438 B2 | 5/2005 | Hall et al. |

(56) References Cited

U.S. PATENT DOCUMENTS

| | | |
|---|---|---|
| 6,893,439 B2 | 5/2005 | Fleischman |
| 6,895,267 B2 | 5/2005 | Panescu et al. |
| 6,904,303 B2 | 6/2005 | Phan et al. |
| 6,908,462 B2 | 6/2005 | Joye et al. |
| 6,908,928 B2 | 6/2005 | Banholzer et al. |
| 6,913,616 B2 | 7/2005 | Hamilton et al. |
| 6,917,834 B2 | 7/2005 | Koblish et al. |
| 6,934,583 B2 | 8/2005 | Weinberg et al. |
| 6,937,896 B1 | 8/2005 | Kroll |
| 6,937,903 B2 | 8/2005 | Schuler et al. |
| 6,939,309 B1 | 9/2005 | Beatty et al. |
| 6,939,345 B2 | 9/2005 | Kenknight et al. |
| 6,939,346 B2 | 9/2005 | Kannenberg et al. |
| 6,947,785 B1 | 9/2005 | Beatty et al. |
| 6,954,977 B2 | 10/2005 | Maguire et al. |
| 6,957,106 B2 | 10/2005 | Schuler et al. |
| 6,961,622 B2 | 11/2005 | Gilbert |
| 6,970,742 B2 | 11/2005 | Mann et al. |
| RE38,912 E | 12/2005 | Walz et al. |
| 6,971,395 B2 | 12/2005 | Edwards et al. |
| 6,974,224 B2 | 12/2005 | Thomas-Benedict |
| 6,974,456 B2 | 12/2005 | Edwards et al. |
| 6,974,578 B1 | 12/2005 | Aoki et al. |
| 6,978,168 B2 | 12/2005 | Beatty et al. |
| 6,978,174 B2 | 12/2005 | Gelfand et al. |
| 6,990,370 B1 | 1/2006 | Beatty et al. |
| 6,994,706 B2 | 2/2006 | Chornenky et al. |
| 6,997,189 B2 | 2/2006 | Biggs et al. |
| 7,004,942 B2 | 2/2006 | Laird et al. |
| 7,022,088 B2 | 4/2006 | Keast et al. |
| 7,022,105 B1 | 4/2006 | Edwards |
| 7,027,869 B2 | 4/2006 | Danek et al. |
| 7,043,307 B1 | 5/2006 | Zelickson et al. |
| 7,070,800 B2 | 7/2006 | Bechtold-Peters et al. |
| 7,072,720 B2 | 7/2006 | Puskas |
| 7,083,614 B2 | 8/2006 | Fjield et al. |
| 7,101,368 B2 | 9/2006 | Lafontaine |
| 7,101,387 B2 | 9/2006 | Garabedian et al. |
| 7,104,987 B2 | 9/2006 | Biggs et al. |
| 7,104,990 B2 | 9/2006 | Jenkins et al. |
| 7,112,198 B2 | 9/2006 | Satake |
| 7,118,568 B2 | 10/2006 | Hassett et al. |
| 7,122,031 B2 | 10/2006 | Edwards et al. |
| 7,122,033 B2 | 10/2006 | Wood |
| 7,125,407 B2 | 10/2006 | Edwards et al. |
| 7,131,445 B2 | 11/2006 | Amoah |
| 7,142,910 B2 | 11/2006 | Puskas |
| 7,150,745 B2 | 12/2006 | Stern et al. |
| 7,162,303 B2 | 1/2007 | Levin et al. |
| 7,165,551 B2 | 1/2007 | Edwards et al. |
| 7,167,757 B2 | 1/2007 | Ingle et al. |
| 7,175,644 B2 | 2/2007 | Cooper et al. |
| 7,179,257 B2 | 2/2007 | West et al. |
| 7,186,251 B2 | 3/2007 | Malecki et al. |
| 7,187,964 B2 | 3/2007 | Khoury |
| 7,187,973 B2 | 3/2007 | Hauck |
| 7,189,208 B1 | 3/2007 | Beatty et al. |
| 7,198,635 B2 | 4/2007 | Danek et al. |
| 7,200,445 B1 | 4/2007 | Dalbec et al. |
| 7,229,469 B1 | 6/2007 | Witzel et al. |
| 7,238,357 B2 | 7/2007 | Barron |
| 7,241,295 B2 | 7/2007 | Maguire |
| 7,255,693 B1 | 8/2007 | Johnston et al. |
| RE39,820 E | 9/2007 | Banholzer et al. |
| 7,264,002 B2 | 9/2007 | Danek et al. |
| 7,266,414 B2 | 9/2007 | Cornelius et al. |
| 7,273,055 B2 | 9/2007 | Danek et al. |
| 7,289,843 B2 | 10/2007 | Beatty et al. |
| 7,291,146 B2 | 11/2007 | Steinke et al. |
| 7,292,890 B2 | 11/2007 | Whitehurst et al. |
| 7,309,707 B2 | 12/2007 | Bender et al. |
| 7,310,552 B2 | 12/2007 | Puskas |
| RE40,045 E | 2/2008 | Palmer |
| 7,326,207 B2 | 2/2008 | Edwards |
| 7,344,535 B2 | 3/2008 | Stern et al. |
| 7,371,231 B2 | 5/2008 | Rioux et al. |
| 7,393,330 B2 | 7/2008 | Keast et al. |
| 7,393,350 B2 | 7/2008 | Maurice |
| 7,394,976 B2 | 7/2008 | Entenman et al. |
| 7,402,172 B2 | 7/2008 | Chin et al. |
| 7,422,563 B2 | 9/2008 | Roschak et al. |
| 7,422,584 B2 | 9/2008 | Loomas et al. |
| 7,425,212 B1 | 9/2008 | Danek et al. |
| 7,430,449 B2 | 9/2008 | Aldrich et al. |
| 7,462,162 B2 | 12/2008 | Phan et al. |
| 7,462,179 B2 | 12/2008 | Edwards et al. |
| 7,473,273 B2 | 1/2009 | Campbell |
| 7,477,945 B2 | 1/2009 | Rezai et al. |
| 7,483,755 B2 | 1/2009 | Ingle et al. |
| 7,493,160 B2 | 2/2009 | Weber et al. |
| 7,494,661 B2 | 2/2009 | Sanders |
| 7,507,234 B2 | 3/2009 | Utley et al. |
| 7,507,238 B2 | 3/2009 | Utley et al. |
| 7,517,320 B2 | 4/2009 | Wibowo et al. |
| 7,530,979 B2 | 5/2009 | Ganz et al. |
| 7,532,938 B2 | 5/2009 | Machado et al. |
| 7,542,802 B2 | 6/2009 | Danek et al. |
| 7,553,307 B2 | 6/2009 | Bleich et al. |
| 7,556,624 B2 | 7/2009 | Laufer et al. |
| 7,559,890 B2 | 7/2009 | Wallace et al. |
| 7,572,245 B2 | 8/2009 | Herweck et al. |
| 7,585,296 B2 | 9/2009 | Edward et al. |
| 7,588,549 B2 | 9/2009 | Eccleston |
| 7,594,925 B2 | 9/2009 | Danek et al. |
| 7,608,275 B2 | 10/2009 | Deem et al. |
| 7,613,515 B2 | 11/2009 | Knudson et al. |
| 7,617,005 B2 | 11/2009 | Demarais et al. |
| 7,620,451 B2 | 11/2009 | Demarais et al. |
| 7,628,789 B2 | 12/2009 | Soltesz et al. |
| 7,632,268 B2 | 12/2009 | Utley et al. |
| 7,641,632 B2 | 1/2010 | Noda et al. |
| 7,641,633 B2 | 1/2010 | Laufer et al. |
| 7,648,500 B2 | 1/2010 | Edwards et al. |
| 7,653,438 B2 | 1/2010 | Deem et al. |
| 7,684,865 B2 | 3/2010 | Aldrich et al. |
| 7,689,290 B2 | 3/2010 | Ingle et al. |
| 7,691,079 B2 | 4/2010 | Gobel et al. |
| RE41,334 E | 5/2010 | Beatty et al. |
| 7,708,712 B2 | 5/2010 | Phan et al. |
| 7,708,768 B2 | 5/2010 | Danek et al. |
| 7,711,430 B2 | 5/2010 | Errico et al. |
| 7,717,948 B2 | 5/2010 | Demarais et al. |
| 7,722,538 B2 | 5/2010 | Khoury |
| 7,725,188 B2 | 5/2010 | Errico et al. |
| 7,734,355 B2 | 6/2010 | Cohen et al. |
| 7,734,535 B1 | 6/2010 | Burns |
| 7,740,017 B2 | 6/2010 | Danek et al. |
| 7,740,631 B2 | 6/2010 | Bleich et al. |
| 7,742,795 B2 | 6/2010 | Stone et al. |
| 7,747,324 B2 | 6/2010 | Errico et al. |
| 7,756,583 B2 | 7/2010 | Demarais et al. |
| 7,765,010 B2 | 7/2010 | Chornenky et al. |
| 7,770,584 B2 | 8/2010 | Danek et al. |
| 7,783,358 B2 | 8/2010 | Aldrich et al. |
| 7,815,590 B2 | 10/2010 | Cooper |
| 7,826,881 B1 | 11/2010 | Beatty et al. |
| 7,831,288 B1 | 11/2010 | Beatty et al. |
| 7,837,676 B2 | 11/2010 | Sinelnikov et al. |
| 7,837,679 B2 | 11/2010 | Biggs et al. |
| 7,841,986 B2 | 11/2010 | He et al. |
| 7,844,338 B2 | 11/2010 | Knudson et al. |
| 7,853,331 B2 | 12/2010 | Kaplan et al. |
| 7,854,734 B2 | 12/2010 | Biggs et al. |
| 7,854,740 B2 | 12/2010 | Carney et al. |
| 7,869,879 B2 | 1/2011 | Errico et al. |
| 7,869,880 B2 | 1/2011 | Errico et al. |
| 7,873,417 B2 | 1/2011 | Demarais et al. |
| 7,877,146 B2 | 1/2011 | Rezai et al. |
| 7,904,159 B2 | 3/2011 | Errico et al. |
| 7,906,124 B2 | 3/2011 | Laufer et al. |
| 7,914,448 B2 | 3/2011 | Bob et al. |
| 7,921,855 B2 | 4/2011 | Danek et al. |
| 7,930,012 B2 | 4/2011 | Beatty et al. |
| 7,931,647 B2 | 4/2011 | Wizeman et al. |

(56) References Cited

U.S. PATENT DOCUMENTS

| | | | |
|---|---|---|---|
| 7,937,143 B2 | 5/2011 | Demarais et al. |
| 7,938,123 B2 | 5/2011 | Danek et al. |
| 7,949,407 B2 | 5/2011 | Kaplan et al. |
| 7,967,782 B2 | 6/2011 | Laufer et al. |
| 7,985,187 B2 | 7/2011 | Wibowo et al. |
| 7,992,572 B2 | 8/2011 | Danek et al. |
| 7,993,336 B2 | 8/2011 | Jackson et al. |
| 8,002,740 B2 | 8/2011 | Willink et al. |
| 8,007,495 B2 | 8/2011 | McDaniel et al. |
| 8,010,197 B2 | 8/2011 | Errico et al. |
| 8,012,149 B2 | 9/2011 | Jackson et al. |
| 8,041,428 B2 | 10/2011 | Errico et al. |
| 8,046,085 B2 | 10/2011 | Knudson et al. |
| 8,052,668 B2 | 11/2011 | Sih |
| 8,088,127 B2 | 1/2012 | Mayse et al. |
| 8,099,167 B1 | 1/2012 | Errico et al. |
| 8,105,817 B2 | 1/2012 | Deem et al. |
| 8,128,595 B2 | 3/2012 | Walker et al. |
| 8,128,617 B2 | 3/2012 | Bencini et al. |
| 8,131,371 B2 | 3/2012 | Demarals et al. |
| 8,133,497 B2 | 3/2012 | Deem et al. |
| 8,152,803 B2 | 4/2012 | Edwards et al. |
| 8,172,827 B2 | 5/2012 | Deem et al. |
| 8,204,598 B2 | 6/2012 | Errico et al. |
| 8,208,998 B2 | 6/2012 | Beatty et al. |
| 8,209,034 B2 | 6/2012 | Simon et al. |
| 8,216,216 B2 | 7/2012 | Warnking et al. |
| 8,226,638 B2 | 7/2012 | Mayse et al. |
| 8,229,564 B2 | 7/2012 | Rezai |
| 8,231,621 B2 | 7/2012 | Hutchins et al. |
| 8,233,988 B2 | 7/2012 | Errico et al. |
| 8,251,992 B2 | 8/2012 | Utley et al. |
| 8,267,094 B2 | 9/2012 | Danek et al. |
| 8,295,902 B2 | 10/2012 | Salahieh et al. |
| 8,303,581 B2 | 11/2012 | Arts et al. |
| 8,313,484 B2 | 11/2012 | Edwards et al. |
| 8,328,798 B2 | 12/2012 | Witzel et al. |
| 8,338,164 B2 | 12/2012 | Deem et al. |
| 8,347,891 B2 | 1/2013 | Demarais et al. |
| 8,357,118 B2 | 1/2013 | Orr |
| 8,364,237 B2 | 1/2013 | Stone et al. |
| 8,371,303 B2 | 2/2013 | Schaner et al. |
| 8,377,055 B2 | 2/2013 | Jackson et al. |
| 8,454,594 B2 | 6/2013 | Demarais et al. |
| 8,483,831 B1 | 7/2013 | Hlavka et al. |
| 8,489,192 B1 | 7/2013 | Hlavka et al. |
| 8,660,647 B2 | 2/2014 | Parnis et al. |
| 8,731,672 B2 | 5/2014 | Hlavka et al. |
| 8,740,895 B2 | 6/2014 | Mayse et al. |
| 8,777,943 B2 * | 7/2014 | Mayse | A61B 18/1492 606/41 |
| 8,808,280 B2 | 8/2014 | Mayse et al. |
| 8,821,489 B2 | 9/2014 | Mayse et al. |
| 8,911,439 B2 | 12/2014 | Mayse et al. |
| 8,932,289 B2 | 1/2015 | Mayse et al. |
| 8,961,391 B2 | 2/2015 | Deem et al. |
| 8,961,507 B2 | 2/2015 | Mayse et al. |
| 8,961,508 B2 | 2/2015 | Mayse et al. |
| 9,005,195 B2 * | 4/2015 | Mayse | A61B 18/1492 606/41 |
| 9,017,324 B2 * | 4/2015 | Mayse | A61B 18/1492 606/41 |
| 9,125,643 B2 | 9/2015 | Hlavka et al. |
| 9,149,328 B2 | 10/2015 | Dimmer et al. |
| 9,339,618 B2 | 5/2016 | Deem et al. |
| 9,398,933 B2 | 7/2016 | Mayse et al. |
| 9,498,283 B2 | 11/2016 | Deem et al. |
| 9,539,048 B2 | 1/2017 | Hlavka et al. |
| 9,649,153 B2 | 5/2017 | Mayse et al. |
| 9,649,154 B2 | 5/2017 | Mayse et al. |
| 9,662,171 B2 * | 5/2017 | Dimmer | A61B 18/1492 |
| 9,668,809 B2 * | 6/2017 | Mayse | A61B 18/1477 |
| 9,675,412 B2 * | 6/2017 | Mayse | A61B 18/1492 |
| 9,867,986 B2 | 1/2018 | Hlavka et al. |
| 2001/0020151 A1 | 9/2001 | Reed et al. |
| 2001/0044596 A1 | 11/2001 | Jaafar |
| 2002/0002387 A1 | 1/2002 | Naganuma |
| 2002/0010495 A1 | 1/2002 | Freed et al. |
| 2002/0013581 A1 | 1/2002 | Edwards et al. |
| 2002/0016344 A1 | 2/2002 | Tracey |
| 2002/0042564 A1 | 4/2002 | Cooper et al. |
| 2002/0042565 A1 | 4/2002 | Cooper et al. |
| 2002/0049370 A1 | 4/2002 | Laufer et al. |
| 2002/0072738 A1 | 6/2002 | Edwards et al. |
| 2002/0082197 A1 | 6/2002 | Aoki et al. |
| 2002/0087153 A1 | 7/2002 | Roschak et al. |
| 2002/0087208 A1 * | 7/2002 | Koblish | A61B 18/1492 607/113 |
| 2002/0091379 A1 | 7/2002 | Danek et al. |
| 2002/0107512 A1 | 8/2002 | Edwards |
| 2002/0107515 A1 | 8/2002 | Edwards et al. |
| 2002/0111386 A1 | 8/2002 | Sekins et al. |
| 2002/0111619 A1 | 8/2002 | Keast et al. |
| 2002/0111620 A1 | 8/2002 | Cooper et al. |
| 2002/0115991 A1 | 8/2002 | Edwards |
| 2002/0116030 A1 | 8/2002 | Rezai |
| 2002/0143302 A1 | 10/2002 | Hinchliffe et al. |
| 2002/0143326 A1 | 10/2002 | Foley et al. |
| 2002/0143373 A1 | 10/2002 | Courtnage et al. |
| 2002/0151888 A1 | 10/2002 | Edwards et al. |
| 2002/0183682 A1 | 12/2002 | Darvish |
| 2002/0198512 A1 | 12/2002 | Seward |
| 2002/0198570 A1 | 12/2002 | Puskas |
| 2002/0198574 A1 | 12/2002 | Gumpert |
| 2003/0018344 A1 | 1/2003 | Kaji et al. |
| 2003/0023287 A1 | 1/2003 | Edwards et al. |
| 2003/0027752 A1 | 2/2003 | Steward et al. |
| 2003/0050591 A1 | 3/2003 | Patrick |
| 2003/0050631 A1 | 3/2003 | Mody et al. |
| 2003/0065371 A1 | 4/2003 | Satake |
| 2003/0069570 A1 | 4/2003 | Witzel et al. |
| 2003/0070676 A1 | 4/2003 | Cooper et al. |
| 2003/0074039 A1 | 4/2003 | Puskas |
| 2003/0093069 A1 | 5/2003 | Panescu et al. |
| 2003/0093128 A1 | 5/2003 | Freed et al. |
| 2003/0100895 A1 | 5/2003 | Simpson et al. |
| 2003/0125786 A1 | 7/2003 | Gliner et al. |
| 2003/0130657 A1 | 7/2003 | Tom et al. |
| 2003/0144572 A1 | 7/2003 | Oschman et al. |
| 2003/0153905 A1 | 8/2003 | Edwards et al. |
| 2003/0159700 A1 | 8/2003 | Laufer et al. |
| 2003/0181949 A1 | 9/2003 | Whale |
| 2003/0187430 A1 | 10/2003 | Vorisek |
| 2003/0195593 A1 | 10/2003 | Ingle et al. |
| 2003/0195604 A1 | 10/2003 | Ingle et al. |
| 2003/0202990 A1 | 10/2003 | Donovan et al. |
| 2003/0208103 A1 | 11/2003 | Sonnenschein et al. |
| 2003/0211121 A1 | 11/2003 | Donovan |
| 2003/0216791 A1 | 11/2003 | Schuler et al. |
| 2003/0216792 A1 | 11/2003 | Levin et al. |
| 2003/0216891 A1 | 11/2003 | Wegener |
| 2003/0225443 A1 | 12/2003 | Kiran et al. |
| 2003/0233099 A1 | 12/2003 | Danaek et al. |
| 2003/0236455 A1 | 12/2003 | Swanson et al. |
| 2004/0006268 A1 | 1/2004 | Gilboa et al. |
| 2004/0009180 A1 | 1/2004 | Donovan |
| 2004/0010289 A1 | 1/2004 | Biggs et al. |
| 2004/0010290 A1 | 1/2004 | Schroeppel et al. |
| 2004/0028676 A1 | 2/2004 | Klein et al. |
| 2004/0029849 A1 | 2/2004 | Schatzberg et al. |
| 2004/0030368 A1 | 2/2004 | Kemeny et al. |
| 2004/0031494 A1 | 2/2004 | Danek et al. |
| 2004/0044390 A1 | 3/2004 | Szeles |
| 2004/0059383 A1 | 3/2004 | Puskas |
| 2004/0073201 A1 | 4/2004 | Cooper et al. |
| 2004/0073206 A1 | 4/2004 | Foley et al. |
| 2004/0073278 A1 | 4/2004 | Pachys |
| 2004/0082948 A1 | 4/2004 | Stewart et al. |
| 2004/0086531 A1 | 5/2004 | Barron |
| 2004/0087936 A1 | 5/2004 | Stern et al. |
| 2004/0088030 A1 | 5/2004 | Jung et al. |
| 2004/0088036 A1 | 5/2004 | Gilbert |
| 2004/0091880 A1 | 5/2004 | Wiebusch et al. |
| 2004/0106954 A1 | 6/2004 | Whitehurst et al. |

(56) References Cited

U.S. PATENT DOCUMENTS

| | | |
|---|---|---|
| 2004/0116981 A1 | 6/2004 | Mazar |
| 2004/0122488 A1 | 6/2004 | Mazar et al. |
| 2004/0122489 A1 | 6/2004 | Mazar et al. |
| 2004/0127942 A1 | 7/2004 | Yomtov et al. |
| 2004/0127958 A1 | 7/2004 | Mazar et al. |
| 2004/0142005 A1 | 7/2004 | Brooks et al. |
| 2004/0147921 A1 | 7/2004 | Edwards et al. |
| 2004/0147969 A1 | 7/2004 | Mann et al. |
| 2004/0147988 A1 | 7/2004 | Stephens |
| 2004/0151741 A1 | 8/2004 | Borodic |
| 2004/0153056 A1 | 8/2004 | Muller et al. |
| 2004/0158237 A1 | 8/2004 | Abboud et al. |
| 2004/0162584 A1 | 8/2004 | Hill et al. |
| 2004/0162597 A1 | 8/2004 | Hamilton et al. |
| 2004/0167509 A1 | 8/2004 | Taimisto |
| 2004/0167580 A1 | 8/2004 | Mann et al. |
| 2004/0172075 A1 | 9/2004 | Shafer et al. |
| 2004/0172080 A1 | 9/2004 | Stadler et al. |
| 2004/0172084 A1 | 9/2004 | Knudson et al. |
| 2004/0175399 A1 | 9/2004 | Schiffman |
| 2004/0176803 A1 | 9/2004 | Whelan et al. |
| 2004/0176805 A1 | 9/2004 | Whelan et al. |
| 2004/0182399 A1 | 9/2004 | Danek et al. |
| 2004/0186435 A1 | 9/2004 | Seward |
| 2004/0204747 A1 | 10/2004 | Kemeny et al. |
| 2004/0213813 A1 | 10/2004 | Ackerman |
| 2004/0213814 A1 | 10/2004 | Ackerman |
| 2004/0215235 A1 | 10/2004 | Jackson et al. |
| 2004/0215289 A1 | 10/2004 | Fukui |
| 2004/0215296 A1 | 10/2004 | Ganz et al. |
| 2004/0220556 A1 | 11/2004 | Cooper et al. |
| 2004/0220621 A1 | 11/2004 | Zhou et al. |
| 2004/0226556 A1 | 11/2004 | Deem et al. |
| 2004/0230251 A1 | 11/2004 | Schuler et al. |
| 2004/0230252 A1 | 11/2004 | Kullok et al. |
| 2004/0243118 A1 | 12/2004 | Ayers et al. |
| 2004/0243182 A1 | 12/2004 | Cohen et al. |
| 2004/0248188 A1 | 12/2004 | Sanders |
| 2004/0249401 A1 | 12/2004 | Rabiner et al. |
| 2004/0249416 A1 | 12/2004 | Yun et al. |
| 2004/0253274 A1 | 12/2004 | Voet |
| 2005/0004609 A1 | 1/2005 | Stahmann et al. |
| 2005/0004631 A1 | 1/2005 | Benedict |
| 2005/0010263 A1 | 1/2005 | Schauerte |
| 2005/0010270 A1 | 1/2005 | Laufer |
| 2005/0015117 A1 | 1/2005 | Gerber |
| 2005/0019346 A1 | 1/2005 | Boulis |
| 2005/0021092 A1 | 1/2005 | Yun et al. |
| 2005/0049615 A1 | 3/2005 | Cooper et al. |
| 2005/0055020 A1 | 3/2005 | Skarda |
| 2005/0056292 A1 | 3/2005 | Cooper |
| 2005/0059153 A1 | 3/2005 | George et al. |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0065553 A1 | 3/2005 | Ben et al. |
| 2005/0065562 A1 | 3/2005 | Rezai et al. |
| 2005/0065567 A1 | 3/2005 | Lee et al. |
| 2005/0065573 A1 | 3/2005 | Rezai |
| 2005/0065574 A1 | 3/2005 | Rezai |
| 2005/0065575 A1 | 3/2005 | Dobak |
| 2005/0065584 A1 | 3/2005 | Schiff et al. |
| 2005/0074461 A1 | 4/2005 | Donovan |
| 2005/0076909 A1 | 4/2005 | Stahmann et al. |
| 2005/0080461 A1 | 4/2005 | Stahmann et al. |
| 2005/0085801 A1 | 4/2005 | Cooper et al. |
| 2005/0090722 A1 | 4/2005 | Perez |
| 2005/0096529 A1 | 5/2005 | Cooper et al. |
| 2005/0096644 A1 | 5/2005 | Hall et al. |
| 2005/0107783 A1 | 5/2005 | Tom et al. |
| 2005/0107829 A1 | 5/2005 | Edwards et al. |
| 2005/0107853 A1 | 5/2005 | Krespi et al. |
| 2005/0125044 A1 | 6/2005 | Tracey et al. |
| 2005/0137518 A1 | 6/2005 | Biggs et al. |
| 2005/0137611 A1 | 6/2005 | Escudero et al. |
| 2005/0137715 A1 | 6/2005 | Phan et al. |
| 2005/0143788 A1 | 6/2005 | Yun et al. |
| 2005/0149146 A1 | 7/2005 | Boveja et al. |
| 2005/0152924 A1 | 7/2005 | Voet |
| 2005/0153885 A1 | 7/2005 | Yun et al. |
| 2005/0159736 A9 | 7/2005 | Danek et al. |
| 2005/0165456 A1 | 7/2005 | Mann et al. |
| 2005/0171396 A1 | 8/2005 | Pankratov et al. |
| 2005/0177144 A1 | 8/2005 | Phan et al. |
| 2005/0177192 A1 | 8/2005 | Rezai et al. |
| 2005/0182288 A1 | 8/2005 | Zabara |
| 2005/0182393 A1 | 8/2005 | Abboud et al. |
| 2005/0183732 A1 | 8/2005 | Edwards |
| 2005/0187579 A1 | 8/2005 | Danek et al. |
| 2005/0193279 A1 | 9/2005 | Daners |
| 2005/0203503 A1 | 9/2005 | Edwards et al. |
| 2005/0222628 A1 | 10/2005 | Krakousky |
| 2005/0222635 A1 | 10/2005 | Krakovsky |
| 2005/0222651 A1 | 10/2005 | Jung |
| 2005/0228054 A1 | 10/2005 | Tatton |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0238693 A1 | 10/2005 | Whyte |
| 2005/0240176 A1 | 10/2005 | Oral et al. |
| 2005/0240241 A1 | 10/2005 | Yun et al. |
| 2005/0245926 A1 | 11/2005 | Edwards et al. |
| 2005/0245992 A1 | 11/2005 | Persen et al. |
| 2005/0251128 A1 | 11/2005 | Amoah |
| 2005/0251213 A1 | 11/2005 | Freeman |
| 2005/0255317 A1 | 11/2005 | Bavaro et al. |
| 2005/0256028 A1 | 11/2005 | Yun et al. |
| 2005/0261747 A1 | 11/2005 | Schuler et al. |
| 2005/0267536 A1 | 12/2005 | Freeman et al. |
| 2005/0277993 A1 | 12/2005 | Mower |
| 2005/0283197 A1 | 12/2005 | Daum et al. |
| 2006/0009758 A1 | 1/2006 | Edwards et al. |
| 2006/0015151 A1 | 1/2006 | Aldrich |
| 2006/0058692 A1 | 3/2006 | Beatty et al. |
| 2006/0058693 A1 | 3/2006 | Beatty et al. |
| 2006/0058780 A1 | 3/2006 | Edwards et al. |
| 2006/0062808 A1 | 3/2006 | Laufer et al. |
| 2006/0079887 A1 | 4/2006 | Buysse et al. |
| 2006/0084884 A1 | 4/2006 | Beatty et al. |
| 2006/0084966 A1 | 4/2006 | Maguire et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0089637 A1 | 4/2006 | Werneth et al. |
| 2006/0095029 A1 | 5/2006 | Young et al. |
| 2006/0095032 A1 | 5/2006 | Jackson et al. |
| 2006/0100666 A1 | 5/2006 | Wilkinson et al. |
| 2006/0106361 A1 | 5/2006 | Muni et al. |
| 2006/0111755 A1 | 5/2006 | Stone et al. |
| 2006/0116749 A1 | 6/2006 | Willink et al. |
| 2006/0118127 A1 | 6/2006 | Chinn |
| 2006/0135953 A1 | 6/2006 | Kania et al. |
| 2006/0135984 A1 | 6/2006 | Kramer et al. |
| 2006/0135998 A1 | 6/2006 | Libbus et al. |
| 2006/0137698 A1 | 6/2006 | Danek et al. |
| 2006/0142801 A1 | 6/2006 | Demarais et al. |
| 2006/0167498 A1 | 7/2006 | DiLorenzo |
| 2006/0178703 A1 | 8/2006 | Huston et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0222667 A1 | 10/2006 | Deem et al. |
| 2006/0225742 A1 | 10/2006 | Deem et al. |
| 2006/0235474 A1 | 10/2006 | Demarais |
| 2006/0241523 A1 | 10/2006 | Sinelnikov et al. |
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0247683 A1 | 11/2006 | Danek et al. |
| 2006/0247726 A1 | 11/2006 | Biggs et al. |
| 2006/0247727 A1 | 11/2006 | Biggs et al. |
| 2006/0247746 A1 | 11/2006 | Danek et al. |
| 2006/0254600 A1 | 11/2006 | Danek et al. |
| 2006/0259028 A1 | 11/2006 | Utley et al. |

(56) References Cited

U.S. PATENT DOCUMENTS

| | | |
|---|---|---|
| 2006/0259029 A1 | 11/2006 | Utley et al. |
| 2006/0259030 A1 | 11/2006 | Utley et al. |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276807 A1 | 12/2006 | Keast et al. |
| 2006/0276852 A1 | 12/2006 | Demarais et al. |
| 2006/0278243 A1 | 12/2006 | Danek et al. |
| 2006/0278244 A1 | 12/2006 | Danek et al. |
| 2006/0280772 A1 | 12/2006 | Roschak et al. |
| 2006/0280773 A1 | 12/2006 | Roschak et al. |
| 2006/0282071 A1 | 12/2006 | Utley et al. |
| 2006/0287679 A1 | 12/2006 | Stone |
| 2007/0021803 A1 | 1/2007 | Deem et al. |
| 2007/0025919 A1 | 2/2007 | Deem et al. |
| 2007/0027496 A1 | 2/2007 | Parnis et al. |
| 2007/0032788 A1 | 2/2007 | Edwards et al. |
| 2007/0043342 A1 | 2/2007 | Kleinberger |
| 2007/0043350 A1 | 2/2007 | Soltesz et al. |
| 2007/0055328 A1 | 3/2007 | Mayse et al. |
| 2007/0060954 A1 | 3/2007 | Cameron et al. |
| 2007/0060990 A1 | 3/2007 | Satake |
| 2007/0062545 A1 | 3/2007 | Danek et al. |
| 2007/0066957 A1 | 3/2007 | Demarais et al. |
| 2007/0074719 A1 | 4/2007 | Danek et al. |
| 2007/0083194 A1 | 4/2007 | Kunis et al. |
| 2007/0083197 A1 | 4/2007 | Danek et al. |
| 2007/0083239 A1 | 4/2007 | Demarais et al. |
| 2007/0093802 A1 | 4/2007 | Danek et al. |
| 2007/0093809 A1 | 4/2007 | Edwards et al. |
| 2007/0100390 A1 | 5/2007 | Danaek et al. |
| 2007/0102011 A1 | 5/2007 | Danek et al. |
| 2007/0106292 A1 | 5/2007 | Kaplan et al. |
| 2007/0106296 A1 | 5/2007 | Laufer et al. |
| 2007/0106337 A1 | 5/2007 | Errico et al. |
| 2007/0106338 A1 | 5/2007 | Errico |
| 2007/0106339 A1 | 5/2007 | Errico et al. |
| 2007/0106348 A1 | 5/2007 | Laufer |
| 2007/0112349 A1 | 5/2007 | Danek et al. |
| 2007/0118184 A1 | 5/2007 | Danek et al. |
| 2007/0118190 A1 | 5/2007 | Danek et al. |
| 2007/0123922 A1 | 5/2007 | Cooper et al. |
| 2007/0123958 A1 | 5/2007 | Laufer |
| 2007/0123961 A1 | 5/2007 | Danek et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0156185 A1 | 7/2007 | Swanson et al. |
| 2007/0173899 A1 | 7/2007 | Levin et al. |
| 2007/0191902 A1 | 8/2007 | Errico et al. |
| 2007/0197896 A1 | 8/2007 | Moll et al. |
| 2007/0203549 A1 | 8/2007 | Demarais et al. |
| 2007/0225768 A1 | 9/2007 | Dobak, III |
| 2007/0232896 A1 | 10/2007 | Gilboa et al. |
| 2007/0239256 A1 | 10/2007 | Weber et al. |
| 2007/0244479 A1 | 10/2007 | Beatty et al. |
| 2007/0250050 A1 | 10/2007 | Lafontaine |
| 2007/0255270 A1 | 11/2007 | Carney |
| 2007/0255304 A1 | 11/2007 | Roschak et al. |
| 2007/0265639 A1 | 11/2007 | Danek et al. |
| 2007/0265687 A1 | 11/2007 | Deem et al. |
| 2007/0267011 A1 | 11/2007 | Deem et al. |
| 2007/0270794 A1 | 11/2007 | Anderson et al. |
| 2008/0004596 A1 | 1/2008 | Yun et al. |
| 2008/0021274 A1 | 1/2008 | Bayer et al. |
| 2008/0021369 A1 | 1/2008 | Deem et al. |
| 2008/0051839 A1 | 2/2008 | Libbus et al. |
| 2008/0086107 A1 | 4/2008 | Roschak |
| 2008/0097422 A1 | 4/2008 | Edwards et al. |
| 2008/0097424 A1 | 4/2008 | Wizeman et al. |
| 2008/0125772 A1 | 5/2008 | Stone et al. |
| 2008/0147137 A1 | 6/2008 | Cohen et al. |
| 2008/0154258 A1 | 6/2008 | Chang et al. |
| 2008/0161801 A1 | 7/2008 | Steinke et al. |
| 2008/0183248 A1 | 7/2008 | Rezai et al. |
| 2008/0188912 A1 | 8/2008 | Stone et al. |
| 2008/0188913 A1 | 8/2008 | Stone et al. |
| 2008/0194956 A1 | 8/2008 | Aldrich et al. |
| 2008/0208305 A1 | 8/2008 | Rezai et al. |
| 2008/0213331 A1 | 9/2008 | Gelfand et al. |
| 2008/0234564 A1 | 9/2008 | Beatty et al. |
| 2008/0243112 A1 | 10/2008 | De |
| 2008/0255449 A1 | 10/2008 | Warnking et al. |
| 2008/0255642 A1 | 10/2008 | Zarins et al. |
| 2008/0262489 A1 | 10/2008 | Steinke |
| 2008/0275445 A1 | 11/2008 | Kelly et al. |
| 2008/0302359 A1 | 12/2008 | Loomas et al. |
| 2008/0306570 A1 | 12/2008 | Rezai et al. |
| 2008/0312543 A1 | 12/2008 | Laufer et al. |
| 2008/0312725 A1 | 12/2008 | Penner |
| 2008/0319350 A1 | 12/2008 | Wallace et al. |
| 2009/0018473 A1 | 1/2009 | Aldrich et al. |
| 2009/0018538 A1 | 1/2009 | Webster et al. |
| 2009/0022197 A1 | 1/2009 | Hisa et al. |
| 2009/0030477 A1 | 1/2009 | Jarrard |
| 2009/0036948 A1 | 2/2009 | Levin et al. |
| 2009/0043301 A1* | 2/2009 | Jarrard ............... A61B 18/1492 606/41 |
| 2009/0043302 A1 | 2/2009 | Ford et al. |
| 2009/0048593 A1 | 2/2009 | Ganz et al. |
| 2009/0060953 A1 | 3/2009 | Sandars |
| 2009/0062873 A1 | 3/2009 | Wu et al. |
| 2009/0069797 A1 | 3/2009 | Danek et al. |
| 2009/0076409 A1 | 3/2009 | Wu et al. |
| 2009/0076491 A1 | 3/2009 | Roschak et al. |
| 2009/0112203 A1 | 4/2009 | Danek et al. |
| 2009/0124883 A1 | 5/2009 | Wibowo et al. |
| 2009/0131765 A1 | 5/2009 | Roschak et al. |
| 2009/0131928 A1 | 5/2009 | Edwards et al. |
| 2009/0131930 A1 | 5/2009 | Gelbart et al. |
| 2009/0143678 A1 | 6/2009 | Keast et al. |
| 2009/0143705 A1 | 6/2009 | Danek et al. |
| 2009/0143776 A1 | 6/2009 | Danek et al. |
| 2009/0143831 A1 | 6/2009 | Huston et al. |
| 2009/0155336 A1 | 6/2009 | Rezai |
| 2009/0177192 A1 | 7/2009 | Rioux et al. |
| 2009/0192505 A1 | 7/2009 | Askew et al. |
| 2009/0192508 A1 | 7/2009 | Laufer et al. |
| 2009/0204005 A1 | 8/2009 | Keast et al. |
| 2009/0204119 A1 | 8/2009 | Bleich et al. |
| 2009/0221997 A1 | 9/2009 | Arnold et al. |
| 2009/0227885 A1 | 9/2009 | Lowery et al. |
| 2009/0227980 A1 | 9/2009 | Kangas et al. |
| 2009/0232850 A1 | 9/2009 | Manack et al. |
| 2009/0248011 A1 | 10/2009 | Hlavka et al. |
| 2009/0254079 A1 | 10/2009 | Edwards et al. |
| 2009/0254142 A1 | 10/2009 | Edwards et al. |
| 2009/0259274 A1 | 10/2009 | Simon et al. |
| 2009/0275840 A1 | 11/2009 | Roschak et al. |
| 2009/0275878 A1 | 11/2009 | Cambier et al. |
| 2009/0281593 A9 | 11/2009 | Errico et al. |
| 2009/0287087 A1 | 11/2009 | Gwerder et al. |
| 2009/0306644 A1 | 12/2009 | Mayse et al. |
| 2009/0318904 A9 | 12/2009 | Cooper et al. |
| 2009/0319002 A1 | 12/2009 | Simon et al. |
| 2010/0003282 A1 | 1/2010 | Deem et al. |
| 2010/0004648 A1 | 1/2010 | Edwards et al. |
| 2010/0010564 A1 | 1/2010 | Simon et al. |
| 2010/0016709 A1 | 1/2010 | Gilboa et al. |
| 2010/0042089 A1 | 2/2010 | Soltesz et al. |
| 2010/0049031 A1 | 2/2010 | Fruland et al. |
| 2010/0049186 A1 | 2/2010 | Ingle et al. |
| 2010/0049188 A1 | 2/2010 | Nelson et al. |
| 2010/0057178 A1 | 3/2010 | Simon |
| 2010/0063495 A1 | 3/2010 | Edwards et al. |
| 2010/0070004 A1 | 3/2010 | Hlavka et al. |
| 2010/0076518 A1 | 3/2010 | Hlavka et al. |
| 2010/0087783 A1 | 4/2010 | Weber et al. |
| 2010/0087809 A1 | 4/2010 | Edwards et al. |
| 2010/0094231 A1 | 4/2010 | Bleich et al. |
| 2010/0114087 A1 | 5/2010 | Edwards et al. |
| 2010/0116279 A9 | 5/2010 | Cooper |
| 2010/0125239 A1 | 5/2010 | Perry et al. |

(56) References Cited

U.S. PATENT DOCUMENTS

| | | |
|---|---|---|
| 2010/0130892 A1 | 5/2010 | Warnking |
| 2010/0137860 A1 | 6/2010 | Demarais et al. |
| 2010/0145427 A1 | 6/2010 | Gliner et al. |
| 2010/0152835 A1 | 6/2010 | Orr |
| 2010/0160906 A1 | 6/2010 | Jarrard |
| 2010/0160996 A1 | 6/2010 | Simon et al. |
| 2010/0174340 A1 | 7/2010 | Simon |
| 2010/0179424 A1 | 7/2010 | Warnking et al. |
| 2010/0185190 A1 | 7/2010 | Danek et al. |
| 2010/0191089 A1 | 7/2010 | Stebler et al. |
| 2010/0204689 A1 | 8/2010 | Danek et al. |
| 2010/0222851 A1 | 9/2010 | Deem et al. |
| 2010/0228318 A1 | 9/2010 | Errico et al. |
| 2010/0241188 A1 | 9/2010 | Errico et al. |
| 2010/0249873 A1 | 9/2010 | Errico |
| 2010/0256629 A1 | 10/2010 | Wylie et al. |
| 2010/0256630 A1 | 10/2010 | Hamilton, Jr. et al. |
| 2010/0268222 A1 | 10/2010 | Danek et al. |
| 2010/0298905 A1 | 11/2010 | Simon |
| 2010/0305463 A1 | 12/2010 | Macklem et al. |
| 2010/0318020 A1 | 12/2010 | Atanasoska et al. |
| 2010/0331776 A1 | 12/2010 | Salahieh et al. |
| 2011/0004148 A1 | 1/2011 | Ishii |
| 2011/0015548 A1 | 1/2011 | Aldrich et al. |
| 2011/0028898 A1 | 2/2011 | Clark, III et al. |
| 2011/0046432 A1 | 2/2011 | Simon et al. |
| 2011/0060380 A1 | 3/2011 | Gelfand et al. |
| 2011/0079230 A1 | 4/2011 | Danek et al. |
| 2011/0093032 A1 | 4/2011 | Boggs, II et al. |
| 2011/0098762 A1 | 4/2011 | Rezai |
| 2011/0112400 A1 | 5/2011 | Emery et al. |
| 2011/0112521 A1 | 5/2011 | Delonzor et al. |
| 2011/0118725 A1 | 5/2011 | Mayse et al. |
| 2011/0125203 A1 | 5/2011 | Simon et al. |
| 2011/0125213 A1 | 5/2011 | Simon et al. |
| 2011/0130708 A1 | 6/2011 | Perry et al. |
| 2011/0137284 A1 | 6/2011 | Arora et al. |
| 2011/0144630 A1 | 6/2011 | Loeb |
| 2011/0146673 A1 | 6/2011 | Keast et al. |
| 2011/0146674 A1 | 6/2011 | Roschak |
| 2011/0152855 A1 | 6/2011 | Mayse et al. |
| 2011/0152967 A1 | 6/2011 | Simon et al. |
| 2011/0152974 A1 | 6/2011 | Rezai et al. |
| 2011/0166499 A1 | 7/2011 | Demarais et al. |
| 2011/0166565 A1 | 7/2011 | Wizeman et al. |
| 2011/0172654 A1 | 7/2011 | Barry et al. |
| 2011/0172655 A1 | 7/2011 | Biggs et al. |
| 2011/0172658 A1 | 7/2011 | Gelbart et al. |
| 2011/0178569 A1 | 7/2011 | Parnis et al. |
| 2011/0184330 A1 | 7/2011 | Laufer et al. |
| 2011/0190569 A1 | 8/2011 | Simon et al. |
| 2011/0196288 A1 | 8/2011 | Kaplan et al. |
| 2011/0202098 A1 | 8/2011 | Demarais et al. |
| 2011/0224768 A1 | 9/2011 | Edwards |
| 2011/0230701 A1 | 9/2011 | Simon et al. |
| 2011/0230938 A1 | 9/2011 | Simon et al. |
| 2011/0245756 A1 | 10/2011 | Arora et al. |
| 2011/0251592 A1 | 10/2011 | Biggs et al. |
| 2011/0257622 A1 | 10/2011 | Salahieh et al. |
| 2011/0257647 A1 | 10/2011 | Mayse et al. |
| 2011/0263960 A1 | 10/2011 | Mitchell |
| 2011/0264086 A1 | 10/2011 | Ingle |
| 2011/0270249 A1 | 11/2011 | Utley et al. |
| 2011/0276107 A1 | 11/2011 | Simon et al. |
| 2011/0276112 A1 | 11/2011 | Simon et al. |
| 2011/0282229 A1 | 11/2011 | Danek et al. |
| 2011/0282418 A1 | 11/2011 | Saunders et al. |
| 2011/0301587 A1 | 12/2011 | Deem et al. |
| 2011/0301664 A1 | 12/2011 | Rezai |
| 2011/0301679 A1 | 12/2011 | Rezai et al. |
| 2011/0306851 A1 | 12/2011 | Wang |
| 2011/0306904 A1 | 12/2011 | Jacobson et al. |
| 2011/0306997 A9 | 12/2011 | Roschak et al. |
| 2011/0319958 A1 | 12/2011 | Simon et al. |
| 2012/0004656 A1 | 1/2012 | Jackson et al. |
| 2012/0015019 A1 | 1/2012 | Pacetti et al. |
| 2012/0016256 A1 | 1/2012 | Mabary et al. |
| 2012/0016358 A1 | 1/2012 | Mayse et al. |
| 2012/0016363 A1 | 1/2012 | Mayse et al. |
| 2012/0016364 A1 | 1/2012 | Mayse et al. |
| 2012/0029261 A1 | 2/2012 | Deem et al. |
| 2012/0029500 A1 | 2/2012 | Jenson |
| 2012/0029512 A1 | 2/2012 | Willard et al. |
| 2012/0029591 A1 | 2/2012 | Simon et al. |
| 2012/0029601 A1 | 2/2012 | Simon et al. |
| 2012/0041412 A1 | 2/2012 | Roth et al. |
| 2012/0041509 A1 | 2/2012 | Knudson et al. |
| 2012/0071870 A1 | 3/2012 | Salahieh et al. |
| 2012/0078096 A1 | 3/2012 | Krolik et al. |
| 2012/0083734 A1 | 4/2012 | Ayres et al. |
| 2012/0089078 A1 | 4/2012 | Deem et al. |
| 2012/0089138 A1 | 4/2012 | Edwards et al. |
| 2012/0101326 A1 | 4/2012 | Simon et al. |
| 2012/0101413 A1 | 4/2012 | Beetel et al. |
| 2012/0109278 A1 | 5/2012 | Sih |
| 2012/0143132 A1 | 6/2012 | Orlowski |
| 2012/0143177 A1 | 6/2012 | Avitall |
| 2012/0143179 A1 | 6/2012 | Avitall |
| 2012/0143181 A1 | 6/2012 | Demarais et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0158101 A1 | 6/2012 | Stone et al. |
| 2012/0165803 A1 | 6/2012 | Bencini et al. |
| 2012/0172680 A1 | 7/2012 | Gelfand et al. |
| 2012/0184801 A1 | 7/2012 | Simon et al. |
| 2012/0185020 A1 | 7/2012 | Simon et al. |
| 2012/0191081 A1 | 7/2012 | Markowitz |
| 2012/0191082 A1 | 7/2012 | Markowitz |
| 2012/0197100 A1 | 8/2012 | Razavi et al. |
| 2012/0197246 A1 | 8/2012 | Mauch |
| 2012/0197251 A1 | 8/2012 | Edwards et al. |
| 2012/0203067 A1 | 8/2012 | Higgins et al. |
| 2012/0203216 A1 | 8/2012 | Mayse et al. |
| 2012/0203222 A1 | 8/2012 | Mayse et al. |
| 2012/0209118 A1 | 8/2012 | Warnking |
| 2012/0209259 A1 | 8/2012 | Danek et al. |
| 2012/0209261 A1 | 8/2012 | Mayse et al. |
| 2012/0209296 A1 | 8/2012 | Mayse et al. |
| 2012/0221087 A1 | 8/2012 | Parnis et al. |
| 2012/0232436 A1 | 9/2012 | Warnking et al. |
| 2012/0245415 A1 | 9/2012 | Emura et al. |
| 2012/0253336 A1 | 10/2012 | Littrup et al. |
| 2012/0253442 A1 | 10/2012 | Gliner et al. |
| 2012/0259263 A1 | 10/2012 | Celermajer et al. |
| 2012/0259269 A1 | 10/2012 | Meyer |
| 2012/0259326 A1 | 10/2012 | Brannan et al. |
| 2012/0265280 A1 | 10/2012 | Errico et al. |
| 2012/0289952 A1 | 11/2012 | Utley et al. |
| 2012/0290035 A1 | 11/2012 | Levine et al. |
| 2012/0294424 A1 | 11/2012 | Chin et al. |
| 2012/0296329 A1 | 11/2012 | Ng |
| 2012/0302909 A1 | 11/2012 | Mayse et al. |
| 2012/0310233 A1 | 12/2012 | Dimmer et al. |
| 2012/0316552 A1 | 12/2012 | Mayse et al. |
| 2012/0316559 A1 | 12/2012 | Mayse et al. |
| 2012/0330298 A1 | 12/2012 | Ganz et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0035576 A1 | 2/2013 | O'Grady et al. |
| 2013/0123751 A1 | 5/2013 | Deem et al. |
| 2013/0289555 A1 | 10/2013 | Mayse et al. |
| 2013/0289556 A1 | 10/2013 | Mayse et al. |
| 2013/0296647 A1 | 11/2013 | Mayse et al. |
| 2013/0303948 A1 | 11/2013 | Deem et al. |
| 2013/0310822 A1 | 11/2013 | Mayse et al. |
| 2013/0345700 A1 | 12/2013 | Hlavka et al. |
| 2014/0018789 A1 | 1/2014 | Kaplan et al. |
| 2014/0018790 A1 | 1/2014 | Kaplan et al. |
| 2014/0025063 A1 | 1/2014 | Kaplan et al. |
| 2014/0186341 A1 | 7/2014 | Mayse et al. |
| 2014/0236148 A1 | 8/2014 | Hlavka et al. |

(56) References Cited

U.S. PATENT DOCUMENTS

| | | |
|---|---|---|
| 2014/0257271 A1 | 9/2014 | Mayse et al. |
| 2014/0276792 A1 | 9/2014 | Kaveckis et al. |
| 2014/0316398 A1 | 10/2014 | Kelly et al. |
| 2014/0358136 A1 | 12/2014 | Kelly et al. |
| 2014/0371809 A1 | 12/2014 | Parnis et al. |
| 2015/0051597 A1 | 2/2015 | Mayse et al. |
| 2015/0126986 A1 | 5/2015 | Kelly et al. |
| 2015/0141985 A1* | 5/2015 | Mayse .............. A61B 18/1492 606/41 |
| 2015/0150625 A1 | 6/2015 | Deem et al. |
| 2015/0190193 A1 | 7/2015 | Mayse et al. |
| 2015/0366603 A1 | 12/2015 | Hlavka et al. |
| 2016/0022351 A1 | 1/2016 | Kaveckis et al. |
| 2016/0038725 A1 | 2/2016 | Mayse et al. |
| 2016/0192981 A1 | 7/2016 | Dimmer et al. |
| 2016/0220851 A1 | 8/2016 | Mayse et al. |
| 2016/0310210 A1 | 10/2016 | Harshman et al. |
| 2017/0014571 A1 | 1/2017 | Deem et al. |
| 2017/0050008 A1 | 2/2017 | Mayse |
| 2017/0245911 A1 | 8/2017 | Mayse et al. |
| 2018/0028748 A1 | 2/2018 | Deem et al. |

FOREIGN PATENT DOCUMENTS

| | | |
|---|---|---|
| CN | 101115448 A | 1/2008 |
| CN | 101448466 A | 6/2009 |
| CN | 101115448 B | 5/2010 |
| DE | 19529634 A1 | 2/1997 |
| DE | 19952505 A1 | 5/2001 |
| EP | 0189329 A3 | 6/1987 |
| EP | 0286145 A2 | 10/1988 |
| EP | 0280225 A3 | 3/1989 |
| EP | 0286145 A3 | 10/1990 |
| EP | 0282225 B1 | 6/1992 |
| EP | 0643982 A1 | 3/1995 |
| EP | 0908713 A1 | 4/1999 |
| EP | 1064886 A1 | 1/2001 |
| EP | 1143864 A2 | 10/2001 |
| EP | 1169972 A1 | 1/2002 |
| EP | 1271384 A1 | 1/2003 |
| EP | 1281366 A2 | 2/2003 |
| EP | 0908150 B1 | 5/2003 |
| EP | 0768091 B1 | 7/2003 |
| EP | 1326548 A1 | 7/2003 |
| EP | 1326549 A1 | 7/2003 |
| EP | 1400204 A1 | 3/2004 |
| EP | 1297795 B1 | 8/2005 |
| EP | 1588662 A2 | 10/2005 |
| EP | 2320821 B1 | 10/2012 |
| FR | 2659240 B1 | 7/1997 |
| GB | 2233293 A | 1/1991 |
| GB | 2233293 B | 2/1994 |
| JP | H06339453 A | 12/1994 |
| JP | H07289557 A | 11/1995 |
| JP | H0947518 A | 2/1997 |
| JP | H09243837 A | 9/1997 |
| JP | H1026709 A | 1/1998 |
| JP | 2000271235 A | 10/2000 |
| JP | 2001037773 A | 2/2001 |
| JP | 2002503512 A | 2/2002 |
| JP | 2002508989 A | 3/2002 |
| JP | 2002541905 A | 12/2002 |
| JP | 2003510126 A | 3/2003 |
| JP | 2011519699 A | 7/2011 |
| RU | 2053814 C1 | 2/1996 |
| RU | 2091054 C1 | 9/1997 |
| WO | WO-8911311 A1 | 11/1989 |
| WO | WO-9301862 A1 | 2/1993 |
| WO | WO-9304734 A1 | 3/1993 |
| WO | WO-9316632 A1 | 9/1993 |
| WO | WO-9407446 A1 | 4/1994 |
| WO | WO-9501075 A1 | 1/1995 |
| WO | WO-9502370 A2 | 1/1995 |
| WO | WO-9510322 A1 | 4/1995 |
| WO | WO-9604860 A1 | 2/1996 |
| WO | WO-9610961 A1 | 4/1996 |
| WO | WO-9725917 A1 | 7/1997 |
| WO | WO-9732532 A1 | 9/1997 |
| WO | WO-9733715 A1 | 9/1997 |
| WO | WO-9737715 A1 | 10/1997 |
| WO | WO-9740751 A1 | 11/1997 |
| WO | WO-9818391 A1 | 5/1998 |
| WO | WO-9844854 A1 | 10/1998 |
| WO | WO-9852480 A1 | 11/1998 |
| WO | WO-9856234 A1 | 12/1998 |
| WO | WO-9856324 A1 | 12/1998 |
| WO | WO-9903413 A1 | 1/1999 |
| WO | WO-9858681 A3 | 3/1999 |
| WO | WO-9913779 A2 | 3/1999 |
| WO | WO-9932040 A1 | 7/1999 |
| WO | WO-9935986 A1 | 7/1999 |
| WO | WO-9935988 A1 | 7/1999 |
| WO | WO-9942044 A1 | 8/1999 |
| WO | WO-9942047 A1 | 8/1999 |
| WO | WO-9964109 A1 | 12/1999 |
| WO | WO-0010598 A2 | 3/2000 |
| WO | WO-0051510 A1 | 9/2000 |
| WO | WO-0062699 A2 | 10/2000 |
| WO | WO-0066017 A1 | 11/2000 |
| WO | WO-0100114 A1 | 1/2001 |
| WO | WO-0103642 A1 | 1/2001 |
| WO | WO-0122897 A1 | 4/2001 |
| WO | WO-0170114 A1 | 9/2001 |
| WO | WO-0189526 A1 | 11/2001 |
| WO | WO-0205720 A1 | 1/2002 |
| WO | WO-0205868 A2 | 1/2002 |
| WO | WO-0232333 A1 | 4/2002 |
| WO | WO-0232334 A1 | 4/2002 |
| WO | WO-03073358 A2 | 9/2003 |
| WO | WO-03086524 A1 | 10/2003 |
| WO | WO-03088820 A2 | 10/2003 |
| WO | WO-2004078252 A2 | 9/2004 |
| WO | WO-2004082736 A2 | 9/2004 |
| WO | WO-2004101028 A2 | 11/2004 |
| WO | WO-2005006963 A2 | 1/2005 |
| WO | WO-2005006964 A2 | 1/2005 |
| WO | WO 2005/074829 | 8/2005 |
| WO | WO-2006053308 A2 | 5/2006 |
| WO | WO-2006053309 A2 | 5/2006 |
| WO | WO-2006116198 A2 | 11/2006 |
| WO | WO-2007001981 A2 | 1/2007 |
| WO | WO-2007058780 A2 | 5/2007 |
| WO | WO-2007061982 A1 | 5/2007 |
| WO | WO-2007092062 A1 | 8/2007 |
| WO | WO-2007094828 A2 | 8/2007 |
| WO | WO-2007143665 A2 | 12/2007 |
| WO | WO-2008005953 A2 | 1/2008 |
| WO | WO-2008024220 A1 | 2/2008 |
| WO | WO-2008051706 A2 | 5/2008 |
| WO | WO-2008063935 A2 | 5/2008 |
| WO | WO-2008071914 A2 | 6/2008 |
| WO | WO-2009009236 A1 | 1/2009 |
| WO | WO-2009015278 A1 | 1/2009 |
| WO | WO-2009082433 A2 | 7/2009 |
| WO | WO-2009126383 A2 | 10/2009 |
| WO | WO-2009137819 A1 | 11/2009 |
| WO | WO-2010110785 A1 | 9/2010 |
| WO | WO-2011056684 A2 | 5/2011 |
| WO | WO-2011060200 A1 | 5/2011 |
| WO | WO-2011127216 A2 | 10/2011 |

OTHER PUBLICATIONS

Accad M., "Single-Step Renal Denervation with the OneShot™ Ablation System," Presentation at the Leipzig Interventional Course 2012 in Leipzig, Germany, Jan. 26, 2012, 11 pages.

Ahnert-Hilger., et al., "Introduction of Macromolecules into Bovine Adrenal-Medullary Chromaffin Cells and Rat Pheochromocytoma Cells (PC12) by Permeabilization with Streptolysin O: Inhibitory Effect of Teanus Toxin on Catecholamine Secretion," J. Neurochem, Jun. 1989, vol. 52 (6), pp. 1751-1758.

(56) References Cited

OTHER PUBLICATIONS

Amendment After Allowance dated Sep. 17, 2012, in co-pending U.S. Appl. No. 12/372,607, filed Feb. 17, 2009.
An S S., et al., "Airway Smooth Muscle Dynamics; A Common Pathway of Airway Obstruction in Asthma," European Respiratory Journal, 2007, vol. 29 (5), pp. 834-860.
Application and File History for European Patent Application No. 09743805.5 filed May 8, 2009.
Application and File History for European Patent Application No. 10774097.9 filed Oct. 27, 2010.
Application and File History for European Patent Application No. 10779422.4 filed Nov. 11, 2010.
Application and File History for European Patent Application No. 12005299.8 filed Jul. 18, 2012.
Application and File History for European Patent Application No. 13003665.0 filed Jul. 22, 2013.
Application and File History for European Patent Application No. 13003666.8 filed Jul. 22, 2013.
Application and File History for European Patent Application No. 13003667.6 filed Jul. 22, 2013.
Application and File History for U.S. Appl. No. 09/095,323, filed Jun. 6, 1998, inventor Laufer.
Application and File History for U.S. Appl. No. 13/168,893, filed Jun. 24, 2011, inventors Mayse et al.
Application and File History for U.S. Appl. No. 13/245,522, filed Sep. 26, 2011, issued as U.S. Pat. No. 8,226,638 on Jul. 24, 2012, inventors Mayse et al.
Application and File History for U.S. Appl. No. 13/245,529, filed Sep. 26, 2011, inventors Mayse et al.
Application and File History for U.S. Appl. No. 13/245,537, filed Sep. 26, 2011, issued as U.S. Pat. No. 8,932,289 on Jan. 13, 2015, inventors Mayse et al.
Application and File History for U.S. Appl. No. 13/452,648, filed Apr. 20, 2012, issued as U.S. Pat. No. 8,961,507 on Feb. 24, 2015, inventors Mayse et al.
Application and File History for U.S. Appl. No. 13/452,655, filed Apr. 20, 2012, issued as U.S. Pat. No. 8,961,508 on Feb. 24, 2015, inventors Mayse et al.
Application and File History for U.S. Appl. No. 13/452,660, filed Apr. 20, 2012, issued as U.S. Pat. No. 8,821,489 on Sep. 2, 2014, inventors Mayse et al.
Application and File History for U.S. Appl. No. 13/452,664, filed Apr. 20, 2012, issued as U.S. Pat. No. 8,808,280 on Aug. 19, 2014, inventors Mayse et al.
Application and File History for U.S. Appl. No. 13/509,581, filed Aug. 14, 2012, now U.S. Pat. No. 9,149,328 issued Oct. 6, 2015, inventors Dimmer et al.
Application and File History for U.S. Appl. No. 13/523,223, filed Jun. 14, 2012, issued as U.S. Pat. No. 8,489,192 on Jul. 16, 2013, inventors Hlavka et al.
Application and File History for U.S. Appl. No. 13/584,142, filed Aug. 13, 2012, inventors Mayse et al.
Application and File History for U.S. Appl. No. 13/592,075, filed Aug. 22, 2012, inventors Mayse et al.
Application and File History for U.S. Appl. No. 13/894,920, filed May 15, 2013, inventors Mayse et al.
Application and File History for U.S. Appl. No. 13/920,801, filed Jun. 18, 2013, issued as U.S. Pat. No. 8,731,672 on May 20, 2014, inventors Hlavka, et al.
Application and File History for U.S. Appl. No. 13/930,825, filed Jun. 28, 2013, issued as U.S. Pat. No. 8,740,895 on Jun. 3, 2014, inventors Mayse et al.
Application and File History for U.S. Appl. No. 13/931,208, filed Jun. 28, 2013, issued as U.S. Pat. No. 8,777,943 on Jul. 15, 2014, inventors Mayse et al.
Application and File History for U.S. Appl. No. 13/931,246, filed Jun. 28, 2013, inventors Mayse et al.
Application and File History for U.S. Appl. No. 14/349,599, filed Apr. 3, 2014, inventors Mayse, et al.
Application and File History for U.S. Appl. No. 14/529,335, filed Oct. 31, 2014, inventors Mayse et al.
Application and File History for U.S. Appl. No. 14/601,717, filed Jan. 21, 2015, inventors Mayse et al.
Application and File History of U.S. Appl. No. 12/463,304, Inventor: Martin L. Mayse, et al., filed May 8, 2009, Issued as U.S. Pat. No. 8,088,127 on Jan. 3, 2012, Systems, Assemblies, and Methods for Treating a Bronchial Tree.
Application and File History of U.S. Appl. No. 12/913,702, Inventor: Martin L. Mayse, et al., filed Oct. 27, 2010, Delivery Devices With Coolable Energy Emitting Assemblies.
Awadh N., et al., "Airway Wall Thickness in Patients with Near Fatal Asthma and Control Groups: Assessment with High Resolution Computed Tomographic Scanning," Thorax, 1998, vol. 53, pp. 248-253.
Babichev., et al., "Clinico-Morphological Comparisons in Patients with Bronchial Asthma after Denervation of the Lungs," Sov Med, 1985, vol. 12, pp. 13-16.
Babichev., et al., "Long-term Results of Surgical Treatment of Bronchial Asthma Based on Adaptive Response," Khirurgiia (Mosk), 1993, vol. 4, pp. 5-11.
Babichev., et al., "Partial Denerarion of the Lungs in Bronchial Asthma," Khirurgiia (Mosk), 1985, vol. 4, pp. 31-35.
Barlaw., "Surgical Treatment of Asthma," Postgrad Med. Journal, 1949, vol. 25, pp. 193-196.
Bel E H., "Hot Stuff: Bronchial Thermoplasty for Asthma," American Journal of Respiratory and Critical Care Medicine, 2006, vol. 173, pp. 941-942.
Bertog S., "Covidien-Maya: OneShot.TM.," presentation at the 2012 Congenital & Structural Interventions Congress in Frankfurt, Germany, Jun. 28, 2012, 25 pages.
Bester., et al., "Recovery of C-Fiber-Induced Extravasation Following Peripheral Nerve Injury in the Rat," Experimental Neurology, 1998, vol. 154, pp. 628-636.
Bigalke., et al., "Clostridial Neurotoxins," Handbook of Experimental Pharmacology (Aktories, K., and Just, I., eds), 2000, vol. 145, pp. 407-443.
Bittner., et al., "Isolated Light Chains of Botulinum Neurotoxins Inhibit Exocytosis," The Journal of Biological Chemistry, 1989, vol. 264(18), pp. 10354-10360.
Blindt., et al., "Development of a New Biodegradable Intravascular Polymer Stent with Simultaneous Incorporation of Bioactive Substances," The International Journal of Artificial Organs, 1999, vol. 22 (12), pp. 843-853.
Boxem V TJM., et al., "Tissue Effects of Bronchoscopic Electrocautery," Chest, Mar. 1999, vol. 117(3), pp. 887-891.
Bradley., et al., "Effect of Vagotomy on the Breathing Pattern and Exercise Ability in Emphysematous Patients," Clinical Science, 1982, vol. 62, pp. 311-319.
Breekveldt-Postma., et al., "Enhanced Persistence with Tiotropium Compared with Other Respiratory Drugs in COPD," Respiratory Medicine, 2007, vol. 101, pp. 1398-1405.
Brody., et al., "Mucociliary Clearance After Lung Denervation and Bronchial Transection," J Applied Physiology, 1972, vol. 32 (2), pp. 160-164.
Brown R H., et al., "Effect of Bronchial Thermoplasty on Airway Distensibility," European Respiratory Journal, Aug. 2005, vol. 26 (2), pp. 277-282.
Brown R H., et al., "In Vivo Evaluation of the Effectiveness of Bronchial Thermoplasty with Computed Tomography," Journal of Applied Physiology, 2005, vol. 98, pp. 1603-1606.
Buzzi., "Diphtheria Toxin Treatment of Human Advanced Cancer," Cancer Research, 1982, vol. 42, pp. 2054-2058.
Canning., et al., "Reflex Mechanisms in Gastroesophageal Reflux Disease and Asthma," The American Journal of Medicine, 2003, vol. 115 (3A), pp. 45S-48S.
Canning., "Reflex Regulation of Airway Smooth Muscle Tone," J Appl. Physiol, 2006, vol. 101, pp. 971-985.
Castro M., et al., "Effectiveness and Safety of Bronchial Thermoplasty in the Treatment of Severe Asthma: a Multicenter, Randomized, Double-Blind, Sham-Controlled Clinical Trial," American Journal of Respiratory and Critical Care Medicine, 2010, vol. 181, pp. 116-124.

(56) References Cited

OTHER PUBLICATIONS

Chaddock., et al., "Expression and Purification of Catalytically Active, Non-Toxic Endopeptidase Derivatives of Clostridium Botulinum Toxin Type A," Protein Expression and Purification, Jul. 2002, vol. 25 (2), pp. 219-228.
Chang., "Cell Poration and Cell Fusion Using an Oscillating Electric Field," Biophys. J, 1989, vol. 56, pp. 641-652.
Chernyshova., et al., "The Effect of Low-Energy Laser Radiation in the Infrared Spectrum on Bronchial Patency in Children with Bronchial Asthma," Vopr Kurortol Fizioter Lech Fiz Kult, 1995, vol. 2, pp. 11-14, (6 pages of English translation).
Chhajed P., "Will There be a Role for Bronchoscopic Radiofrequency Ablation," J Bronchol, 2005, vol. 12 (3), p. 184.
Chumakov., et al., "Morphologic Studies of Bronchial Biopsies in Chronic Bronchitis Before and After Treatment," Arkh Patol, 1995, vol. 57 (6), pp. 21-25.(English Abstract and Translation, 8 pages).
Communication dated May 20, 2016 for EP Application No. 13003665.0, filed May 8, 2009, 4 pages.
Communication dated May 20, 2016 for EP Application No. 13003666.8, filed May 8, 2009, 5 pages.
Co-pending U.S. Appl. No. 09/095,323, filed Jun. 10, 1998, 25 pages.
Co-pending U.S. Appl. No. 09/244,173, filed Feb. 4, 1999.
Co-pending U.S. Appl. No. 12/372,607, filed Feb. 17, 2009.
Co-pending U.S. Appl. No. 13/523,223, filed Jun. 14, 2012.
Cox G., et al., "Asthma Control During the Year After Bronchial Thermoplasty," The New England Journal of Medicine, Mar. 29, 2007, vol. 356 (13), pp. 1327-1337.
Cox G., et al., "Bronchial Thermoplasty for Asthma," American Journal of Respiratory and Critical Care Medicine, 2006, vol. 173, pp. 965-969.
Cox G., et al., "Bronchial Thermoplasty: Long-Tenn Follow-up and Patient Satisfaction," 2004, 1 page.
Cox G., et al., "Bronchial Thermoplasty: One-Year Update, American Thoracic Society Annual Meeting," 2004, 1 page.
Cox G., et al., "Clinical Experience with Bronchial Thermoplasty for the Treatment of Asthma," Chest 124, 2003, p. 106S.
Cox G., et al., "Development of a Novel Bronchoscope Therapy for Asthma," Journal of Allergy and Clinical Immunology, 2003, 1 page.
Cox G., et al., "Early Clinical Experience With Bronchial Thermoplasty for the Treatment of Asthma," 2002, p. 1068.
Cox G., et al., "Impact of Bronchial Thermoplasty on Asthma Status: Interim Results From the Air Trial," European Respiratory Society Annual Meeting, Munich, Germany, 2006, 1 page.
Cox G., et al., "Radiofrequency Ablation of Airway Smooth Muscle for Sustained Treatment of Asthma: Preliminary Investigations," European Respiratory Journal, 2004, vol. 24, pp. 659-663.
Crimi., et al., "Protective Effects of Inhaled Ipratropium Bromide on Bronchoconstriction Induced by Adenosine and Methacholine in Asthma," Eur Respir J, 1992, vol. 5, pp. 560-565.
Danek C J., et al., "Asthma Intervention Research (AIR) Trial Evaluating Bronchial Hermoplasty.TM.; Early Results," American Thoracic Society Annual Meeting, 2002, 1 page.
Danek C J., et al., "Bronchial Thermoplasty Reduces Canine Airway Responsiveness to Local Methacholine Challenge," American Thoracic Society Annual Meeting, 2002, 1 page.
Danek C J., et al., "Reduction in Airway Hyperesponsiveness to Methacholine by the Application of RF Energy in Dogs," J Appl Physiol, 2004, vol. 97, pp. 1946-1933.
De Paiva., et al., "Light Chain of Botulinum Neurotoxin is Active in Mammalian Motor Nerve Terminals When Delivered Via Liposomes," FEBS Lett, Dec. 1990, vol. 17:277(1-2), pp. 171-174.
Dierkesmann., et al., "Indication and Results of Endobronchial Laser Therapy," Lung, 1990, vol. 168, pp. 1095-1102.
Dimitrov-Szokodi., et al., "Lung Denervation in the Therapy of Intractable Bronchial Asthma," J. Thoracic Surg, Feb. 1957, vol. 33 (2), pp. 166-184.
Donohue., et al., "A 6-Month, Placebo-Controlled Study Comparing Lung Function and Health Status Changes in COPD Patients Treated With Tiotropium or Salmeterol," Chest, 2002, vol. 122, pp. 47-55.
English Translation of Office Action dated Jul. 13, 2014 for Japanese Application No. JP 2012-538992, filed Nov. 11, 2010, 2 pages.
European Communication dated Oct. 31, 2013 for European Application No. 12005299.8, filed May 8, 2009.
European Search Report for European Application No. 13003665, dated Oct. 8, 2013.
European Search Report for European Application No. 13003667, dated Oct. 8, 2013.
European Search Report mailed for European Application No. 13003666, dated Oct. 8, 2013.
"Evis Exera Bronchovideoscope Brochure," Olympus Bf-XT160, Olympus, Jun. 15, 2007, 2 pages.
Extended European Search Report for European Application No. 13003667.6, dated Oct. 16, 2013, 9 pages.
Extended European Search Report for European Application No. 13003665.0, dated Oct. 16, 2013, 8 pages.
Extended European Search Report for European Application No. 13003666.8, dated Oct. 16, 2013, 7 pages.
Extended European Search Reportfor Application No. 14188819.8, dated Jan. 29, 2015, 7 pages.
File History Portions for Application No. 15164210.5, dated Sep. 17, 2015, 8 pages.
Feshenko., et al., "Clinico-Morphological Comparisons in the Laser Therapy of Chronic Bronchitis Patients," Lik Sprava, 1993, vol. 10-12, pp. 75-79.(English abstract, 1 Page).
Final Office Action dated Oct 30, 2014 for Japanese Application No. JP 2011508719, filed May 8, 2009, 8 pages.
Friedman., et al., "Healthcare Costs with Tiotropium Plus Usual Care versus Usual Care Alone Following 1 Year of Treatment in Patients with Chronic Obstructive Pulmonary Disorder (COPD)," Pharmacoeconomics, 2004, vol. 22 (11), pp. 741-749.
Gaude., G.S., "Pulmonary Manifestations of Gastroesophageal Reflux Disease," Annals of Thoracic Medicine, Jul.-Sep. 2009, vol. 4 (3), pp. 115-123.
Gelb., et al., "Laser in Treatment of Lung Cancer," American College of Chest Physicians, Nov. 1984, vol. 86 (5), pp. 662-666.
George., et al., "Factors Associated With Medication Nonadherence in Patients With COPD," Chest, 2005, vol. 128, pp. 3198-3204.
Gerasin., et al., "Endobronchial Electrosurgery," Chest, 1988, vol. 93, pp. 270-274.
Gibson., et al., "Gastroesophageal Reflux Treatment for Asthma in Adults and Children," Cochrane Database Syst. Rev. 2:CD001496, 2003. (Abstract only).
Glanville., et al., "Bronchial Responsiveness after Human Heart-Lung Transplantation," Chest, 1990, vol. 97 (6), pp. 1360-1366.
Glanville., et al., "Bronchial Responsiveness to Exercise after Human Cardiopulmonary Transplantation," Chest, 1989, vol. 96 (2), pp. 81-286.
"Global Strategy for Asthma Management and Prevention," 2002, 192 pages.
Gosens., et al., "Muscarinic Receptor Signaling in the Pathophysiology of Asthma and COPD," Respiratory Research, 2006, vol. 7 (73), pp. 1-15.
Grey H., "Anatomy of the Human Body, Lea and Febiger," Philadelphia, 1918, sections 1 b and le. (Abstract only).
Groeben., et al., "High Thoracic Epidural Anesthesia Does Not Alter Airway Resistance and Attenuates the Response to an Inhalational Provocation Test in Patients with Bronchial Hyperreactivity," Anesthesiology, 1994, vol. 81 (4), pp. 868-874.
Guarini., et al., "Efferent Vagal Fibre Stimulation Blunts Nuclear Factor-kB Activation and Protects Against Hypovolemic Hemmorrhagic Shock," Circulation, 2003, vol. 107, pp. 1189-1194.
Guzman., et al., "Bioeffects Caused by Changes in Acoustic Cavitation Bubble Density and Cell Concentration: A Unified Explanation Based on Cell-to-Bubble Ratio and Blast Radius," Ultrasound in medicine & biology, 2003, vol. 29 (8), pp. 1211-1222.
Hainsworth., et al., "Afferent Lung Denervation by Brief Inhalation of Steam," Journal of Applied Physiology, May 1972, vol. 34 (5), pp. 708-714.

(56) References Cited

OTHER PUBLICATIONS

Harding., "Recent Clinical Investigations Examining the Association of Asthma and Gastroesophageal Reflux," The American Journal of Medicine, 2003, vol. 115 (Suppl 3A), pp. 39S-44S. (Abstract only).
Hiraga., "Experimental surgical therapy of bronchial asthma. The effect of denervation in dogs," Nihon Kyobu Shikkan Gakkai Zasshi, 1981, vol. 19 (1), pp. 46-56.
Hoffmann., et al., "Inhibition of Histamine-Induced Bronchoconstriction in Guinea Pig and Swine by Pulsed Electrical Vagus Nerve Stimulation," Neuromodulation: Technology at the Neural Interface, 2009, pp. 1-9.
Hogg J.C., et a., "The Pathology of Asthma," APMIS, Oct. 1997, vol. 105 (10), pp. 735-745.
Hooper., et al., "Endobronchial Electrocautery," Chest, 1985, vol. 87 (6), pp. 12-714.
Ivanyuta O M., et al., "Effect of Low-Power Laser Irradiation of Bronchia Mucosa on the State of Systemic and Local Immunity in Patients with Chronic Bronchitis," Problemy Tuberkuleza, 1991, vol. 6, pp. 26-29.
James., et al., "The Mechanics of Airway Narrowing in Asthma," The American Review of Respiratory Disease, 1989, vol. 139, pp. 242-246.
Jammes., et al., "Assessment of the Pulmonary Origin of Bronchoconstrictor Vagal Tone," The Journal of physiology, 1979, vol. 291, pp. 305-316.
Janssen L. J., "Asthma therapy: how far have we come, why did we fail and where should we go next?," European Respiratory Journal, 2009, vol. 33, pp. 11-20.
Jiang., et al., "Effects of Antireflux Treatment on Bronchial Hyperresponsiveness and Lung Function in Asthmatic Patients with Gastroesophageal Reflux Disease," World Journal of Gastroenterology, 2003, vol. 9, pp. 1123-1125. (Abstract only).
Johnson S R., et al., "Synthetic Functions of Airway Smooth Muscle in Asthma," Trends in Pharmacological Sciences, Aug. 1997, vol. 18 (8), pp. 288-292.
Karashurov., et al., "Electrostimulation in the Therapy of Bronchial Asthma," Klin Med (Mosk), 2001, vol. 79 (11), pp. 38-41.
Karashurov., et al., "Radiofrequency Electrostimulation of Carotid Sinus Nerves for the treatment of Bronchial Asthma," Khirurgiia (Mosk), 1999, vol. 12, pp. 2-6.
Keith M L., "Clinically Oriented Anatomy," Williams & Wilkins, Baltimore, 1985, 2nd edition, pp. 85 and 87(Abstract only).
Khmel'Kova et al., "Does laser irridation affect bronchial obstruction?," Probl Tuberk, 1995, vol. 3, pp. 41-42 (Abstract only).
Khoshoo., et al., "Role of Gastroesophageal Reflux in Older Children with Persistent Asthma," Chest, 2003, vol. 123, pp. 1008-1013.
Kiljander., "The Role of Proton Pump Inhibitors in the Management of Gastroesophageal Reflux Disease-Related Asthma and Chronic Cough," The American Journal of Medicine, 2003, vol. 115 (Suppl 3A), pp. 65S-71S. (Abstract only.).
Kistner., et al., "Reductive Cleavage of Tetanus Toxin and Botulinum Neurotoxin A by the Thioredoxin System from Brain," Naunyn-Schmiedebergs Arch Pharmacal, Feb., 1992, vol. 345 (2), pp. 227-234.
Kitamura S., "Color Atlas of Clinical Application of Fiberoptic Bronchoscopy," 1990, Year Book Medical Publishers, pp. 17.
Kletskin., et al., "Value of Assessing the Autonomic Nervous System in Bronchial Asthma in Selecting the Surgical Treatment Method," Khirurgiia (Mosk), 1987, vol. 7, pp. 91-95.
Kliachkin., et al., "Bronchoscopy in the Treatment of Bronchial Asthma of Infectious Allergic Origin," Terapevticheskii arkhiv, 1982, vol. 54 (4), pp. 76-79.
Korochkin., et al., "Use of a Helium-Neon Laser in Combined Treatment of Bronchial Asthma," New Developments in Diagnostics and Treatment, 1990, 9 pages.
Korochkin et al., "Use of the Helium-Neon Laser in the Multimodal Treatment of Bronchial Asthma," Sov Med, 1990, vol. 6, pp. 18-20.
Korpela., et al., "Comparison of Tissue Reactions in the Tracheal Mucosa Surrounding a Bioabsorbable and Silicone Airway Stents," Annals of Thoracic Surgery, 1998, vol. 66, pp. 1772-1776.
Kozaki., et al., "New Surgical Treatment of Bronchial Asthma—Denervation of the Hilus Pulmonis (2)," Nippon Kyobu Geka Gakkai Zasshi, 1974, vol. 22 (5), pp. 465-466.
Kraft M., "The Distal Airways: Are they Important in Asthma?," European Respiratory, 1999, pp. 1403-1417.
Kreitman., "Taming Ricin Toxin," Nature Biotechnology, 2003, vol. 21, pp. 372-374.
Kuntz., "The Autonomic Nervous System in Relation to the Thoracic Viscera," Chest, 1944, vol. 10, pp. 1-18.
Lavioletts et al., "Asthma Intervention Research (AIR) Trial: Early Safety Assessment of Bronchial Thermoplasty," 2004, 1 page.
Leff., et al., "Bronchial Thermoplasty Alters Airway Smooth Muscle and Reduces Responsiveness in Dogs; A Possible Procedure for the Treatment of Asthma," American Thoracic Society Annual Meeting, 2002, 1 page.
Lennerz., et al., "Electrophysiological Characterization of Vagal Afferents Relevant to Mucosal Nociception in the Rat Upper Oesophagus," The Journal of physiology, 2007, vol. 582 (1), pp. 229-242.
Levin., "The Treatment of Bronchial Asthma by Dorsal Sympathectomy," Annals of Surgery, 1935, vol. 102 (2), pp. 161-170.
Lim E E., et al., "Botulinum Toxin: A Novel Therapeutic Option for Bronchial Asthma?," Medical Hypotheses, 2006, vol. 66, pp. 915-919.
Liou., et al., "Causative and Contributive Factors to Asthmas Severity and Patterns of Medication Use in Patients Seeking Specialized Asthma Care," Chest, 2003, vol. 124, pp. 1781-1788. (Abstract only).
Lokke., et al., "Developing COPD: A 25 Year Follow Up Study of the General Population," Thorax, 2006, vol. 61, pp. 935-939.
Lombard., et al., "Histologic Effects of Bronchial Thermoplasty of Canine and Human Airways," American Thoracic Society Annual Meeting, 2002, 1 page.
Macklem P T., "Mechanical Factors Determining Maximum Bronchoconstriction, European Respiratory Journal," Jun. 1989, vol. 6, pp. 516s-519s.
Maesen., et al., "Tiotropium Bromide, A New Long-Acting Antimuscarinic Bronchodilator: A Pharmacodynamic Study in Patients with Chronic Obstructive Pulmonary Disease (COPD)," The European Respiratory Journal, 1995, vol. 8, pp. 1506-1513.
Magnussen., et al., "Effect of Inhaled Ipratropium Bromide on the Airway Response to Methacholine, Histamine, and Exercise in Patients with Mild Bronchial Asthma," Respiration, 1992, vol. 59, pp. 42-47.
Maltais., et al., "Improvements in Symptom-Limited Exercise Performance Over 8 h With Once-Daily Tiotropium in Patients With COPD," Chest, 2005, vol. 128, pp. 1168-1178.
Martin N., et al., "Bronchial Thermoplasty for the Treatment of Asthma," Current Allergy and Asthma Reports, Jan. 2009, vol. 9 (1), pp. 88-95.
Mathew., et al., "Gastro-Oesophageal Reflux and Bronchial Asthma: Current Status and Future Directions," Postgraduate Medical Journal, 2004, vol. 80, pp. 701-705.
Matthias O., et al., "Fisherman's Pulmonary Diseases and Disorders," Functional Design of the Human Lung for Gas Exchange, McGraw Hill Medical, New York, Edition 4, 2008, Chapter 2(Abstract only).
Mayse M., et al., "Clinical Pearls for Bronchial Thermoplasty," J Bronchol, Apr. 2007, vol. 14 (2), pp. 115-123.
McEvoy C E., et al., "Changing the Landscape: Bronchial Thermoplasty Offers a Novel Approach to Asthma Treatment," Advance for Managers of Respiratory Care, Oct. 24-25, 2007, pp. 22.
McKay., et al., "Autocrine Regulation of Asthmatic Airway Inflammation: Role of Airway Smooth Muscle," Respiratory Research, 2002, vol. 3 (11), pp. 1-13.
Mehta., et al., "Effect of Endobronchial Radiation therapy on Malignant Bronchial Obstruction," Chest, Mar. 1990, vol. 97 (3), pp. 662-665.

(56) References Cited

OTHER PUBLICATIONS

Meshalkin., et al., "Partial Denervation of the Pulmonary Hilus as One of the Methods of Surgical Treatment of Bronchial Asthma," Grudnaia Khirurgiia, 1975, vol. 1, pp. 109-111.
Michaud G., et al., "Positioned for Success: Interest in Diagnostic and Therapeutic Bronchoscopy is Growing," Advance for Managers of Respiratory Care, Jul.-Aug. 2008, pp. 40, 42-43.
Miller J D., et al., "A Prospective Feasibility Study of Bronchial Thermoplasty in the Human Airway," 2005, vol. 127 (6), pp. 1999-2006.
Miller J D., et al., "Bronchial Thermoplasty is Well Tolerated by Non-Asthmatic Patients Requiring Lobectomy," American Thoracic Society Annual Meeting, 2002, 1 page.
Mitzner W., "Airway Smooth Muscle Rhe appendix of the Lung," American Journal of Respiratory and Critical Care Medicine, 2004, vol. 169, pp. 787-790.
Mitzner W., "Bronchial Thermoplasty in Asthma," Allergology International, 2006, pp. 55, 225-234.
Montaudon M., et al., "Assessment of Bronchial Wall Thickness and Lumen Diameter in Human Adults Using Multi-Detector Computed Tomography: Comparison with Theoretical Models," Journal of Anatomy, 2007, vol. 211, pp. 579-588.
Netter F H., Respiratory System: A Compilation of Paintings Depicting Anatomy and Embryology, Physiology, Pathology, Pathophysiology, and Clinical Features and Treatment of Diseases, In the CIBA Collection of Medical Illustrations M.B. Divertie, ed., Summit: New Jersey, 1979, vol. 7, pp. 119-135.
Netter F H., "The Ciba Collection of Medical Illustrations," Respiratory System, CIBA-GEIGY Corporation, West Caldwell, 1979, p. 23, section 1. (Abstract only).
Non-Final Office Action dated Apr. 27, 2010 for U.S. Appl. No. 11/398,353, filed Apr. 4, 2006, 8 pages.
Non-Final Office Action dated Aug. 31, 2009 for U.S. Appl. No. 11/398,353, filed Apr. 4, 2006, 7 pages.
Notice of final Rejection dated Sep. 2, 2008 for Japanese Patent Application No. 2000-553172, filed Jun. 9, 1999, 5 pages.
O'Connor., et al., "Prolonged Effect of Tiotropium Bromide on Methacholine-induced Bronchoconstriction in Asthma," American Journal of Respiratory and Critical Care Medicine, 1996, vol. 154, pp. 876-880.
Office Action dated Apr. 7, 2015 for Australian Patent Application No. 2010315396 filed Oct. 27, 2010, 4 pages.
Office Action dated Aug. 10, 2015 for Canadian Application No. 2,723,806 filed May, 8, 2009, 4 pages.
Office Action dated Feb. 10, 2016 for Australian Application No. 2010315396 filed Oct. 27, 2010, 3 pages.
Office Action dated Jul. 12, 2016 for Japanese Application No. 2015-162994 filed Aug. 20, 2015 , 8 pages.
Office Action dated May 14, 2015 for Chinese Application No. 201080060627.6 filed Nov. 11, 2010, 7 pages.
Office Action dated Jun. 20, 2016 for Chinese Application No. 201410250553.2 filed Oct. 27, 2010, 8 pages.
Office Action dated Sep. 20, 2016 for Canadian Application No. 2,723,806 May 8, 2009, 5 pages.
Office Action dated Jan. 22, 2016 for Canadian Application No. 2,779,135 filed Oct. 27, 2010, 7 pages.
Office Action dated Jan. 22, 2016 for JP Application No. 2015-014893 filed Jan. 29, 2015, 11 pages.
Office Action dated Mar. 24, 2015 for Japanese Application No. 2012-538992 filed Nov. 11, 2010, 5 pages.
Office Action dated Sep. 9, 2016 for Chinese Application No. 201510166836.3, Oct. 27, 2010, 5 pages.
Office Action dated Oct. 2, 2013 for Japanese Application No. 2011-508719 filed May 8, 2009.
Office Action dated Jul. 11, 2014 for Japanese Application No. 2012-537018, filed Oct. 27, 2010, 7 pages.
Office Action dated Nov. 11, 2013 for Chinese Patent Application 200980116717.X, filed May 8, 2009, 5 pages.
Office Action dated Nov. 11, 2013 from Application CN 200980116717 filed May 8, 2009, 5 pages.
Office Action dated May 13, 2013 from European Application No. 10774097.9, filed Oct. 27, 2010, 4 pages.
Office Action dated Oct. 14, 2016 for Canadian Application No. 2,780,608 filed Nov. 11, 2010, 4 pages.
Office Action dated Feb. 15, 2016 from Chinese Application CN 201080060627.6, filed Nov. 11, 2010, 6 pages. (No English translation available).
Office Action dated Feb. 16, 2016 from Japanese Application JP 2012-538992 filed Nov. 11, 2010, 2 pages. (No English translation available).
Office Action dated Sep. 16, 2015 for KR Application No. 1020107026952, filed May 8, 2009, 17 pages.
Office Action dated Jun. 2, 2015 for Japanese Application No. 2012-537018, filed Oct. 27, 2010, 2 pages.
Office Action dated Sep. 20, 2013 from Japanese Application 2011-508719, filed May 8, 2009, 3 pages. (English translation of relevant portions).
Office Action dated Sep. 22, 2015 for CN Application No. 201410250553.2, filed Oct. 27, 2010, 3 pages.
Office Action dated Apr. 25, 2014 from Japanese Application 2011-508719, filed May 8, 2009, 2 pages. (English translation of relevant portions).
Office Action dated Jun. 27, 2014 for Chinese Application No. 201080048938.0, filed Oct. 27, 2010, 12 pages.
Office Action dated Mar. 28, 2014 for Chinese Application No. 2010800048938.0, filed Oct. 27, 2010, 8 pages.
Office Action dated Sep. 30, 2013 for Japanese Application No. 2011-508719 filed May 8, 2009.
Office Action dated Aug. 4, 2014 from EP Patent Application No. 12005299.8, filed May 8, 2009, 5 pages.
Office Action dated Jan. 4, 2017 for Chinese Application No. 201380037371.0, filed May 15, 2013, 28 pages.
Office Action dated Aug. 6, 2013 from Application JP 2011508719, filed May 8, 2009, 7 pages.
Official Communication from the European Patent Office containing a Written Opinion for European Application No. 10774097.9, dated Jan. 30, 2014.
O'Sullivan M P., et al., "Apoptosis in the Airways: Another Balancing Act in the Epithelial Program," American Journal of Respiratory Cell and Molecular Biology, 2003, vol. 29, pp. 3-7.
Ovcharenko., et al., "Endobronchial Use of Low-Frequency Ultrasound and Ultraviolet Laser Radiation in the Complex Treatment of Patients With Suppurative Bronchial Diseases," Problemy Tuberkuleza, 1997, vol. 3, pp. 40-42. (Abstract only).
Overholt., "Glomectomy for Asthma," Diseases of the Chest, 1961, vol. 40, pp. 605-610.
Patent Examination Report dated May 1, 2014 for Australian Patent Application No. 2009244058, filed May 8, 2009, 4 pages.
Pavord I D., et al., "Safety and Efficacy of Bronchial Thermoplasty in Symptomatic, Severe Asthma," American Journal of Respiratory and Critical Care Medicine, 2007, vol. 176, pp. 1185-1191.
PCT International Search Report for Application No. PCT/US00/05412, dated Jun. 20, 2000, 2 pages.
PCT International Search Report for Application No. PCT/US00/18197, dated Oct. 3, 2000, 1 page.
PCT International Search Report for Application No. PCT/US00/28745, dated Mar. 28, 2001, 6 pages.
PCT International Search Report for Application No. PCT/US01/32321, dated Jan. 18, 2002, 2 pages.
PCT International Search Report for Application No. PCT/US98/03759, dated Jul. 30, 1998, 1 page.
PCT International Search Report for Application No. PCT/US98/26227, dated Mar. 25, 1999, 1 page.
PCT International Search Report for Application No. PCT/US99/00232, dated Mar. 4, 1999, 1 page.
PCT International Search Report for Application No. PCT/US99/12986, dated Sep. 29, 1999, 1 page.
Peter K. Jeffery, "Remodeling in Asthma and Chronic Obstructive Lung Disease," American Journal of Respiratory and Critical Care Medicine, 2001, vol. 164 (10), pp. 13516.
Peters, et al., "Tiotropium Bromide Step-Up Therapy for Adults with Uncontrolled Asthma," New England Journal of Medicine, Oct. 28, 2010, vol. 363 (18), pp. 1715-1726.

(56) References Cited

OTHER PUBLICATIONS

Petrou et al., "Bronchoscopic Diathermy Resection and Stent Insertion: a Cost Effective Treatment for Tracheobronchial Obstruction," Thorax, 1993, vol. 48, pp. 1156-1159.
Polosukhin., "Dynamics of the Ultrastructural Changes in Blood and Lymphatic Capillaries of Bronchi in Inflammation and Following Endobronchial Laser Therapy," Virchows Arch, 1997, vol. 431, pp. 283-390.
Polosukhin., "Regeneration of Bronchial Epithelium of Chronic Inflammatory Changes Under Laser Treatment," Pathology, Research and Practice, 1996, vol. 192 (9), pp. 909-918.
Polosukhin., "Ultrastructural Study of the Destructive and Repair Processes in Pulmonary Inflammation and Following Endobronchial Laser Therapy," Virchows Arch, 1999, vol. 435, pp. 13-19.
Polosukhin., "Ultrastructure of the Blood and Lymphatic Capillaries of the Respiratory Tissue During Inflammation and Endobronchial Laser Therapy," Ultrastructural Pathology, 2000, vol. 24, pp. 183-189.
Preliminary Amendment and Response to Restriction Requirement dated Oct. 22, 2012, for U.S. Appl. No. 13/523,223, filed Jun. 14, 2012.
Printout of a Selected List of Reference for Respiratory Development from PubMed Aug. 1999; UNSW Embryo-Respiratory System<http://embryology.med.unsw.edu.au/Refer/respire/select.htm>; 12 pages, printout dated Oct. 12, 2007.
Provotorov V M., et al., "Clinical Efficacy of Treatment of Patients with Non-Specific Pulmonary Diseases by Using Low-Power Laser Irradiation and Performing Intrapulmonary Drug Administration," Terapevichesky Arkhiv, 1991, vol. 62, pp. 18-23.
Raj., "Editorial," Pain Practice, 2004, vol. 4 (1S), pp. S1-S3.
Ramirez et al., "Sympathetomy in Bronchial Asthma," J. A. M. A., 1925, vol. 84 (26), pp. 2002-2003.
Response to Summons to Attend Oral Proceedings dated Jun. 2, 2014 from EP Application No. 10774097.9 filed Oct. 27, 2010, 6 pgs.
Rienhoff., et al., "Treatment of Intractable Bronchial Asthma by Bilateral Resection of the Posterior Pulmonary Plexus," Arch Surg, 1938, vol. 37 (3), pp. 456-469.
Rocha-Singh K J., "Renal Artery Denervation: A Brave New Frontier," Endovascular Today, Feb. 2012, pp. 45-53.
Rubin., et al., "Bronchial Thermoplasty Improves Asthma Status of Moderate to Severe Persistent Asthmatics Over and Above Current Standard-of-Care," American College of Chest Physicians, 2006, 2 pages.
Savchenko., et al., "Adaptation of Regulatory Physiological Systems in Surgical Treatment of Patients with Bronchial Asthma," Klin Med (Mask), 1996, vol. 74 (7), pp. 38-39.
Search Report dated Aug. 27, 2015 for European Application No. 13003665.0 filed May 8, 2009, 4 pages.
Search Report dated Aug. 27, 2015 for European Application No. 13003666.8 filed May 8, 2009, 4 pages.
Search Report dated Aug. 27, 2015 for European Application No. 13003667.6 filed May 8, 2009, 4 pages.
Secondary Office Action dated Mar. 4, 2014 for Japanese Application No. 2011-508719 filed May 8, 2009. 4 pages.
Sengupta., "Part 1 Oral Cavity, Pharynx and Esophagus—Esophageal Sensory Physiology," GI Motility online, 2006, 17 pages.
Seow C Y., et al., "Signal Transduction in Smooth Muscle Historical Perspective on Airway Smooth Muscle: The Saga of a Frustrated Cell," Journal of applied physiology, 2001, vol. 91, pp. 938-952.
Sepulveda., et al., "Treatment of Asthmatic Bronchoconstriction by Percutaneous Low Voltage Vagal Nerve Stimulation: Case Report," Internet Journal of Asthma, Allergy, and Immunology, 2009, vol. 7 (2), 3 pages.
Shaari., et al., "Rhinorrhea is Decreased in Dogs After Nasal Application of Botulinum Toxin," Otolaryngol Head Neck Surgery, 1992, vol. 112 (14), pp. 566-571.
Sheski F D., et al., "Cryotherapy, Electrocautery, and Brachytherapy," Clinics in Chest Medicine, Mar. 1999, vol. 20 (1), pp. 123-138.
Shesterina M V., et al., "Effect of laser therapy on immunity in patients with bronchial asthma and pulmonary tuberculosis," 1993, pp. 23-26.
Shore S A., "Airway Smooth Muscle in Asthma—Not Just More of the Same," The New England Journal of Medicine, 2004, vol. 351 (6), pp. 531-532.
Sil'vestrov., et al., "The Clinico-Pathogenetic Validation and Efficacy of the Use of Low-Energy Laser Irradiation and Glucocorticoids in the Treatment of Bronchial Asthma Patients," Department of Therapy of the Pediatric and Stomatological Faculties of the N.N. Burdenko Voronezh Medical Institute, 7 pages, 1991.
Simonsson., et al., "Role of Autonomic Nervous System and the Cough Reflex in the Increased Responsiveness of Airways in Patients with Obstructive Airway Disease," The Journal of Clinical Investigation, 1967, vol. 46 (11), pp. 1812-1818.
Simpson., et al., "Isolation and Characterization of the botulinum Neurotoxins," Methods Enzymol, 1988, vol. 165, pp. 76-85.
Smakov., "Denervation of the Lung in the Treatment of Bronchial Asthma," Khirurgiia (Mosk), 1982, vol. 9, pp. 117-120.
Smakov., "Pathogenetic Substantiation of Lung Denervation in Bronchial Asthma and it's Indications," Khirurgiia (Mosk), 1999, vol. 2, pp. 67-69.
Smakov., "Prognostication of the Effect of Therapeutic Bronchoscopy in Patients with Bronchial Asthma According to the State of Local Immunity," Klin Med (Mask), 1995, vol. 73 (5), pp. 76-77.
Solway J., et al., "Airway Smooth Muscle as a Target for Asthma Therapy," The New England Journal of Medicine, Mar. 29, 2007, vol. 356 (13), pp. 1367-1369.
Sontag., et al., "Asthmatics with Gastroesophageal Reflux: Long-term Results of a Randomized Trial of Medical and Surgical Antireflux Therapies," The American Journal of Gastroenterology, 2003, vol. 98, pp. 987-999. (Abstract only.).
Examination Report dated Mar. 26, 2018 for EP Application No. 13731525.5, filed May 15, 2013, 8 pages.
Extended European Search Report for Application No. 12005299.8, dated Nov. 7, 2012, 9 pages.
International Preliminary Report on Patentability for Application No. PCT/US2012/058485, dated Apr. 17, 2014, 9 pages.
International Preliminary Report on Patentabilityfor Application No. PCT/US2010/054356, dated May 10, 2012, 15 pages.
International Preliminary Report on PatentabilityNo. PCT/US2010/056424, dated May 24, 2012, 12 pages.
International Search Report and Written Opinion for Application No. PCT/US2009/043393, dated Sep. 21, 2009, 11 pages.
International Search Report and Written Opinion for Application No. PCT/US2012/058485, dated Jan. 3, 2013, 12 pages.
International Search Report and Written Opinion for Application No. PCT/US2010/056424, dated Apr. 14, 2011, 18 pages.
International Search Report and Written Opinion for Application No. PCT/US2010/054356, dated Jun. 16, 2011, 20 pages.
International Search Report and Written Opinion for PCT Application No. PCT/US2013/041189, dated Dec. 4, 2013, 16 pages.
Office Action Sep. 27, 2017 for Chinese Application No. 201380037371.0, filed May 15, 2013, 9 pages.
International Preliminary Report on Patentabilityfor Application No. PCT/US2009/043393, dated Nov. 18, 2010, 9 pages.
Stein., "Possible Mechanisms of Influence of Esophageal Acid on Airway Hyperresponsiveness," The American Journal of Medicine, 2003, vol. 115 (Suppl 3A), pp. 55S-59S. (Abstract only.).
Sterk P J., "Heterogeneity of Airway Hyperresponsiveness: Time for Unconventional, but Traditional Studies," The American Pshychoiogical Society, 2004, pp. 2017-2018.
Summons to Attend Oral Proceedings dated Jul. 14, 2014 for European Application No. EP09743805.5 filed May 8, 2009, 5 pages.
Sundaram., et al., "An Experimental and Theoretical Analysis of Ultrasound-Induced Permeabilization of Cell Membranes," Biophysical Journal, 2003, vol. 84, pp. 3087-3101.
Takino., et al., "Surgical Removal of the Carotid Body and its Relation to the Carotid Chemoreceptor and Baroreceptor Reflex in Asthmatics," Dis Chest, 1965, vol. 47, pp. 129-138.

(56) References Cited

OTHER PUBLICATIONS

Tashkin., et al., "Long-term Treatment Benefits With Tiotropium in COPD Patients With and Without Short-term Bronchodilator Responses," Chest, 2003, vol. 123, pp. 1441-1449.
Third party submission filed on Apr. 2, 2004 in U.S. Appl. No. 14/024,371, 8 pages.
Toma T P., "Brave New World for Interventional Bronchoscopy," Thorax, 2005, vol. 60, pp. 180-181.
Trow T., "Clinical Year in Review I, proceedings of the American Thoracic Society," 2006, vol. 3, pp. 553-556.
Tschumperlin D J., et al., "Chronic Effects of Mechanical Force on Airways," Annual Review of Physiology, 2006, vol. 68, pp. 563-83.
Tschumperlin D J., et al., "Mechanical Stimuli to Airway Remodeling," American Journal of Respiratory and Critical Care Medicine, 2001, vol. 164, pp. S90-S94.
Tsugeno., et al., "A Proton-Pump Inhibitor, Rabeprazole, Improves Ventilatory Function in Patients with Asthma Associated with Gastroesophageal Reflux," Scand J Gastroenterol, 2003, vol. (38), pp. 456-461. (Abstract only).
Tsuji., et al., "Biodegradable Stents as a Platform to Drug Loading," International Journal of Cardiovascular Interventions, 2003, vol. 5, pp. 13-16.
Unal., et al., "Effect of Botulinum Toxin Type A on Nasal Symptoms in Patients with Allergic Rhinitis: A Double-blind, Placebo-controlled Clinical Trial," Acta Oto-Laryngologica, Dec. 2003, vol. 123 (9), pp. 1060-0163.
Urologix, Inc, "Cooled ThermoTherapy.," 2012, retrieved on Mar. 3, 2005 from URL=http://www.urologix.com/clinicians/cooled-thermotherapy.ph- p, 2 pages.
Urologix, Inc, "CTC Advance.TM. Instructions for Use," Targis. RTM. System Manual, 2010, 8 pages.
Vasilotta P. I., et al., "I-R Laser: A New Therapy in Rhino-Sino-Nasal Bronchial Syndrome with Asthmatic Component," American Society for Laser medicine and Surgery abstracts, facsimile copy dated, Feb. 8, 2007, p. 74.
Velden V D., et al., "Autonomic Innervation of Human Airways: Structure, Function, and Pathophysiology in Asthma," Neuroimmunomodulation, 1999, vol. 6, pp. 145-159.
Verhein., et al., "Neural Control of Airway Inflammation," Current Allergy and Asthma Reports, 2009, vol. 9, pp. 484-490.
Vincken., et al., "Improved health outcomes in patients with COPD during 1 yr's treatment with tiotropium," Eur. Respir. J., 2002, vol. 19, pp. 209-216.
Vorotnev., et al., "Treatment of Patients with Chronic Obstructive Bronchitis Using Low Energy Laser at a General Rehabilitation Center," Therapeutic Archive, 1997, vol. 3, pp. 17-19.
Wagner., et al., "Methacholine causes reflex bronchoconstriction," J. Appi. Physiol, 1999, vol. 86, pp. 294-297.
Wahidi., et al., "State of the Art: Interventional Pulmonology," American College of Chest Physicians, Jan. 2007, vol. 131 (1), pp. 261-274.
Weaver, "Electroporation: A General Phenomenon for Manipulating Cells and Tissues," Journal of Cellular Biochemistry, Apr. 1993, vol. 51(4), pp. 426-435.
Wechsler M E., "Bronchial Thermoplasty for Asthma: A Critical Review of a New Therapy," Allergy and Asthma Proceedings, Jul.-Aug. 2008, vol. 29 (4), pp. 1-6.
Wiggs B R., et al., On the Mechanism of Mucosal Folding in Normal and Asthmatic Airways, J. Appl. Physiol, Dec. 1997, vol. 83 (6), pp. 1814-1821.
Wilson K C., et al., "Flexible Bronchoscopy: Indications and contraindications," UptoDate, Nov. 12, 2010 (retrieved Sep. 30, 2012 from www.uptodate.com), 15 pages.
Wilson S R., et al., "Global assessment after bronchial thermoplasty: the patient's perspective," Journal of Outcomes Research, 2006, vol. 10, pp. 37-46.
Wirtz., et al., "Bilateral Lung Transplantation for Severe Persistent and Difficult Asthma," The Journal of Heart and Lung Transplantation, 2005, vol. 24 (10), pp. 1700-1703.
Wizeman., et al., "A Computer Model of Thermal Treatment of Airways by Radiofrequency (RF) Energy Delivery," American Thoracic Society Annual Meeting, 2007, p. 1.
File History for Opposition and Appeal Proceedings for EP2320821, current as of Jun. 15, 2018, 901 pages.
File History for Opposition Proceedings for EP2529686, current as of Jun. 15, 2018, 783 pages.
Office Action dated Nov. 27, 2017, for JP Application No. 2015-014893 filed Jan. 29, 2015, 4 pages.
Office Action dated Feb. 26, 2018, for IN Application No. 8069/DELNP/2010 filed Nov. 16, 2010, 7 pages.
Office Action dated Dec. 22, 2016, for JP Application No. 2015-014893 filed Jan. 29, 2015, 10 pages.
Office Action dated Sep. 25, 2018 for Canadian Application No. 2,723,806, 5 pages.

* cited by examiner

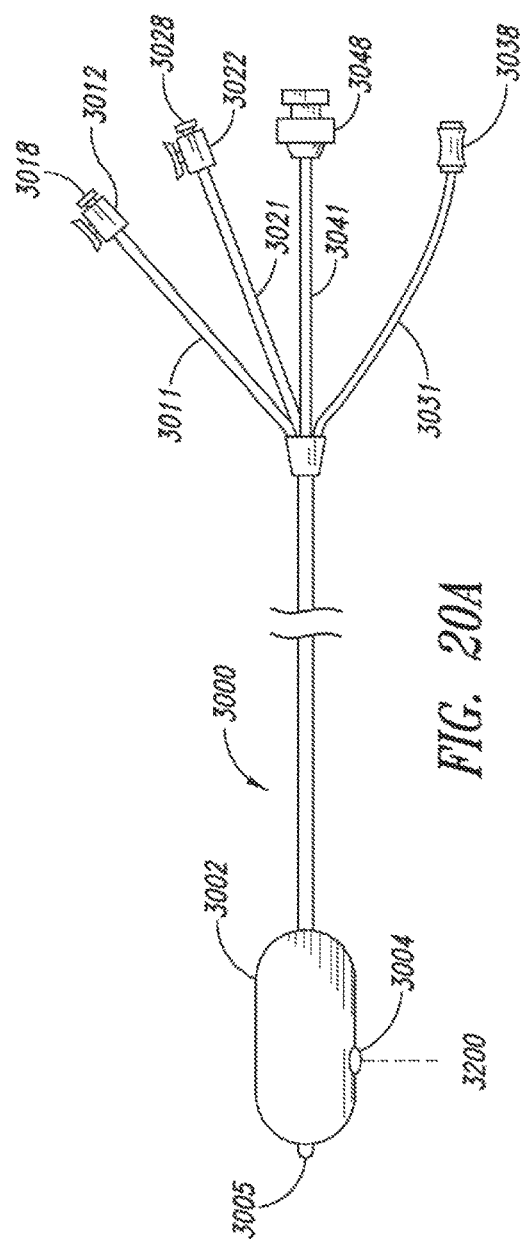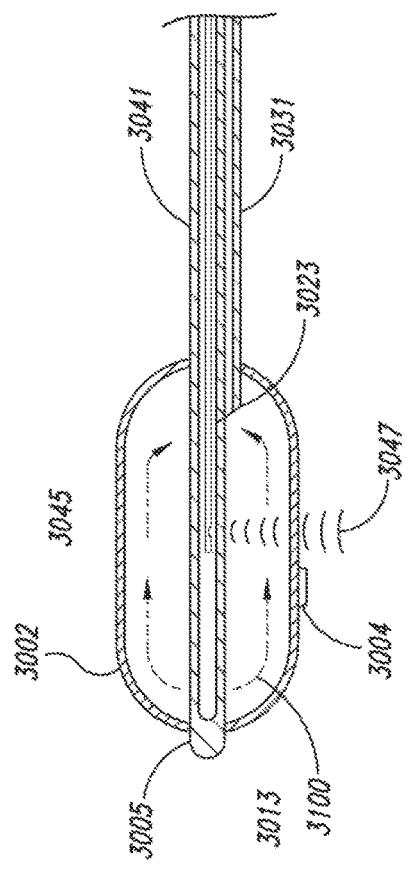

SYSTEMS, ASSEMBLIES, AND METHODS FOR TREATING A BRONCHIAL TREE

CROSS-REFERENCES TO RELATED APPLICATIONS

This application is a continuation of U.S. patent application Ser. No. 13/592,075 filed Aug. 22, 2012, now U.S. Pat. No. 9,668,809 issued Jun. 6, 2017, which is a continuation of U.S. patent application Ser. No. 13/452,664 filed Apr. 20, 2012, now U.S. Pat. No. 8,808,280 issued Aug. 19, 2014, which is a continuation of U.S. patent application Ser. No. 13/245,522 filed Sep. 26, 2011, now U.S. Pat. No. 8,226,638 issued Jul. 24, 2012, which is a continuation of U.S. patent application Ser. No. 12/463,304, filed May 8, 2009, now U.S. Pat. No. 8,088,127 issued Jan. 3, 2012, which claims the benefit under 35 U.S.C. § 119(e) of U.S. Provisional Patent Application No. 61/052,082 filed May 9, 2008; U.S. Provisional Patent Application No. 61/106,490 filed Oct. 17, 2008; and U.S. Provisional Patent Application No. 61/155,449 filed Feb. 25, 2009. Each of these applications is incorporated herein by reference in its entirety.

BACKGROUND

Technical Field

The present invention generally relates to systems, assemblies, and methods for treating a bronchial tree, and more particularly, the invention relates to systems, assemblies, and methods for eliciting a desired response.

Description of the Related Art

Pulmonary diseases may cause a wide range of problems that adversely affect performance of the lungs. Pulmonary diseases, such as asthma and chronic obstructive pulmonary disease ("COPD"), may lead to increased airflow resistance in the lungs. Mortality, health-related costs, and the size of the population having adverse effects due to pulmonary diseases are all substantial. These diseases often adversely affect quality of life. Symptoms are varied but often include cough; breathlessness; and wheeze. In COPD, for example, breathlessness may be noticed when performing somewhat strenuous activities, such as running, jogging, brisk walking, etc. As the disease progresses, breathlessness may be noticed when performing non-strenuous activities, such as walking. Over time, symptoms of COPD may occur with less and less effort until they are present all of the time, thereby severely limiting a person's ability to accomplish normal tasks.

Pulmonary diseases are often characterized by airway obstruction associated with blockage of an airway lumen, thickening of an airway wall, alteration of structures within or around the airway wall, or combinations thereof. Airway obstruction can significantly decrease the amount of gas exchanged in the lungs resulting in breathlessness. Blockage of an airway lumen can be caused by excessive intraluminal mucus or edema fluid, or both. Thickening of the airway wall may be attributable to excessive contraction of the airway smooth muscle, airway smooth muscle hypertrophy, mucous glands hypertrophy, inflammation, edema, or combinations thereof. Alteration of structures around the airway, such as destruction of the lung tissue itself, can lead to a loss of radial traction on the airway wall and subsequent narrowing of the airway.

Asthma can be characterized by contraction of airway smooth muscle, smooth muscle hypertrophy, excessive mucus production, mucous gland hypertrophy, and/or inflammation and swelling of airways. These abnormalities are the result of a complex interplay of local inflammatory cytokines (chemicals released locally by immune cells located in or near the airway wall), inhaled irritants (e.g., cold air, smoke, allergens, or other chemicals), systemic hormones (chemicals in the blood such as the anti-inflammatory cortisol and the stimulant epinephrine), local nervous system input (nerve cells contained completely within the airway wall that can produce local reflex stimulation of smooth muscle cells and mucous glands), and the central nervous system input (nervous system signals from the brain to smooth muscle cells and mucous glands carried through the vagus nerve). These conditions often cause widespread temporary tissue alterations and initially reversible airflow obstruction that may ultimately lead to permanent tissue alteration and permanent airflow obstruction that make it difficult for the asthma sufferer to breathe. Asthma can further include acute episodes or attacks of additional airway narrowing via contraction of hyper-responsive airway smooth muscle that significantly increases airflow resistance. Asthma symptoms include recurrent episodes of breathlessness (e.g., shortness of breath or dyspnea), wheezing, chest tightness, and cough.

Emphysema is a type of COPD often characterized by the alteration of lung tissue surrounding or adjacent to the airways in the lungs. Emphysema can involve destruction of lung tissue (e.g., alveoli tissue such as the alveolar sacs) that leads to reduced gas exchange and reduced radial traction applied to the airway wall by the surrounding lung tissue. The destruction of alveoli tissue leaves areas of emphysematous lung with overly large airspaces that are devoid of alveolar walls and alveolar capillaries and are thereby ineffective at gas exchange. Air becomes "trapped" in these larger airspaces. This "trapped" air may cause over-inflation of the lung, and in the confines of the chest restricts the in-flow of oxygen rich air and the proper function of healthier tissue. This results in significant breathlessness and may lead to low oxygen levels and high carbon dioxide levels in the blood. This type of lung tissue destruction occurs as part of the normal aging process, even in healthy individuals. Unfortunately, exposure to chemicals or other substances (e.g., tobacco smoke) may significantly accelerate the rate of tissue damage or destruction. Breathlessness may be further increased by airway obstruction. The reduction of radial traction may cause the airway walls to become "floppy" such that the airway walls partially or fully collapse during exhalation. An individual with emphysema may be unable deliver air out of their lungs due to this airway collapse and airway obstructions during exhalation.

Chronic bronchitis is a type of COPD that can be characterized by contraction of the airway smooth muscle, smooth muscle hypertrophy, excessive mucus production, mucous gland hypertrophy, and inflammation of airway walls. Like asthma, these abnormalities are the result of a complex interplay of local inflammatory cytokines, inhaled irritants, systemic hormones, local nervous system, and the central nervous system. Unlike asthma where respiratory obstruction may be largely reversible, the airway obstruction in chronic bronchitis is primarily chronic and permanent. It is often difficult for a chronic bronchitis sufferer to breathe because of chronic symptoms of shortness of breath, wheezing, and chest tightness, as well as a mucus producing cough.

Different techniques can be used to assess the severity and progression of pulmonary diseases. For example, pulmonary function tests, exercise capacity, and quality of life questionnaires are often used to evaluate subjects. Pulmonary function tests involve objective and reproducible measures of basic physiologic lung parameters, such as total airflow, lung volume, and gas exchange. Indices of pulmonary function tests used for the assessment of obstructive pulmonary diseases include the forced expiratory volume in 1 second (FEV1), the forced vital capacity (FVC), the ratio of the FEV1 to FVC, the total lung capacity (TLC), airway resistance and the testing of arterial blood gases. The FEV1 is the volume of air a patient can exhale during the first second of a forceful exhalation which starts with the lungs completely filled with air. The FEV1 is also the average flow that occurs during the first second of a forceful exhalation. This parameter may be used to evaluate and determine the presence and impact of any airway obstruction. The FVC is the total volume of air a patient can exhale during a forceful exhalation that starts with the lungs completely filled with air. The FEV1/FVC is the fraction of all the air that can be exhaled during a forceful exhalation during the first second. An FEV1/FVC ratio less than 0.7 after the administration of at least one bronchodilator defines the presence of COPD. The TLC is the total amount of air within the lungs when the lungs are completely filled and may increase when air becomes trapped within the lungs of patients with obstructive lung disease. Airway resistance is defined as the pressure gradient between the alveoli and the mouth to the rate of air flow between the alveoli and the mouth. Similarly, resistance of a given airway would be defined as the ratio of the pressure gradient across the given airway to the flow through the airway. Arterial blood gases tests measure the amount of oxygen and the amount of carbon dioxide in the blood and are the most direct method for assessing the ability of the lungs and respiratory system to bring oxygen from the air into the blood and to get carbon dioxide from the blood out of the body.

Exercise capacity tests are objective and reproducible measures of a patient's ability to perform activities. A six minute walk test (6MWT) is an exercise capacity test in which a patient walks as far as possible over a flat surface in 6 minutes. Another exercise capacity test involves measuring the maximum exercise capacity of a patient. For example, a physician can measure the amount of power the patient can produce while on a cycle ergometer. The patient can breathe 30 percent oxygen and the work load can increase by 5-10 watts every 3 minutes.

Quality of life questionnaires assess a patient's overall health and well being. The St. George's Respiratory Questionnaire is a quality of life questionnaire that includes 75 questions designed to measure the impact of obstructive lung disease on overall health, daily life, and perceived well-being. The efficacy of a treatment for pulmonary diseases can be evaluated using pulmonary function tests, exercise capacity tests, and/or questionnaires. A treatment program can be modified based on the results from these tests and/or questionnaires.

Treatments, such as bronchial thermoplasty, involve destroying smooth muscle tone by ablating the airway wall in a multitude of bronchial branches within the lung thereby eliminating both smooth muscles and nerves in the airway walls of the lung. The treated airways are unable to respond favorably to inhaled irritants, systemic hormones, and both local and central nervous system input. Unfortunately, this destruction of smooth muscle tone and nerves in the airway wall may therefore adversely affect lung performance. For example, inhaled irritants, such as smoke or other noxious substances, normally stimulate lung irritant receptors to produce coughing and contracting of airway smooth muscle. Elimination of nerves in the airway walls removes both local nerve function and central nervous input, thereby eliminating the lung's ability to expel noxious substances with a forceful cough. Elimination of airway smooth muscle tone may eliminate the airways' ability to constrict, thereby allowing deeper penetration of unwanted substances, such as noxious substances, into the lung.

Additionally, methods of destroying smooth muscle tone by ablating portions of the airway wall, such as bronchial thermoplasty, often have the following limitations: 1) inability to affect airways that are not directly ablated, typically airways smaller than approximately 3.0 mm which may also be narrowed in obstructive lung diseases such as asthma, emphysema, and chronic bronchitis; 2) short-term swelling that causes acute respiratory problems due to perioperative swelling in airways already narrowed by obstructive lung disease effects; 3) hundreds of applications to airways within the lungs may be required to alter overall lung functionality; 4) since multiple generations of airways within the lung are treated (typically generations 2-8), targeting lung airways without missing or over treating specific lung airway sections can be problematic; and, 5) separating the treating step into stages may be required to reduce the healing load on the lung which adds additional risk and cost with each additional bronchoscopy treatment session.

Both asthma and COPD are serious diseases with growing numbers of sufferers. Current management techniques, which include prescription drugs, are neither completely successful nor free from side effects. Additionally, many patients do not comply with their drug prescription dosage regiment. Accordingly, it would be desirable to provide a treatment which improves resistance to airflow without the need for patient compliance.

BRIEF SUMMARY

In some embodiments, a treatment system can be navigated through airways, such as the right and left main bronchi of the lung root as well as more distal airways within the lungs, to treat a wide range of pulmonary symptoms, conditions, and/or diseases, including, without limitation, asthma, COPD, obstructive lung diseases, or other diseases that lead to an increased resistance to airflow in the lungs. The treatment system can treat one or more target sites without treating non-targeted sites. Even if targeted anatomical features (e.g., nerves, glands, membranes, and the like) of main bronchi, lobar bronchi, segmental bronchi or subsegmental bronchi are treated, non-targeted anatomical features can be substantially unaltered. For example, the treatment system can destroy nerve tissue at target sites without destroying to any significant extent non-targeted tissue that can remain functional after performing treatment.

At least some embodiments disclosed herein can be used to affect nerve tissue of nerve trunks outside of airway walls while maintaining the airways ability to move (e.g., constrict and/or expand) in response to, for example, inhaled irritants, local nerve stimulation, systemic hormones, or combinations thereof. In some embodiments, the nerve tissue of nerve trunks is destroyed without eliminating smooth muscle tone. After damaging the nerve trunks, the airways have at least some muscle tone such that the smooth muscles in the airways, if stimulated, can alter the diameter of the airway to help maintain proper lung function. A wide range of different physiological functions associated with smooth muscle tone can be maintained before, during, and/or after the treatment.

In some embodiments, a method for treating one or more pulmonary diseases is provided. The method includes damaging nerve tissue of a vagal nerve trunk extending along the outside of a bronchial tree airway so as to attenuate nervous system signals transmitted to a portion of the bronchial tree. The nerve trunk may be the main stem of a nerve, comprising a bundle of nerve fibers bound together by a tough sheath of connective tissue. In some embodiments, the nerve tissue is damaged while maintaining a functionality of one or more anatomical features, such as blood vessels, also extending alongside the airway so as to preserve a respiratory function of the portion of the bronchial tree after the nerve tissue is damaged.

Conditions and symptoms associated with pulmonary diseases can be reduced, limited, or substantially eliminated. For example, airway obstruction can be treated to elicit reduced airflow resistance. Blood vessels or other tissue can remain intact and functional during and/or after treatment. The respiratory function that is preserved can include gas exchange, mucociliary transport, and the like. In some embodiments, the nerve tissue, such as nerve tissue of nerve trunks located outside of the airway, is damaged without damaging to any significant extent a portion of the airway wall that is circumferentially adjacent to the damaged nerve tissue. Accordingly, non-targeted tissue can be substantially unaltered by the damage to the airway nerve tissue.

Damaging the nerve tissue can involve delivering energy to the nerve tissue such that the destroyed nerve tissue impedes or stops the transmission of nervous system signals to nerves more distal along the bronchial tree. The nerve tissue can be temporarily or permanently damaged by delivering different types of energy to the nerve tissue. For example, the nerve tissue can be thermally damaged by increasing a temperature of the nerve tissue to a first temperature (e.g., an ablation temperature) while the wall of the airway is at a second temperature that is less than the first temperature. In some embodiments, a portion of the airway wall positioned radially inward from the nerve tissue can be at the first temperature so as to prevent permanent damage to the portion of the airway wall. The first temperature can be sufficiently high to cause permanent destruction of the nerve tissue. In some embodiments, the nerve tissue is part of a nerve trunk located in connective tissue outside of the airway wall. The smooth muscle and nerve tissue in the airway wall can remain functional to maintain a desired level of smooth muscle tone. The airway can constrict/dilate in response to stimulation (e.g., stimulation caused by inhaled irritants, the local nervous system, or systemic hormones). In other embodiments, the nerve tissue is part of a nerve branch or nerve fibers in the airway wall. In yet other embodiments, both nerve tissue of the nerve trunk and nerve tissue of nerve branches/fibers are simultaneously or sequentially damaged. Various types of activatable elements, such as ablation elements, can be utilized to output the energy.

In some embodiments, a method for treating a subject comprises moving an elongate assembly along a lumen of an airway of a bronchial tree. The airway includes a first tubular section, a second tubular section, a treatment site between the first tubular section and the second tubular section, and a nerve extending along at least the first tubular section, the treatment site, and the second tubular section. The nerve can be within or outside of the airway wall. In some embodiments, the nerve is a nerve trunk outside of the airway wall and connected to a vagus nerve.

The method can further include damaging a portion of the nerve at the treatment site to substantially prevent signals from traveling between the first tubular section and the second tubular section via the nerve. In some embodiments, blood flow between the first tubular section and the second tubular section can be maintained while damaging a portion of the nerve. The continuous blood flow can maintain desired functioning of distal lung tissue.

The second tubular section of the airway may dilate in response to the damage to the nerve. Because nervous system signals are not delivered to smooth muscle of the airway of the second tubular section, smooth muscle can relax so as to cause dilation of the airway, thereby reducing airflow resistance, even airflow resistance associated with pulmonary diseases. In some embodiments, nerve tissue can be damaged to cause dilation of substantially all the airways distal to the damaged tissue. The nerve can be a nerve trunk, nerve branch, nerve fibers, and/or other accessible nerves.

The method, in some embodiments, includes detecting one or one attributes of an airway and evaluating whether the nerve tissue is damaged based on the attributes. Evaluating includes comparing measured attributes of the airway (e.g., comparing measurements taken at different times), comparing measured attributes and stored values (e.g., reference values), calculating values based on measured attributes, monitoring changes of attributes, combinations thereof, or the like.

In some embodiments, a method for treating a subject includes moving an intraluminal device along a lumen of an airway of a bronchial tree. A portion of the airway is denervated using the intraluminal device. In some embodiments, the portion of the airway is denervated without irreversibly damaging to any significant extent an inner surface of the airway. In some embodiments, a portion of a bronchial tree is denervated without irreversibly damaging to any significant extent nerve tissue (e.g., nerve tissue of nerve fibers) within the airway walls of the bronchial tree. The inner surface can define the lumen along which the intraluminal device was moved.

The denervating process can be performed without destroying at least one artery extending along the airway. In some embodiments, substantially all of the arteries extending along the airway are preserved during the denervating process. In some embodiments, one or more nerves embedded in the wall of the airway can be generally undamaged during the denervating process. The destroyed nerves can be nerve trunks outside of the airway.

In some embodiments, the denervating process can decrease smooth muscle tone of the airway to achieve a desired increased airflow into and out of the lung. In some embodiments, the denerving process causes a sufficient decrease of smooth muscle tone so as to substantially increase airflow into and out of the lung. For example, the subject may have an increase in FEV1 of at least 10% over a baseline FEV1. As such, the subject may experience significant improved lung function when performing normal everyday activities, even strenuous activities. In some embodiments, the decrease of airway smooth muscle tone is sufficient to cause an increase of FEV1 in the range of about 10% to about 30%. Any number of treatment sites can be treated either in the main bronchi, segmental bronchi or subsegmental bronchi to achieve the desired increase in lung function.

In some embodiments, an elongate assembly for treating a lung is adapted to damage nerve tissue of a nerve trunk so as to attenuate nervous system signals transmitted to a more distal portion of the bronchial tree. The tissue can be damaged while the elongated assembly extends along a lumen of the bronchial tree. A delivery assembly can be used to provide access to the nerve tissue.

In some other embodiments, a system for treating a subject includes an elongate assembly dimensioned to move along a lumen of an airway of a bronchial tree. The elongate assembly is adapted to attenuate signals transmitted by nerve tissue, such as nerve tissue of nerve trunks, while not irreversibly damaging to any significant extent an inner surface of the airway. The elongate assembly can include an embeddable distal tip having at least one actuatable element, such as an ablation element. The ablation element can ablate various types of nerve tissue when activated. In some embodiments, the ablation element includes one or more electrodes operable to output radiofrequency energy.

In some embodiments, a method comprises damaging nerve tissue of a first main bronchus to substantially prevent nervous system signals from traveling to substantially all distal bronchial branches connected to the first main bronchus. In some embodiments, most or all of the bronchial branches distal to the first main bronchus are treated. The nerve tissue, in certain embodiments, is positioned between a trachea and a lung through which the bronchial branches extend. The method further includes damaging nerve tissue of a second main bronchus to substantially prevent nervous system signals from traveling to substantially all distal bronchial branches connected to the second main bronchus. A catheter assembly can be used to damage the nerve tissue of the first main bronchus and to damage the nerve tissue of the second main bronchus without removing the catheter assembly from a trachea connected to the first and second bronchi.

In some embodiments, a method comprises denervating most of a portion of a bronchial tree to substantially prevent nervous system signals from traveling to substantially all bronchial branches of the portion. In certain embodiments, denervating procedures involve damaging nerve tissue using less than about 100 applications of energy, 50 applications of energy, 36 applications of energy, 18 applications of energy, 10 applications of energy, or 3 applications of energy. Each application of energy can be at a different treatment site. In some embodiments, substantially all bronchial branches in one or both lungs are denervated by the application of energy.

In certain embodiments, one or more detection elements are used to detect attributes of airways before, during, and/or after therapy. A detection element can physically contact an inner surface of the airway to evaluate physical properties of the airway. The detection element may include one or more inflatable balloons that can be positioned distal to targeted tissue.

BRIEF DESCRIPTION OF THE SEVERAL VIEWS OF THE DRAWINGS

In the Figures, identical reference numbers identify similar elements or acts.

FIG. 20A is a side elevational view of a treatment system having an expandable assembly, in accordance with another embodiment.

FIG. 20B is a cross-sectional view of the expandable assembly of FIG. 20A.

DETAILED DESCRIPTION

In the following description, certain specific details are set forth in order to provide a thorough understanding of various embodiments of the invention. However, one skilled in the art will understand that the invention may be practiced without these details. In other instances, well-known structures associated with catheter systems, delivery assemblies, activatable elements, circuitry, and electrodes have not been described in detail to avoid unnecessarily obscuring descriptions of the embodiments of the invention.

Unless the context requires otherwise, throughout the specification and claims which follow, the word "comprise" and variations thereof, such as "comprises" and "comprising" are to be construed in an open, inclusive sense, that is, as "including but not limited to."

Figure 1:
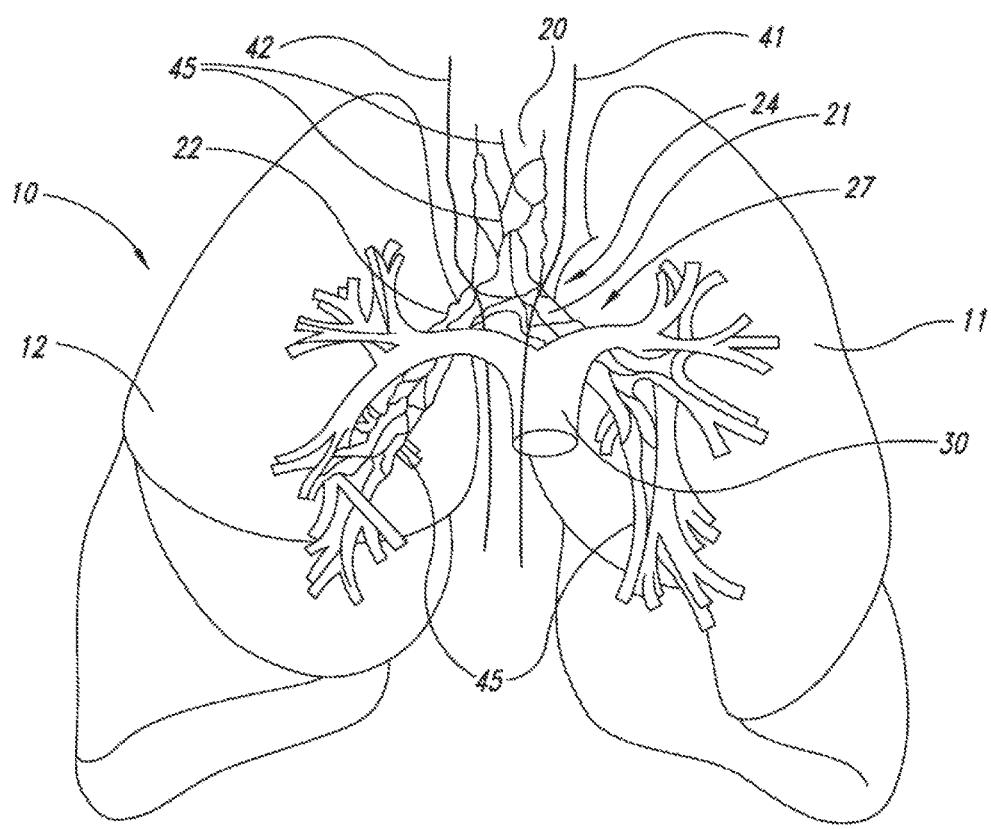
FIG. 1 is an illustration of lungs, blood vessels, and nerves near to and in the lungs.

FIG. 1 illustrates human lungs 10 having a left lung 11 and a right lung 12. A trachea 20 extends downwardly from the nose and mouth and divides into a left main bronchus 21 and a right main bronchus 22. The left main bronchus 21 and right main bronchus 22 each branch to form a lobar, segmental bronchi, and sub-segmental bronchi, which have successively smaller diameters and shorter lengths in the outward direction (i.e., the distal direction). A main pulmonary artery 30 originates at a right ventricle of the heart and passes in front of a lung root 24. At the lung root 24, the artery 30 branches into a left and right pulmonary artery, which in turn branch to form a network of branching blood vessels. These blood vessels can extend alongside airways of a bronchial tree 27. The bronchial tree 27 includes the left main bronchus 21, the right main bronchus 22, bronchioles, and alveoli. Vagus nerves 41, 42 extend alongside the trachea 20 and branch to form nerve trunks 45.

The left and right vagus nerves 41, 42 originate in the brainstem, pass through the neck, and descend through the chest on either side of the trachea 20. The vagus nerves 41, 42 spread out into nerve trunks 45 that include the anterior and posterior pulmonary plexuses that wrap around the trachea 20, the left main bronchus 21, and the right main bronchus 22. The nerve trunks 45 also extend along and outside of the branching airways of the bronchial tree 27. Nerve trunks 45 are the main stem of a nerve, comprising a bundle of nerve fibers bound together by a tough sheath of connective tissue.

The prime function of the lungs 10 is to exchange oxygen from air into the blood and to exchange carbon dioxide from the blood to the air. The process of gas exchange begins when oxygen rich air is pulled into the lungs 10. Contraction of the diaphragm and intercostal chest wall muscles cooperate to decrease the pressure within the chest to cause the oxygen rich air to flow through the airways of the lungs 10. For example, air passes through the mouth and nose, the trachea 20, then through the bronchial tree 27. The air is ultimately delivered to the alveolar air sacs for the gas exchange process.

Oxygen poor blood is pumped from the right side of the heart through the pulmonary artery 30 and is ultimately delivered to alveolar capillaries. This oxygen poor blood is rich in carbon dioxide waste. Thin semi-permeable membranes separate the oxygen poor blood in capillaries from the oxygen rich air in the alveoli. These capillaries wrap around and extend between the alveoli. Oxygen from the air diffuses through the membranes into the blood, and carbon dioxide from the blood diffuses through the membranes to the air in the alveoli. The newly oxygen enriched blood then flows from the alveolar capillaries through the branching blood vessels of the pulmonary venous system to the heart. The heart pumps the oxygen rich blood throughout the body. The oxygen spent air in the lung is exhaled when the diaphragm and intercostal muscles relax and the lungs and chest wall elastically return to the normal relaxed states. In this manner, air can flow through the branching bronchioles, the bronchi 21, 22, and the trachea 20 and is ultimately expelled through the mouth and nose.

Figure 2A:
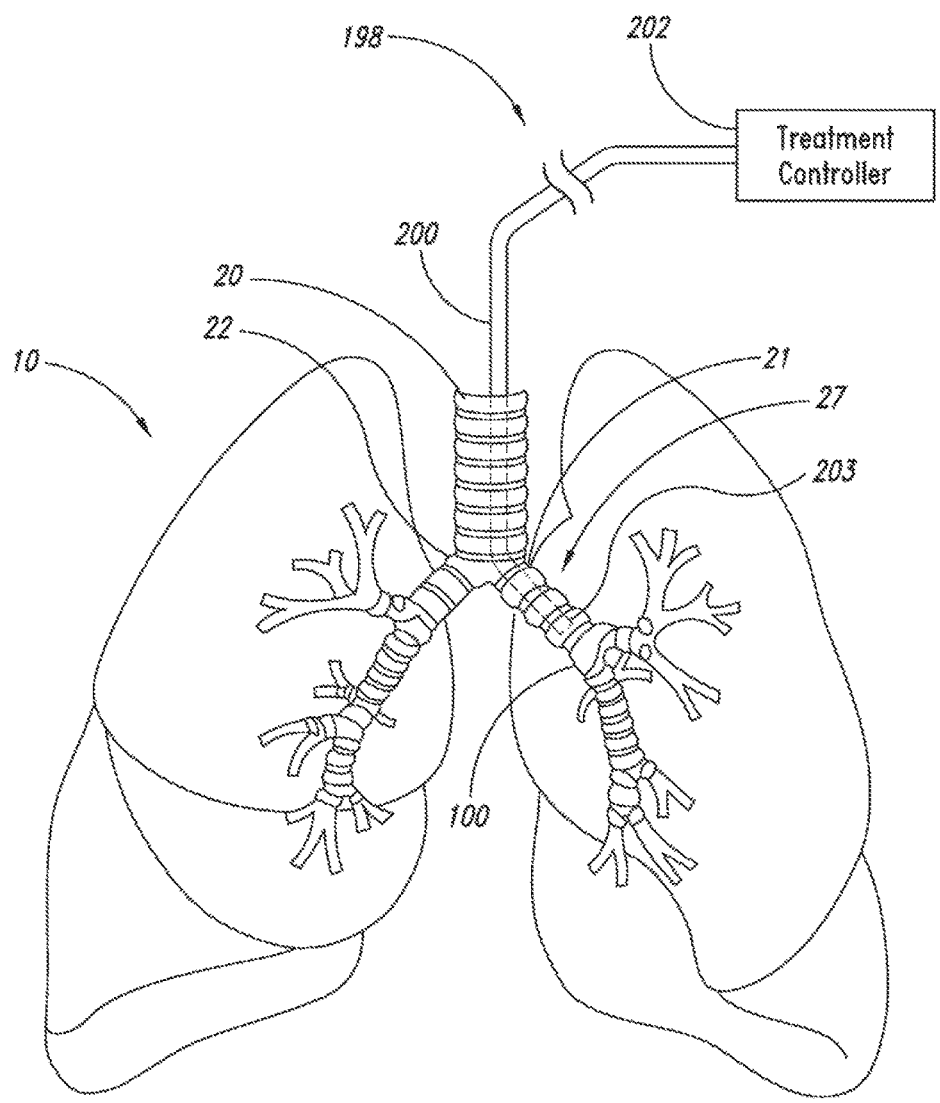
FIG. 2A is a schematic view of a treatment system positioned within a left main bronchus according to one embodiment.

A treatment system 198 of FIG. 2A can be used to treat the lungs 10 to adjust air flow during expiration or inhalation, or both. For example, airways can be enlarged (e.g., dilated) to decrease air flow resistance to increase gas exchange. The treatment system 198 can affect nerve tissue, such as nerve tissue of a nerve trunk, to dilate airways.

In some embodiments, the treatment system 198 targets the nervous system which provides communication between the brain and the lungs 10 using electrical and chemical signals. A network of nerve tissue of the autonomic nervous system senses and regulates activity of the respiratory system and the vasculature system. Nerve tissue includes fibers that use chemical and electrical signals to transmit sensory and motor information from one body part to another. For example, the nerve tissue can transmit motor information in the form of nervous system input, such as a signal that causes contraction of muscles or other responses. The fibers can be made up of neurons. The nerve tissue can be surrounded by connective tissue, i.e., epineurium. The autonomic nervous system includes a sympathetic system and a parasympathetic system. The sympathetic nervous system is largely involved in "excitatory" functions during periods of stress. The parasympathetic nervous system is largely involved in "vegetative" functions during periods of energy conservation. The sympathetic and parasympathetic nervous systems are simultaneously active and generally have reciprocal effects on organ systems. While innervation of the blood vessels originates from both systems, innervation of the airways are largely parasympathetic in nature and travel between the lung and the brain in the right vagus nerve 42 and the left vagus nerve 41.

The treatment system 198 can perform any number of procedures on one or more of these nerve trunks 45 to affect the portion of the lung associated with those nerve trunks. Because some of the nerve tissue in the network of nerve trunks 45 coalesce into other nerves (e.g., nerves connected to the esophagus, nerves though the chest and into the abdomen, and the like), the treatment system 198 can treat specific sites to minimize, limit, or substantially eliminate unwanted damage of those other nerves. Some fibers of anterior and posterior pulmonary plexuses coalesce into small nerve trunks which extend along the outer surfaces of the trachea 20 and the branching bronchi and bronchioles as they travel outward into the lungs 10. Along the branching bronchi, these small nerve trunks continually ramify with each other and send fibers into the walls of the airways, as discussed in connection with FIGS. 3 and 4.

The treatment system 198 can affect specific nerve tissue, such as vagus nerve tissue, associated with particular sites of interest. Vagus nerve tissue includes efferent fibers and afferent fibers oriented parallel to one another within a nerve branch. The efferent nerve tissue transmits signals from the brain to airway effector cells, mostly airway smooth muscle cells and mucus producing cells. The afferent nerve tissue transmits signals from airway sensory receptors, which respond variously to irritants and stretch, to the brain. While efferent nerve tissue innervates smooth muscle cells all the way from the trachea 20 to the terminal bronchioles, the afferent fiber innervation is largely limited to the trachea 20 and larger bronchi. There is a constant, baseline tonic activity of the efferent vagus nerve tissues to the airways which causes a baseline level of smooth muscle contraction and mucous secretion.

The treatment system 198 can affect the efferent and/or the afferent tissues to control airway smooth muscle (e.g., innervate smooth muscle) and mucous secretion. The contraction of airway smooth muscle and excess mucous secretion associated with pulmonary diseases often results in relatively high air flow resistance causing reduced gas exchange and decreased lung performance.

For example, the treatment system 198 can attenuate the transmission of signals traveling along the vagus nerves 41, 42 that cause muscle contractions, mucus production, and the like. Attenuation can include, without limitation, hindering, limiting, blocking, and/or interrupting the transmission of signals. For example, the attenuation can include decreasing signal amplitude of nerve signals or weakening the transmission of nerve signals. Decreasing or stopping nervous system input to distal airways can alter airway smooth muscle tone, airway mucus production, airway inflammation, and the like, thereby controlling airflow into and out of the lungs 10. In some embodiments, the nervous system input can be decreased to correspondingly decrease airway smooth muscle tone. In some embodiments, the airway mucus production can be decreased a sufficient amount to cause a substantial decrease in coughing and/or in airflow resistance. Signal attenuation may allow the smooth muscles to relax and prevent, limit, or substantially eliminate mucus production by mucous producing cells. In this manner, healthy and/or diseased airways can be altered to adjust lung function. After treatment, various types of questionnaires or tests can be used to assess the subject's response to the treatment. If needed or desired, additional procedures can be performed to reduce the frequency of coughing, decrease breathlessness, decrease wheezing, and the like.

Main bronchi 21, 22 (i.e., airway generation 1) of FIG. 1 can be treated to affect distal portions of the bronchial tree 27. In some embodiments, the left and right main bronchi 21, 22 are treated at locations along the left and right lung roots 24 and outside of the left and right lungs 11, 12. Treatment sites can be distal to where vagus nerve branches connect to the trachea and the main bronchi 21, 22 and proximal to the lungs 11, 12. A single treatment session involving two therapy applications can be used to treat most of or the entire bronchial tree 27. Substantially all of the bronchial branches extending into the lungs 11, 12 may be affected to provide a high level of therapeutic effectiveness. Because the bronchial arteries in the main bronchi 21, 22 have relatively large diameters and high heat sinking capacities, the bronchial arteries may be protected from unintended damage due to the treatment.

In some embodiments, one of the left and right main bronchi 21, 22 is treated to treat one side of the bronchial tree 27. The other main bronchus 21, 22 can be treated based on the effectiveness of the first treatment. For example, the left main bronchus 21 can be treated to treat the left lung 11. The right main bronchus 22 can be treated to treat the right lung 12. In some embodiments, a single treatment system can damage the nerve tissue of one of the bronchi 21, 22 and can damage the nerve tissue of the other main bronchus 21, 22 without removing the treatment system from the trachea 20. Nerve tissue positioned along the main bronchi 21, 22 can thus be damaged without removing the treatment system from the trachea 20. In some embodiments, a single procedure can be performed to conveniently treat substantially all, or at least a significant portion (e.g., at least 50%, 70%, 80%, 90% of the bronchial airways), of the patient's bronchial tree. In other procedures, the treatment system can be removed from the patient after treating one of the lungs 11, 12. If needed, the other lung 11, 12 can be treated in a subsequent procedure.

Figure 2B:
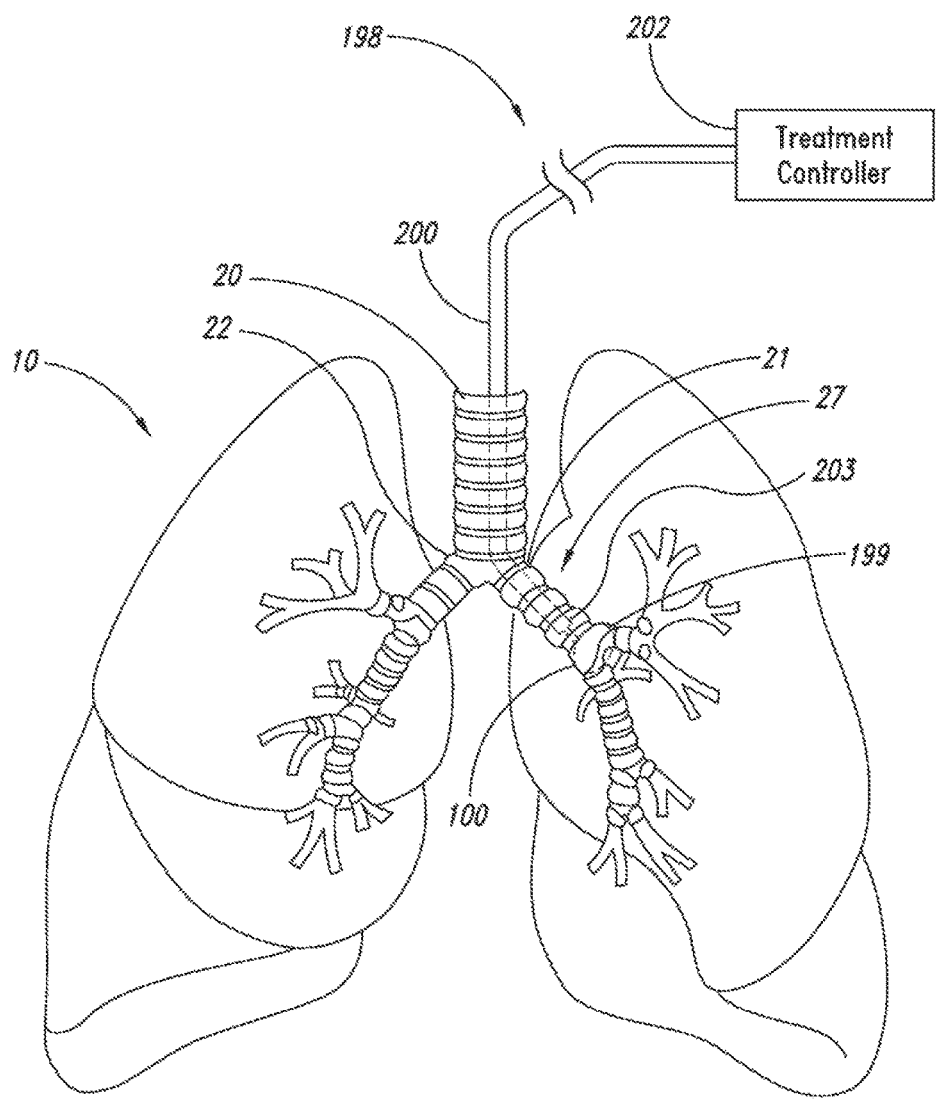
FIG. 2B is a schematic view of a treatment system and an instrument extending distally from the treatment system.

The treatment system 198 of FIGS. 2A and 2B can treat airways that are distal to the main bronchi 21, 22. For example, the treatment system 198 can be positioned in higher generation airways (e.g., airway generations >2) to affect remote distal portions of the bronchial tree 27. The treatment system 198 can be navigated through tortuous airways to perform a wide range of different procedures, such as, for example, denervation of a portion of a lobe, an entire lobe, multiple lobes, or one lung or both lungs. In some embodiments, the lobar bronchi are treated to denervate lung lobes. For example, one or more treatment sites along a lobar bronchus may be targeted to denervate an entire lobe connected to that lobar bronchus. Left lobar bronchi can be treated to affect the left superior lobe and/or the left inferior lobe. Right lobar bronchi can be treated to affect the right superior lobe, the right middle lobe, and/or the right inferior lobe. Lobes can be treated concurrently or sequentially. In some embodiments, a physician can treat one lobe. Based on the effectiveness of the treatment, the physician can concurrently or sequentially treat additional lobe(s). In this manner, different isolated regions of the bronchial tree can be treated.

The treatment system 198 can also be used in segmental or subsegmental bronchi. Each segmental bronchus may be treated by delivering energy to a single treatment site along each segmental bronchus. For example, energy can be delivered to each segmental bronchus of the right lung. In some procedures, ten applications of energy can treat most of or substantially all of the right lung. In some procedures, most or substantially all of both lungs are treated using less than thirty-six different applications of energy. Depending on the anatomical structure of the bronchial tree, segmental bronchi can often be denervated using one or two applications of energy.

The treatment system 198 can affect nerve tissue while maintaining function of other tissue or anatomical features, such as the mucous glands, cilia, smooth muscle, body vessels (e.g., blood vessels), and the like. Nerve tissue includes nerve cells, nerve fibers, dendrites, and supporting tissue, such as neuroglia. Nerve cells transmit electrical impulses, and nerve fibers are prolonged axons that conduct the impulses. The electrical impulses are converted to chemical signals to communicate with effector cells or other nerve cells. By way of example, the treatment system 198 is capable of denervating a portion of an airway of the bronchial tree 27 to attenuate one or more nervous system signals transmitted by nerve tissue. Denervating can include damaging all of the nerve tissue of a section of a nerve trunk along an airway to stop substantially all of the signals from traveling through the damaged section of the nerve trunk to more distal locations along the bronchial tree. If a plurality of nerve trunks extends along the airway, each nerve trunk can be damaged. As such, the nerve supply along a section of the bronchial tree can be cut off. When the signals are cut off, the distal airway smooth muscle can relax leading to airway dilation. This airway dilation reduces airflow resistance so as to increase gas exchange in the lungs 10, thereby reducing, limiting, or substantially eliminating one or more symptoms, such as breathlessness, wheezing, chest tightness, and the like. Tissue surrounding or adjacent to the targeted nerve tissue may be affected but not permanently damaged. In some embodiments, for example, the bronchial blood vessels along the treated airway can deliver a similar amount of blood to bronchial wall tissues and the pulmonary blood vessels along the treated airway can deliver a similar amount of blood to the alveolar sacs at the distal regions of the bronchial tree 27 before and after treatment. These blood vessels can continue to transport blood to maintain sufficient gas exchange. In some embodiments, airway smooth muscle is not damaged to a significant extent. For example, a relatively small section of smooth muscle in an airway wall which does not appreciably impact respiratory function may be reversibly altered. If energy is used to destroy the nerve tissue outside of the airways, a therapeutically effective amount of energy does not reach a significant portion of the non-targeted smooth muscle tissue.

The treatment system 198 of FIG. 2A includes a treatment controller 202 and an intraluminal elongate assembly 200 connected to the controller 202. The elongate assembly 200 can be inserted into the trachea 20 and navigated into and through the bronchial tree 27 with or without utilizing a delivery assembly. The elongate assembly 200 includes a distal tip 203 capable of selectively affecting tissue.

The controller 202 of FIG. 2A can include one or more processors, microprocessors, digital signal processors (DSPs), field programmable gate arrays (FPGA), and/or application-specific integrated circuits (ASICs), memory devices, buses, power sources, and the like. For example, the controller 202 can include a processor in communication with one or more memory devices. Buses can link an internal or external power supply to the processor. The memories may take a variety of forms, including, for example, one or more buffers, registers, random access memories (RAMs), and/or read only memories (ROMs). The controller 202 may also include a display, such as a screen.

In some embodiments, the controller 202 has a closed loop system or an open loop system. For example, the controller 202 can have a closed loop system, whereby the power to the distal tip 203 is controlled based upon feedback signals from one or more sensors configured to transmit (or send) one or more signals indicative of one or more tissue characteristics, energy distribution, tissue temperature, or any other measurable parameters of interest. Based on those readings, the controller 202 can then adjust operation of the distal tip 203. Alternatively, the treatment system 198 can be an open loop system wherein the operation of the distal tip 203 is set by user input. For example, the treatment system 198 may be set to a fixed power mode. It is contemplated that the treatment system 198 can be repeatedly switched between a closed loop system and an open loop system to treat different types of sites.

The distal tip 203 of FIGS. 2A-4 can target various sites in the lungs 10, including, without limitation, nerve tissue (e.g., tissue of the vagus nerves 41, 42, nerve trunks 45, etc.), fibrous tissue, diseased or abnormal tissues (e.g., cancerous tissue, inflamed tissue, and the like), muscle tissue, blood, blood vessels, anatomical features (e.g., membranes, glands, cilia, and the like), or other sites of interest. Various types of distal tips are discussed in connection with FIGS. 5A-14B.

Figure 3:
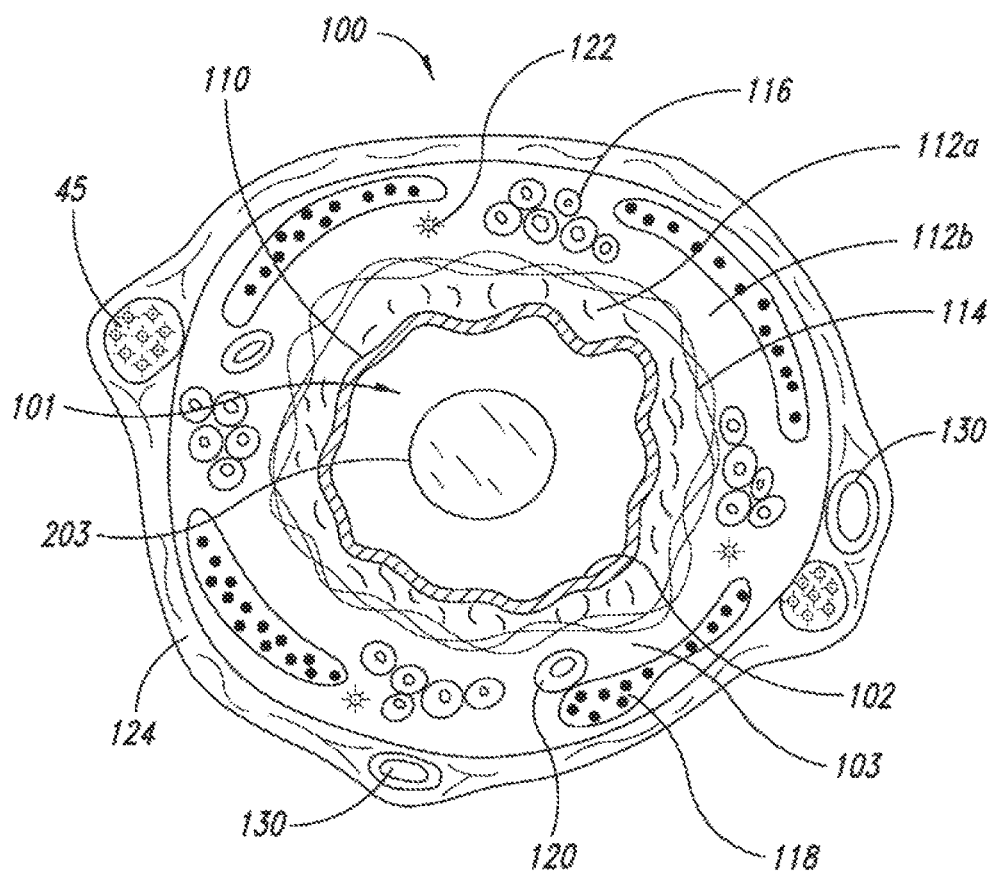
FIG. 3 is a cross-sectional view of an airway of a bronchial tree surrounding a distal tip of a treatment system positioned along an airway lumen according to one embodiment.

FIG. 3 is a transverse cross-sectional view of a healthy airway 100, illustrated as a bronchial tube. The distal tip 203 is positioned along a lumen 101 defined by an inner surface 102 of the airway 100. The illustrated inner surface 102 is defined by a folded layer of epithelium 110 surrounded by stroma 112a. A layer of smooth muscle tissue 114 surrounds the stroma 112a. A layer of stroma 112b is between the muscle tissue 114 and connective tissue 124. Mucous glands 116, cartilage plates 118, blood vessels 120, and nerve fibers 122 are within the stroma layer 112b. Bronchial artery branches 130 and nerve trunks 45 are exterior to a wall 103 of the airway 100. The illustrated arteries 130 and nerve trunks 45 are within the connective tissue 124 surrounding the airway wall 103 and can be oriented generally parallel to the airway 100. In FIG. 1, for example, the nerve trunks 45 originate from the vagus nerves 41, 42 and extend along the airway 100 towards the air sacs. The nerve fibers 122 are in the airway wall 103 and extend from the nerve trunks 45 to the muscle tissue 114. Nervous system signals are transmitted from the nerve trunks 45 to the muscle 114 via the nerve fibers 122.

The distal tip 203 of FIG. 3 can damage, excite, or otherwise elicit a desired response of the cilia along the epithelium 110 in order to control (e.g., increase or decrease) mucociliary transport. Many particles are inhaled as a person breathes, and the airways function as a filter to remove the particles from the air. The mucociliary transport system functions as a self-cleaning mechanism for all the airways throughout the lungs 10. The mucociliary transport is a primary method for mucus clearance from distal portions of the lungs 10, thereby serving as a primary immune barrier for the lungs 10. For example, the inner surface 102 of FIG. 3 can be covered with cilia and coated with mucus. As part of the mucociliary transport system, the mucus entraps many inhaled particles (e.g., unwanted contaminates such as tobacco smoke) and moves these particles towards the larynx. The ciliary beat of cilia moves a continuous carpet of mucus and entrapped particles from the distal portions of the lungs 10 past the larynx and to the pharynx for expulsion from the respiratory system. The distal tip 203 can damage the cilia to decrease mucociliary transport or excite the cilia to increase mucociliary transport.

In some embodiments, the distal tip 203 selectively treats targeted treatment sites inside of the airway wall 103 (e.g., anatomical features in the stromas 112a, 112b). For example, the mucous glands 116 can be damaged to reduce mucus production a sufficient amount to prevent the accumulation of mucus that causes increased air flow resistance while preserving enough mucus production to maintain effective mucociliary transport, if needed or desired. In some embodiments, for example, the distal tip 203 outputs ablative energy that travels through the inner periphery of the airway wall 103 to the mucous glands 116. In other embodiments, the distal tip 203 is inserted into the airway wall 103 to position the distal tip 203 next to the mucous glands 116. The embedded distal tip 203 then treats the mucous glands 116 while limiting treatment of surrounding tissue. The distal tip 203 can also be used to destroy nerve branches/fibers passing through the airway wall 103 or other anatomical features in the airway wall 103.

If the airway 100 is overly constricted, the air flow resistance of the airway 100 may be relatively high. The distal tip 203 can relax the muscle tissue 114 to dilate the airway 100 to reduce air flow resistance, thereby allowing more air to reach the alveolar sacs for the gas exchange process. Various airways of the bronchial tree 47 may have muscles that are constricted in response to signals traveling through the nerve trunks 45. The tip 203 can damage sites throughout the lungs 10 to dilate constricted airways.

Figure 4:
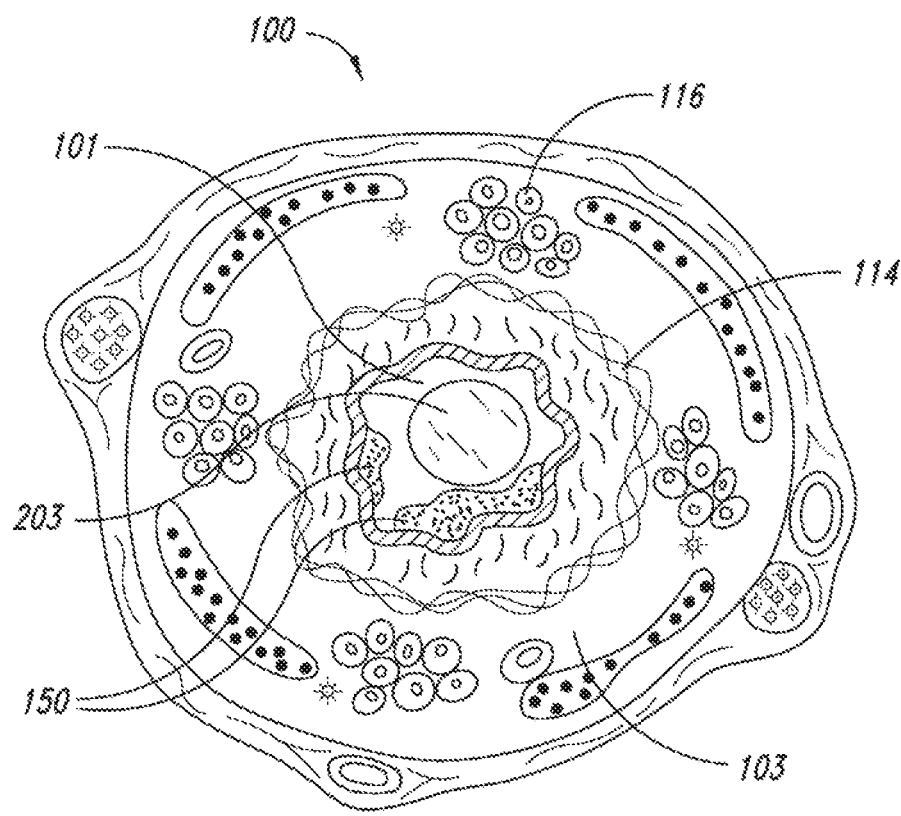
FIG. 4 is a cross-sectional view of an airway of a bronchial tree surrounding a distal tip of a treatment system when smooth muscle of the airway is constricted and mucus is in an airway lumen according to one embodiment.

FIG. 4 is a transverse cross-sectional view of a portion of the airway 100 that has smooth muscle tissue 114 in a contracted state and mucus 150 from hypertrophied mucous glands 116. The contracted muscle tissue 114 and mucus 150 cooperate to partially obstruct the lumen 101. The distal tip 203 can relax the smooth muscle tissue 114 and reduce, limit, or substantially eliminate mucus production of the mucous glands 116. The airway 100 may then dilate and the amount of mucus 150 may be reduced, to effectively enlarge the lumen 101.

The distal tip 203 of FIGS. 3 and 4 can deliver different types of energy. As used herein, the term "energy" is broadly construed to include, without limitation, thermal energy, cryogenic energy (e.g., cooling energy), electrical energy, acoustic energy (e.g., ultrasonic energy), radio frequency energy, pulsed high voltage energy, mechanical energy, ionizing radiation, optical energy (e.g., light energy), and combinations thereof, as well as other types of energy suitable for treating tissue. By way of example, thermal energy can be used to heat tissue. Mechanical energy can be used to puncture, tear, cut, crush, or otherwise physically damage tissue. In some embodiments, the distal tip 203 applies pressure to tissue in order to temporarily or permanently damage tissue. Electrical energy is particularly well suited for damaging cell membranes, such as the cell membranes of nerve trunk tissue or other targeted anatomical features. Acoustic energy can be emitted as continuous or pulsed waves, depending on the parameters of a particular application. Additionally, acoustic energy can be emitted in waveforms having various shapes, such as sinusoidal waves, triangle waves, square waves, or other wave forms.

In some embodiments, a fluid (e.g., a liquid, gas, or mixtures thereof) is employed to damage tissue. The distal tip 203 can include one or more flow elements through which the fluid can circulate to control the surface temperature of the flow element. The flow element can be one or more balloons, expandable members, and the like. The fluid can be heated/cooled saline, cryogenic fluids, and the like. Additionally or alternatively, the distal tip 203 can include one or more ports through which fluid flows to traumatize tissue.

In some embodiments, the distal tip 203 delivers one or more substances (e.g., radioactive seeds, radioactive materials, etc.), treatment agents, and the like. Exemplary non-limiting treatment agents include, without limitation, one or more antibiotics, anti-inflammatory agents, pharmaceutically active substances, bronchoconstrictors, bronchodilators (e.g., beta-adrenergic agonists, anticholinergics, etc.), nerve blocking drugs, photoreactive agents, or combinations thereof. For example, long acting or short acting nerve blocking drugs (e.g., anticholinergics) can be delivered to the nerve tissue to temporarily or permanently attenuate signal transmission. Substances can also be delivered directly to the nerves 122 or the nerve trunks 45, or both, to chemically damage the nerve tissue.

FIGS. 5A-14B illustrate embodiments for delivery along a lumen of an airway. The illustrated embodiments are just some examples of the types of treatment systems capable of performing particular procedures. It should be recognized that each of the treatment systems described herein can be modified to treat tissue at different locations, depending on the treatment to be performed. Treatment can be performed in airways that are either inside or outside of the left and right lungs. FIGS. 5A-13B illustrate treatment systems capable of outputting energy. These treatment systems may continuously output energy for a predetermined period of time while remaining stationary. Alternatively, the treatment systems may be pulsed, may be activated multiple times, or may be actuated in a combination of any of these ways. Different energy application patterns can be achieved by configuring the treatment system itself or may involve moving the treatment assembly or any of its components to different locations.

Figure 5A:
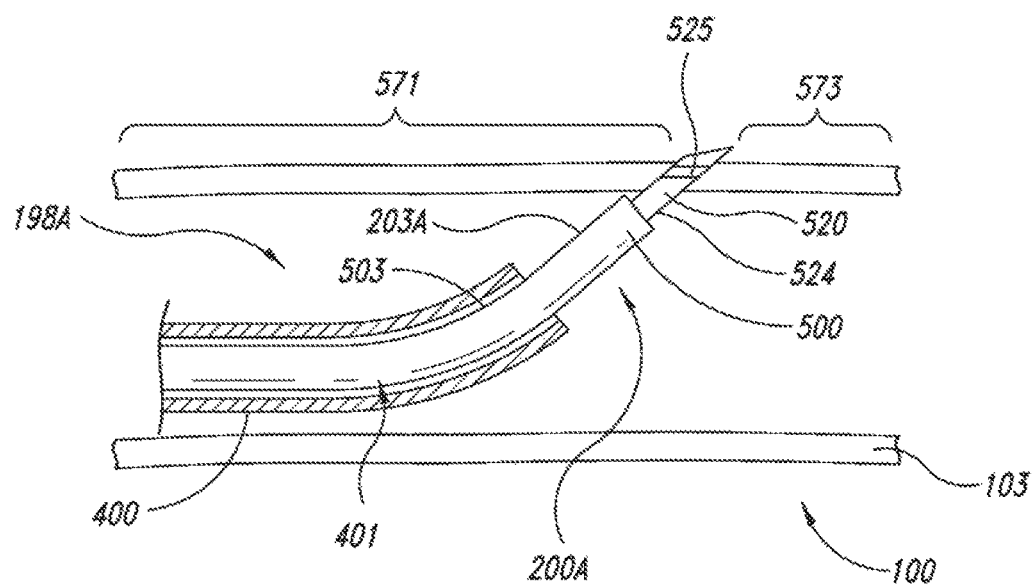
FIG. 5A is a partial cross-sectional view of a treatment system having a delivery assembly and an elongate assembly extending through and out of the delivery assembly.

Referring to FIG. 5A, a treatment system 198A includes an elongate assembly 200A that has a distal tip 203A positioned along the airway 100. The elongate assembly 200A extends through a working lumen 401 of a delivery assembly 400 and includes a flexible shaft 500 and a deployable ablation assembly 520 protruding from the shaft 500.

The shaft 500 can be a generally straight shaft that is bent as it moves along the lumen 401. In some embodiments, the shaft 500 has a preformed non-linear section 503 to direct the ablation assembly 520 towards the airway wall 103. As shown in FIG. 5A, the lumen 401 can have a diameter that is significantly larger than the outer diameter of the shaft 500. When the shaft 500 passes out of the delivery assembly 400, the shaft 500 assumes the preset configuration. The flexible shaft 500 can be made, in whole or in part, of one or more metals, alloys (e.g., steel alloys such as stainless steel), plastics, polymers, and combinations thereof, as well as other biocompatible materials.

In some embodiments, the shaft 500 selectively moves between a delivery configuration and a treatment configuration. For example, the shaft 500 can have a substantially straight configuration for delivery and a curved configuration for engaging tissue. In such embodiments, the shaft 500 can be made, in whole or in part, of one or more shape memory materials, which move the shaft 500 between the delivery configuration and the treatment configuration when activated. Shape memory materials include, for example, shape memory alloys (e.g., NiTi), shape memory polymers, ferromagnetic materials, and the like. These materials can be transformed from a first preset configuration to a second preset configuration when activated (e.g., thermally activated).

The ablation assembly 520 includes a protective section 524 and an ablation element 525. When the ablation element 525 is activated, the ablation element 525 outputs energy to targeted tissue. The protective section 524 inhibits or blocks the outputted energy to protect non-targeted tissue. The ablation element 525 and the protective section 524 thus cooperate to provide localized delivery of energy to minimize, limit, or substantially eliminate unwanted ancillary trauma associated with the outputted energy.

The ablation element 525 can be adapted to output energy that ablates tissue. The terms "ablate" or "ablation," including derivatives thereof, include, without limitation, substantial altering of electrical properties, mechanical properties, chemical properties, or other properties of tissue. In the context of pulmonary ablation applications shown and described with reference to the variations of the illustrative embodiments herein, "ablation" includes sufficiently altering of nerve tissue properties to substantially block transmission of electrical signals through the ablated nerve tissue.

The term "element" within the context of "ablation element" includes a discrete element, such as an electrode, or a plurality of discrete elements, such as a plurality of spaced apart electrodes, which are positioned so as to collectively treat a region of tissue or treat discrete sites. One type of ablation element emits energy that ablates tissue when the element is coupled to and energized by an energy source. Example energy emitting ablation elements include, without limitation, electrode elements coupleable to direct current ("DC") sources or alternating current ("AC") sources (e.g., radiofrequency ("RF") current sources), antenna elements energizable by microwave energy sources, pulsed high voltage sources, heating elements (e.g., metallic elements or other thermal conductors which are energized to emit heat via convective heat transfer, conductive heat transfer, etc.), light emitting elements (e.g., fiber optics capable of transmitting light sufficient to ablate tissue when the fiber optics are coupled to a light source), light sources (e.g., lasers, light emitting diodes, etc.), ultrasonic elements such as ultrasound elements adapted to emit ultrasonic sound waves sufficient to ablate tissue when coupled to suitable excitation sources), combinations thereof, and the like.

As used herein, the term "ablate," including variations thereof, is construed to include, without limitation, to destroy or to permanently damage, injure, or traumatize tissue. For example, ablation may include localized tissue destruction, cell lysis, cell size reduction, necrosis, or combinations thereof.

In some embodiments, the ablation assembly 520 can be connected to an energy generator (e.g., a radiofrequency (RF) electrical generator) by electrical cables within the shaft 500. For example, the RF electrical generator can be incorporated into the controller 202 of FIG. 2A. In some embodiments, the RF electrical generator is incorporated into the ablation assembly 520.

RF energy can be outputted at a desired frequency based on the treatment. Example frequencies include, without limitation, frequencies in the range of about 50 KHZ to about 1000 MHZ. When the RF energy is directed into tissue, the energy is converted within the tissue into heat causing the temperature of the tissue to be in the range of about 40° C. to about 99° C. The RF energy can be applied for a length of time in the range of about 1 second to about 120 seconds. In some embodiments, the RF generator has a single channel and delivers approximately 1 to 25 watts of RF energy and possesses continuous flow capability. Other ranges of frequencies, time internals, and power outputs can also be used.

The protective section 524 can be in the form of a shield made, in whole or in part, of a material that is non-transmissive with respect to the energy from the ablation element 525. In some embodiments, the protective section 524 is comprised of one or more metals, optically opaque materials, and the like. If the ablation element 525 outputs ablative energy, the protective section 524 can block a sufficient amount of the ablative energy to prevent ablation of tissue directly next to the protective section 524. In this manner, non-targeted tissue is not permanently damaged.

Figure 5B:
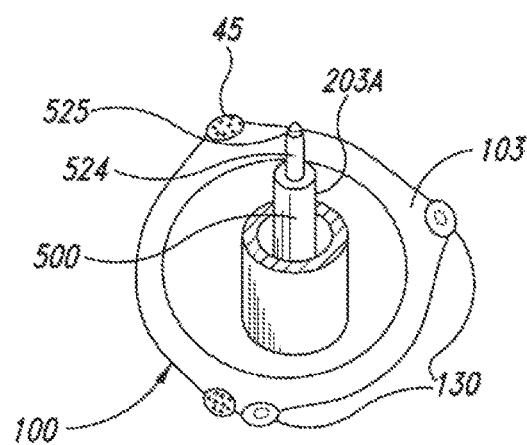
FIG. 5B is an illustration of a distal tip of the elongate assembly of FIG. 5A positioned to affect nerve tissue of a nerve trunk.

A user can visually inspect the airway 100 using the delivery assembly 400 of FIGS. 5A and 5B to locate and evaluate the treatment site(s) and non-targeted tissues before, during, and/or after performing a therapy. The delivery assembly 400 can be a catheter, delivery sheath, bronchoscope, endoscope, or other suitable device for guiding the elongate assembly 200A. In some embodiments, the delivery assembly 400 includes one or more viewing devices, such as optical viewing devices (e.g., cameras), optical trains (e.g., a set of lens), and the like. For example, the delivery assembly 400 can be in the form of a bronchoscope having one or more lights for illumination and optical fibers for transmitting images. By way of another example, the delivery assembly 400 can have an ultrasound viewing device, as discussed in connection with FIGS. 11A and 11B.

FIGS. 6-9 show one exemplary method of using the treatment system 198A. Generally, the treatment system 198A can alter nerve tissue of the airway 100 to control nervous system input to a portion of the lung while not damaging to any significant extent other pulmonary structures.

Figure 6:
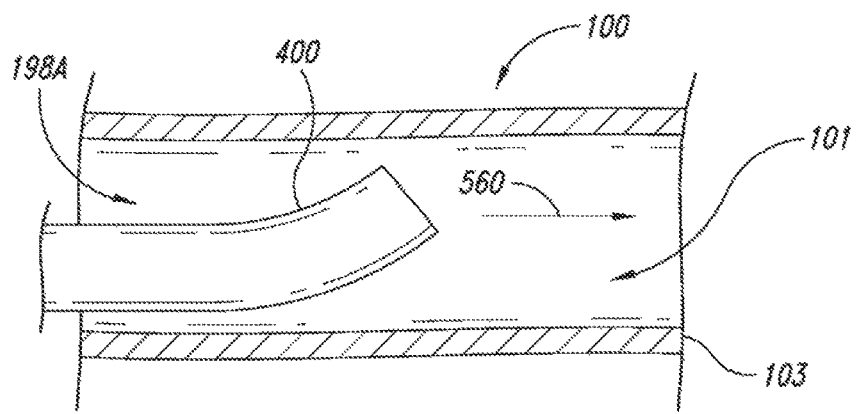
FIG. 6 is a side elevational view of a delivery assembly in a lumen of a bronchial airway according to one embodiment.

As shown in FIG. 6, the delivery assembly 400 is moved along the lumen 101 of the airway 100, as indicated by an arrow 560. The elongate assembly 200A is carried in the delivery assembly 400 to prevent injury to the airway 100 during positioning of the delivery assembly 400.

Figure 7:
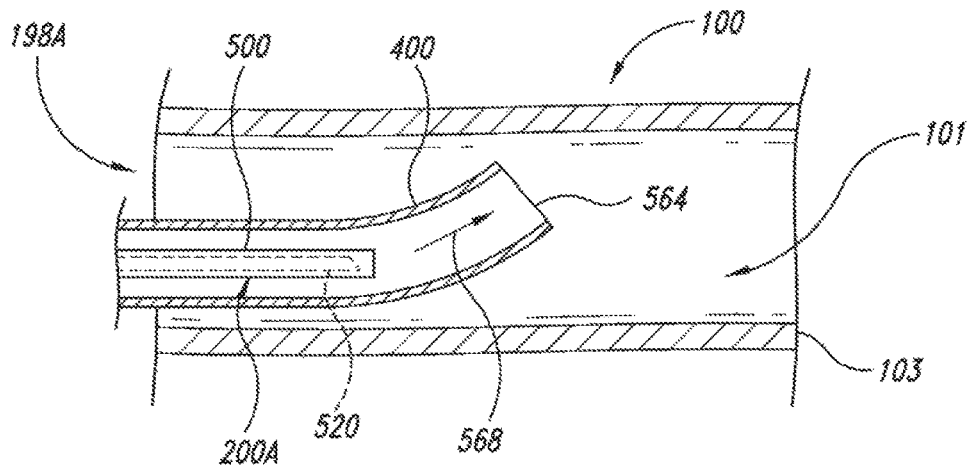
FIG. 7 is a side elevational view of a distal tip of an elongate assembly moving through the delivery assembly of FIG. 6.

FIG. 7 shows the elongate assembly 200A moving along the lumen 401 towards an opening 564, as indicated by an arrow 568. While the elongate assembly 200A is moved through the delivery assembly 400 (shown in cross-section), the ablation assembly 520 (shown in phantom) can be housed within the shaft 500 to prevent damage to the airway 100 or the delivery assembly 400, or both. A user can push the shaft 500 out of the delivery assembly 400 towards the airway wall 103.

Figure 8:
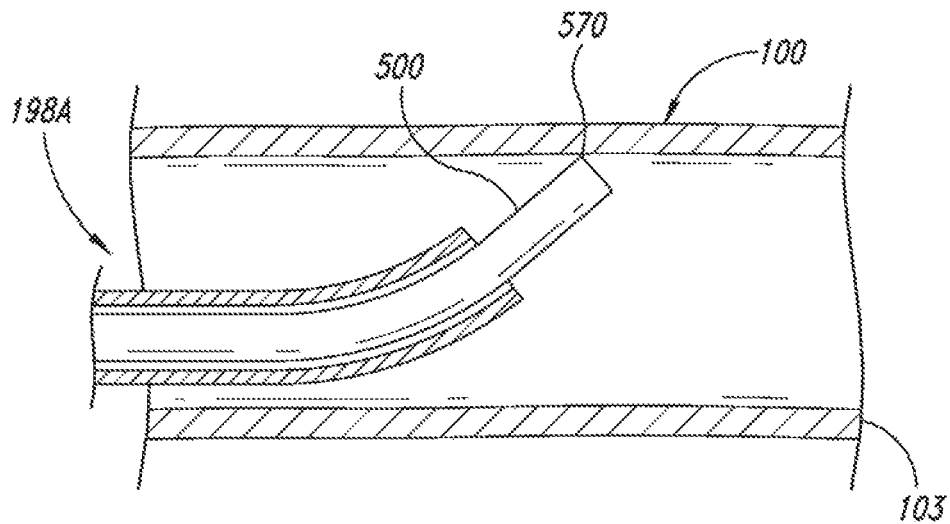
FIG. 8 is a side elevational view of the distal tip of the elongate assembly protruding from the delivery assembly according to one embodiment.
Figure 9:
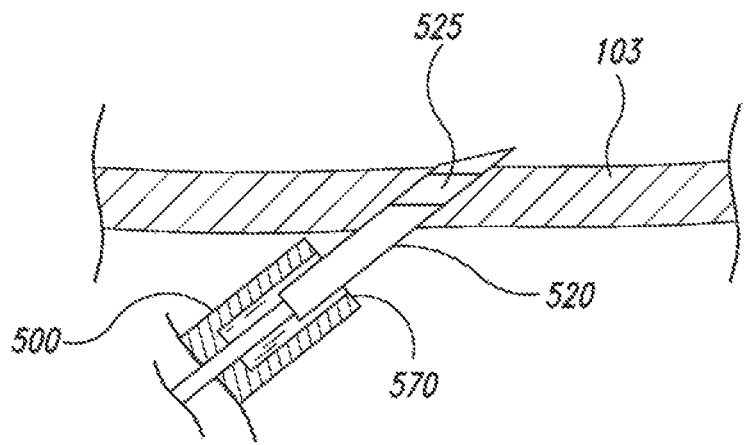
FIG. 9 is an enlarged partial cross-sectional view of the distal tip of FIG. 8, wherein the distal tip extends into a wall of the airway.

FIG. 8 shows a distal end 570 of the shaft 500 proximate to the wall 103. The sharp ablation assembly 520 is deployed from the shaft 500 and contacts the wall 103. The ablation assembly 520 is then advanced through the wall 103 until the exposed ablation element 525 is embedded within the wall 103, as shown in FIG. 9. The position of the ablation assembly 520 relative to the airway wall 103 can be adjusted by extending or retracting the ablation assembly 520. Because the ablation assembly 520 is relatively slender, the wall 103 can experience an insignificant amount of trauma.

The illustrated ablation assembly 520 is connected to one lead of the RF generator and the other lead of the RF generator may be connected to an external electrode. When the RF generator is activated, the ablation element 525 delivers RF energy to tissue contacting or adjacent to the ablation element 525. RF energy flows through the tissue and is converted into heat. The heat can be concentrated in the outer portion of the airway wall 103. For example, the ablation element 525 of FIG. 5B outputs RF energy that causes damage to the nerve trunks 45. In some embodiments, a sufficient amount of RF energy is delivered to the nerve trunk 45 to destroy an entire longitudinal section of the nerve trunk 45 while keeping the amount energy that reaches the blood vessels 130 below an amount that causes tissue destruction. Damage to other non-targeted regions (e.g., the epithelium) can also be kept at or below an acceptable level. Thus, therapies can be performed without damaging to any significant extent other regions of the airway 100, even regions that are adjacent to the treatment site.

Natural body functions can help prevent, reduce, or limit damage to tissue. If the bronchial artery branches 130 are heated by the treatment system 198A, blood within the blood vessels 130 can absorb the thermal energy and can then carry the thermal energy away from the heated section of the branches 130. In this manner, thermal energy is transferred to the blood. After the treatment is performed, the bronchial artery branches 130 can continue to maintain the health of lung tissue.

This procedure may be repeated to damage additional tissue of nerve trunks 45 located outside the circumference of the wall 103. In some embodiments, all the nerves about the airway 100 can be treated to prevent signals from passing between a proximal section 571 of the airway 100 and distal section 573 of the airway 100, as shown in FIG. 5A. Because signals are not transmitted to the distal section 573, the distal section 573 can dilate. The airway 100 can also remain generally intact to maintain the health of the distal section 573. Upon completion of the treatment process, the ablation assembly 520 is retracted back into the shaft 500 for removal from the airway 100 or for placement at other treatment locations.

Treatment efficacy can be evaluated based at least in part on one or more airway attributes, pulmonary function tests, exercise capacity tests, and/or questionnaires. Patients can be evaluated to track and monitor their progress. If needed or desired, additional procedures can be performed until desired responses are achieved.

Different types of instruments for evaluating airway attributes may be used with treatment systems. During ablation, feedback from an instrument can indicate whether the targeted tissue has been ablated. Once targeted tissue is ablated, therapy can be discontinued to minimize or limit collateral damage, if any, to healthy untargeted tissue. FIG. 2B shows an instrument 199 with a detection element in the form of a balloon. Fluid (e.g., air, saline solution, or the like) can be used inflate the balloon to evaluate airway attributes. The instrument 199 can be a conventional instrument for airway dilation, airway occlusion, or the like. Instruments available for purchase from numerous medical suppliers, including Ackrad Laboratories, Cranford, N.J. and Erich Jaeger, Hoechberg, Germany, can be used with, or modified to be used with, the treatments systems disclosed herein. The instruments can be delivered through the treatment systems (e.g., through a central lumen of the treatment system) to position a detection element distal to the treatment system.

The attributes of airways evaluated by the instrument may include, without limitation, physical properties of airways (e.g., airway compliance, contractile properties, etc.), airway resistance, dimensions of airway lumens (e.g., shapes of airways, diameters of airways, etc.), responsiveness of airways (e.g., responsiveness to stimulation), muscle characteristics (e.g., muscle tone, muscle tension, etc.), or the like. In some embodiments, changes of airway muscle characteristics can be monitored by measuring pressure changes the intraluminal balloon that is inflated to a known pressure. Based on pressure changes in the balloon, a physician determines the effects, if any, of the treatment, including, without limitation, whether targeted tissue has been stimulated, damaged, ablated, or the like. For example, the balloon can be positioned distal to the targeted tissue. As nerve tissue is damaged, muscle tension in the airway surrounding the balloon is reduced causing expansion of the airway, as well as expansion of the balloon. The pressure in the balloon decreases as the balloon expands.

The instrument 199 and the treatment system 198 can be delivered through different lumens in a delivery device, including, without limitation, a multi-lumen catheter, a delivery sheath, bronchoscope, an endoscope, or other suitable device for delivering and guiding multiple devices. The delivery device can be selected based on the location of the treatment site(s), configuration of the treatment system, or the like.

Decreases in airway resistance may indicate that passageways of airways are opening, for example, in response to attenuation of nervous system input to those airways. The decrease of airway resistance associated with treating low generation airways (e.g., main bronchi, lobar bronchi, segmental bronchi) may be greater than the amount of decrease of airway resistance associated with treating high generation airways (e.g., subsegmental bronchioles). A physician can select appropriate airways for treatment to achieve a desired decrease in airway resistance and can be measured at a patient's mouth, a bronchial branch that is proximate to the treatment site, a trachea, or any other suitable location. The airway resistance can be measured before performing the therapy, during the therapy, and/or after the therapy. In some embodiments, airway resistance is measured at a location within the bronchial tree by, for example, using a vented treatment system that allows for respiration from areas that are more distal to the treatment site.

Figure 10A:
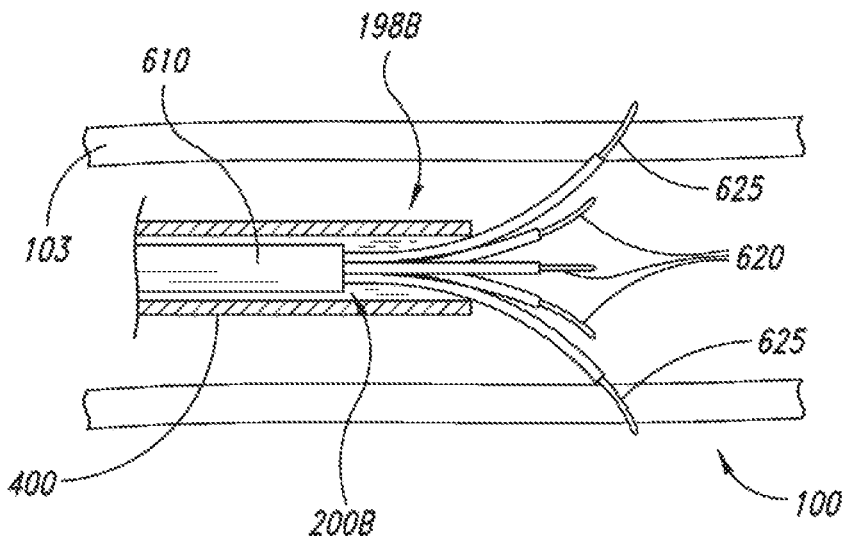
FIG. 10A is a side elevational view of a self-expanding ablation assembly in an airway according to one embodiment.

FIGS. 10A-14B illustrate treatment assemblies that can be generally similar to the treatment assembly 198A discussed in connection with FIGS. 5A-9, except as detailed below. FIG. 10A illustrates a treatment system 198B that includes an elongate assembly 200B. The elongate assembly 200B includes an elongate flexible shaft 610 and a plurality of radially deployable ablation assemblies 620. The ablation assemblies 620 can be collapsed inwardly when the shaft 610 is pulled proximally through the delivery assembly 400 (shown in cross-section). When the plurality of ablation assemblies 620 is pushed out of the delivery assembly 400, the ablation assemblies 620 self-expand by biasing radially outward.

Each electrode assembly 620 includes a sharp tip for piercing the airway wall 103 and includes extendable and retractable sharp ablation elements 625. The ablation assemblies 620 are preferably insulated except for the exposed ablation elements 625. The ablation assemblies 620 can be connected to a RF electrical generator by electrical cables that travel within the shaft 610. While the treatment system 198B is being delivered, the ablation assemblies 620 may be positioned within the shaft 610. The ablation assemblies 620 can be moved out of the shaft 610 and brought into contact with the wall 103. The ablation assemblies 620 can be simultaneously moved through the airway wall 103 until desired lengths of the ablation elements 625 are within the airway wall 103.

Figure 10B:
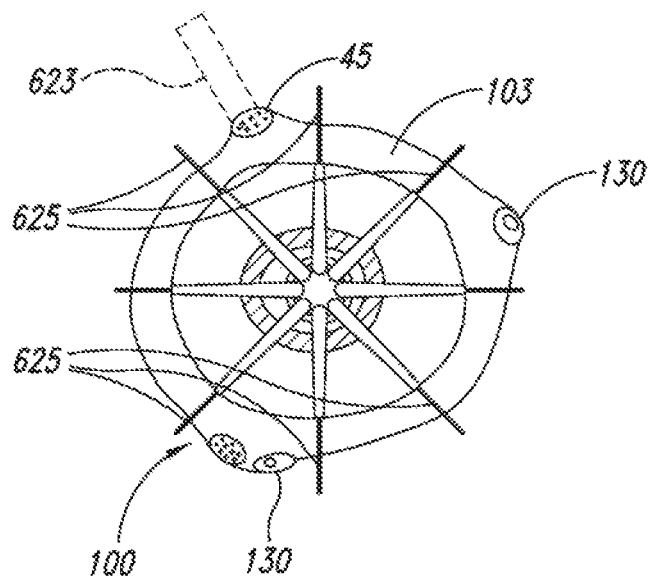
FIG. 10B is a front view of the ablation assembly of FIG. 10A.

As shown in FIG. 10B, the plurality of ablation elements 625, illustrated as electrodes, may be circumferentially spaced from each other along the airway wall 103. The ablation elements 625 can be evenly or unevenly spaced from one another.

All of the ablation assemblies 620 can be connected to one lead of the RF generator and the other lead of the RF generator may be connected to an external electrode 623 (shown in phantom), so that current flows between the ablation assemblies 620 and/or between one or more of the ablation assemblies 620 and the external electrode 623. In some embodiments, a selected number of the ablation assemblies 620 are connect to one lead of the RF generator while the other ablation assemblies 620 are connected to the other lead of the RF generator such that current flows between the ablation assemblies 620.

When the RF generator is activated, current flows through the tissue and generates a desired amount of heat. The heat can be concentrated on the outside of the airway wall 103 to damage peripheral tissue. For example, the temperature of the connective tissue can be higher than the temperatures of the stroma, smooth muscles, and/or the epithelium. By way of example, the temperature of the connective tissue can be sufficiently high to cause damage to the nerve tissues in the nerve trunks 45 while other non-targeted tissues of the airway 100 are kept at a lower temperature to prevent or limit damage to the non-targeted tissues. In other embodiments, heat can be concentrated in one or more of the internal layers (e.g., the stroma) of the airway wall 103 or in the inner periphery (e.g., the epithelium) of the airway wall 103.

As shown in FIG. 10B, one or more vessels of the bronchial artery branches 130 may be relatively close to the ablation elements 625. The heat generated by the ablation elements 625 can be controlled such that that blood flowing through the bronchial artery branches 130 protects the those branches 130 from thermal injury while nerve tissue is damaged, even if the nerve tissue is next to the artery branches 130. Upon completion of the treatment process, the ablation assemblies 620 are retracted back into the shaft 610 for removal from the airway 100 or for placement at other treatment locations.

Figure 11A:
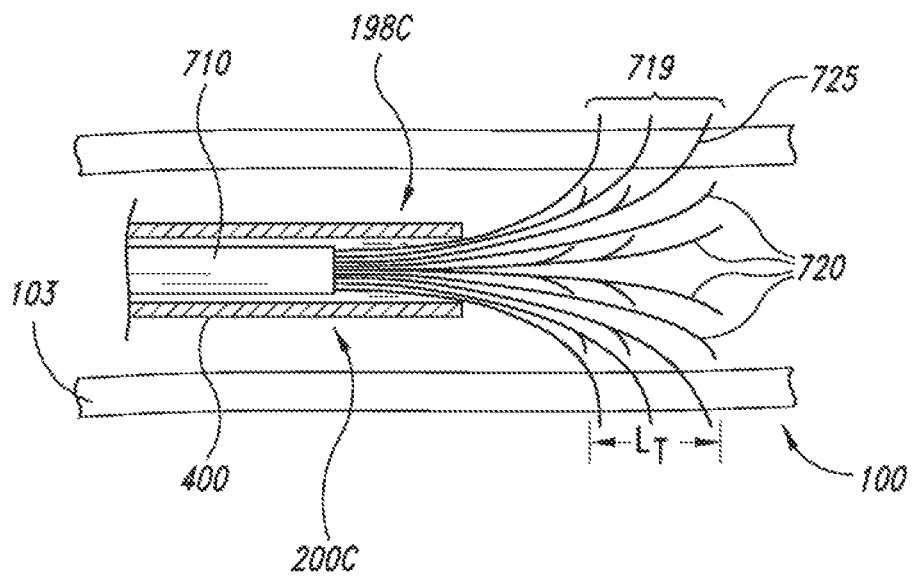
FIG. 11A is a side elevational view of another embodiment of a self-expanding ablation assembly in an airway.
Figure 11B:
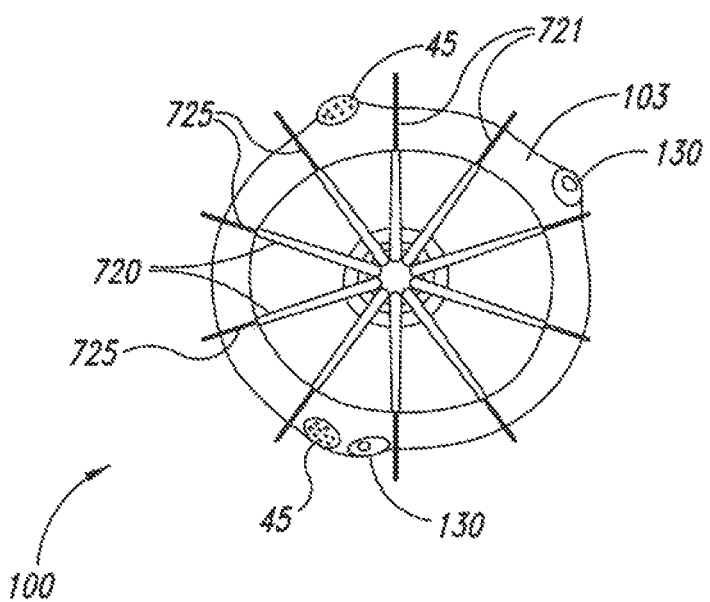
FIG. 11B is a front view of the ablation assembly of FIG. 11A.

FIGS. 11A and 11B illustrate a treatment system 198C that includes an elongate assembly 200C. The elongate assembly 200C includes an elongate flexible shaft 710 and a plurality of extendable and retractable ablation assemblies 720. When the ablation assemblies 720 are deployed, the ablation assemblies 720 bias radially outward and into contact with a tubular section 719 of the airway 100. Ablation elements 725 of the ablation assemblies 720 can be axially and circumferentially distributed throughout a treatment length $L_T$ of the section 719.

The ablation assemblies 720 can include protective sections 721 and the exposed ablation elements 725. The protective sections 721 can extend from the shaft 710 to an inner surface of the airway 100. The ablation elements 725 protrude from corresponding protective sections 721. The ablation assemblies 720 can be connected to a radiofrequency (RF) electrical generator by electrical cables that travel within the shaft 710.

The treatment system 198C is delivered to the desired treatment location within the airway 100. While the treatment system 198C is being delivered, the ablation assemblies 720 are retracted within the shaft 710 so as not to damage the airway 100 or the delivery device 400, or both. Once in position, the sharp ablation elements 725 are brought into contact with the airway wall 103. The elements 725 are then advanced through the airway wall 103 until the ablation elements 625 are embedded within the airway wall 103. Substantially all of the ablation assemblies 720 can be connected to one lead of the RF generator and the other lead of the RF generator may be connected to an external electrode, so that current flows between the ablation assemblies 720 and the external electrode. Alternatively, selected individual ablation assemblies 720 can be connect to one lead of the RF generator while other ablation assemblies 720 can be connected to the other lead of the RF generator, so that current can flow between the ablation assemblies 720.

Figure 12A:
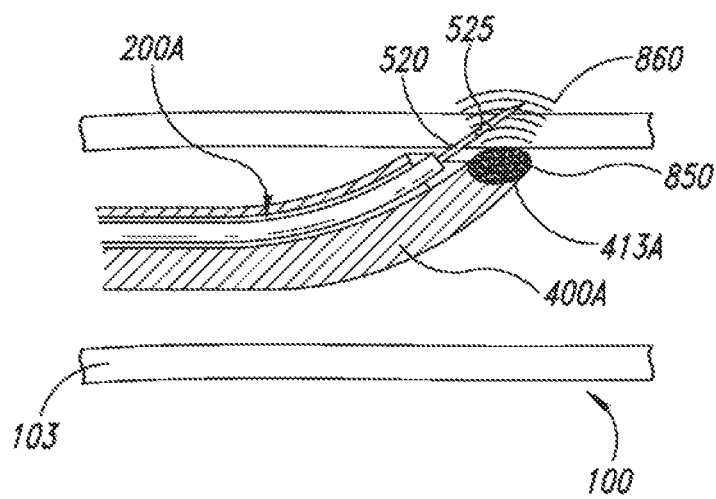
FIG. 12A is a partial cross-sectional view of a treatment system having a delivery assembly and a separate elongate assembly within the delivery assembly according to one embodiment.
Figure 12B:
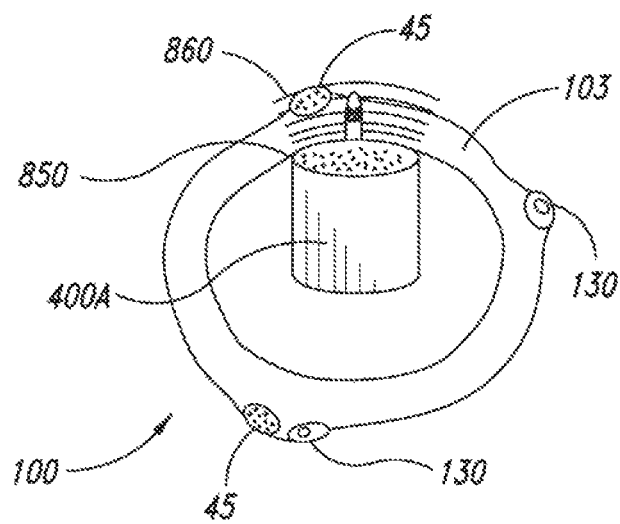
FIG. 12B is a front view of the treatment system of FIG. 12A.

FIG. 12A illustrates the elongate assembly 200A of FIGS. 5A and 5B passing through a delivery assembly 400A, illustrated as a bronchoscope, that has an imaging device 850. The imaging device 850 is positioned at a tip 413A of the delivery assembly 400A. In some embodiments, the imaging device 850 includes an array of ultrasound transducers with a working frequency between about 1 MHz to about 250 MHz and Doppler capabilities. Wavefronts 860 outputted by the imaging device 850 are illustrated in FIGS. 12A and 12B.

When used, the delivery device 400A is advanced to the desired treatment region of the airway 100. The imaging device 850 is then used to image at least a portion of the airway wall 103, thereby locating the anatomical structures, such as the nerve trunks 45 and/or bronchial artery branches 130, which are located in the connective tissue 124 outside of the airway wall. For example, the imaging device 850 can be used to circumferentially image the airway 100. In some modes of operation, target tissues (e.g., the nerve trunks 45, mucous glands 116, and the like) are located such that only the portion of the wall 103 immediately adjacent to the target tissues and the connective tissue 124 are treated. In other modes of operation, the non-targeted tissues (e.g., bronchial artery branches 130) are localized and all other regions of the wall 103 and the connective tissue 124 are treated.

When treating the nerve trunks 45, the tip 413 of the delivery device 400A can be guided and positioned near a selected nerve trunk 45. Once in position, the sharp ablation element 525 is brought into contact with the wall 103. The ablation element 525 is then advanced through the wall 103 until the ablation elements 525 are embedded. The illustrated exposed ablation elements 525 are adjacent to the nerve trunk in the connective tissue 124. The RF generator is activated and current flows between the ablation assembly 520 and the tissue of the wall 103. The current causes the tissues of the nerve trunks 45 to increase in temperature until the heated tissue is damaged. By positioning the ablation assembly 520 near the nerve trunk 45, the nerve trunk 45 is selectively damaged while injury to non-targeted tissues, such as the bronchial arteries 130, is minimized. This procedure may be repeated to damage additional nerve branches 45 located around the circumference of the wall 103 in or adjacent to the connective tissue 124.

Figure 13A:
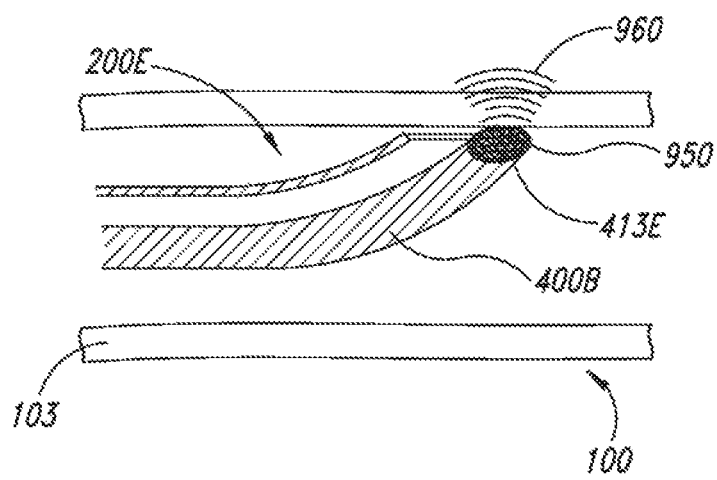
FIG. 13A is a cross-sectional view of a delivery assembly delivering energy to a treatment site according to one embodiment.
Figure 13B:
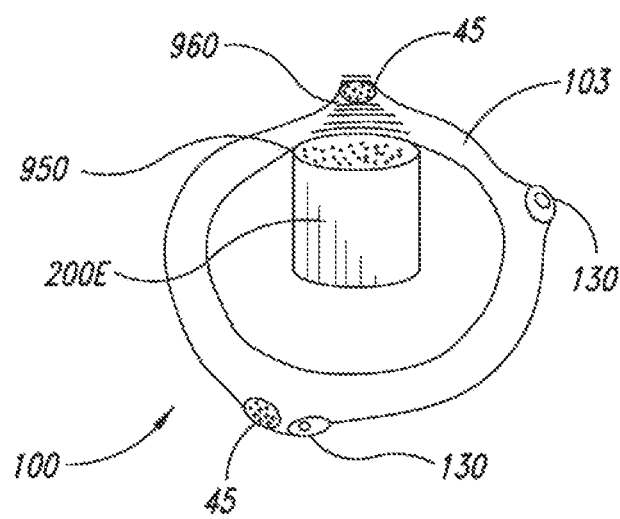
FIG. 13B is a front view of the delivery assembly of FIG. 13A.

Various types of devices can be used to remotely treat target tissues. FIGS. 13A and 13B illustrate a treatment system 200E in the form of a bronchoscope having high energy ultrasound transducer array 950 located at its tip 413E. The energy ultrasound transducer array 950 can be positioned to image the desired treatment site. The ultrasound transducer array 950 is then used to circumferentially image the wall 103 to localize the nerve trunks 45 and/or the bronchial arteries 130. In some modes of operation, the nerve trunks 45 are localized and only the area of the wall 103 of the airway 100 and the connective tissue 124 around the nerve trunks 45 is treated using ultrasound energy. In other modes of operation, the bronchial arteries 130 are localized and all other areas of the wall 103 of the airway 100 and the connective tissue 124 are treated using ultrasound energy.

The ultrasound transducer array 950 can emit highly focused sound waves 960 into the connective tissue 124 to damage the nerve trunks 45 and minimize or prevent injury to the bronchial arteries 130. The tip 413E of the bronchoscope 400B can be positioned such that the outputted energy is directed away from or does not reach the bronchial artery branches 130. This procedure of remotely treating tissue may be repeated to damage additional nerve trunks 45 located around the circumference of the wall 103 in the connective tissue 124, as desired. The bronchoscope 400B can be used to damage all or at least some of the nerve trunks 45 at a particular section of the airway 100.

Figure 14A:
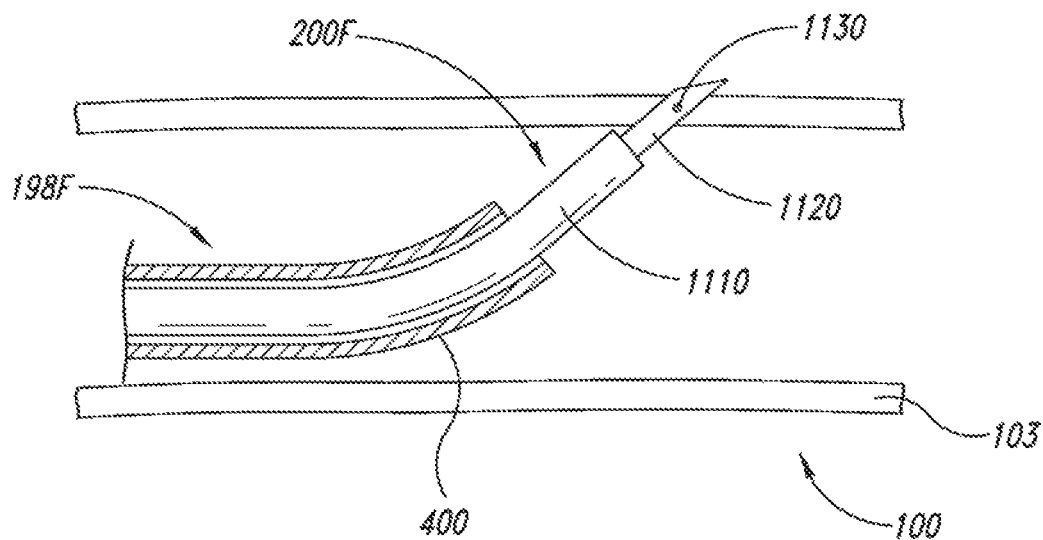
FIG. 14A is a partial cross-sectional view of a treatment system having an elongate assembly with a port positioned in an airway wall according to one embodiment.
Figure 14B:
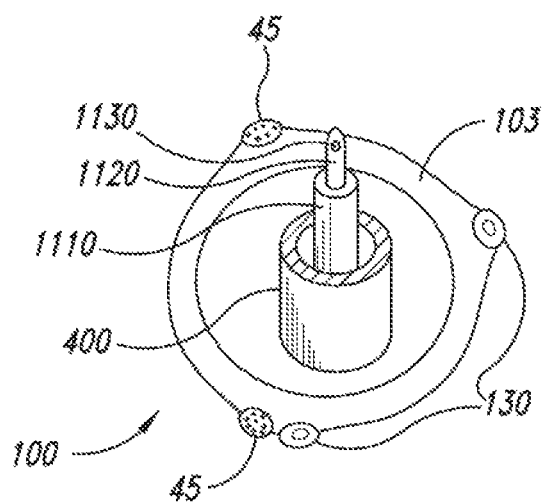
FIG. 14B is a front view of the treatment system of FIG. 14A.

FIGS. 14A and 14B illustrate a treatment system 198F that includes an elongate assembly 200F. The elongate assembly 200F includes an elongated shaft 1110 and an extendable and retractable puncturing tip 1120. The puncturing tip 1120 is adapted to pass through tissue and includes at least one port 1130. The illustrated puncturing tip 1120 includes a single side port 1130 for outputting flowable substances. A lumen can extend proximally from the port 1130 through the shaft 1110. A flowable substance can flow distally through the lumen and out of the port 1130. Example flowable substances include, without limitation, one or more heated liquids, cooled liquids, heated gases, cooled gases, chemical solutions, drugs, and the like, as well as other substances that that can cause damage to tissue. For example, saline (e.g., heated or cooled saline) or cryogenic fluids can be delivered through the port 1130.

The elongate assembly 200F of FIGS. 14A and 14B can be delivered to the desired treatment location using the delivery assembly 400. While the elongate assembly 200F is being delivered, the puncturing tip 1120 is retracted within the shaft 1110 so as to not damage the airway 100 and/or the delivery assembly 400. Once in position, the sharp hollow tip 1020 is brought into contact with the airway wall 103. The tip 1020 is then advanced through the airway wall 103 until the side port 1130 is within or adjacent to the connective tissue 124. The flowable substance is delivered through the tip 1020 and out of the port 1130 and flows against the tissue of the airway 100. In some embodiments, the expelled substance cuts, crushes, or otherwise damages the tissue. In some embodiments, the flowable substance includes at least one long acting nerve blocking drug that partially or completely blocks nerve conduction in the nerve trunks 45.

Figure 15A:
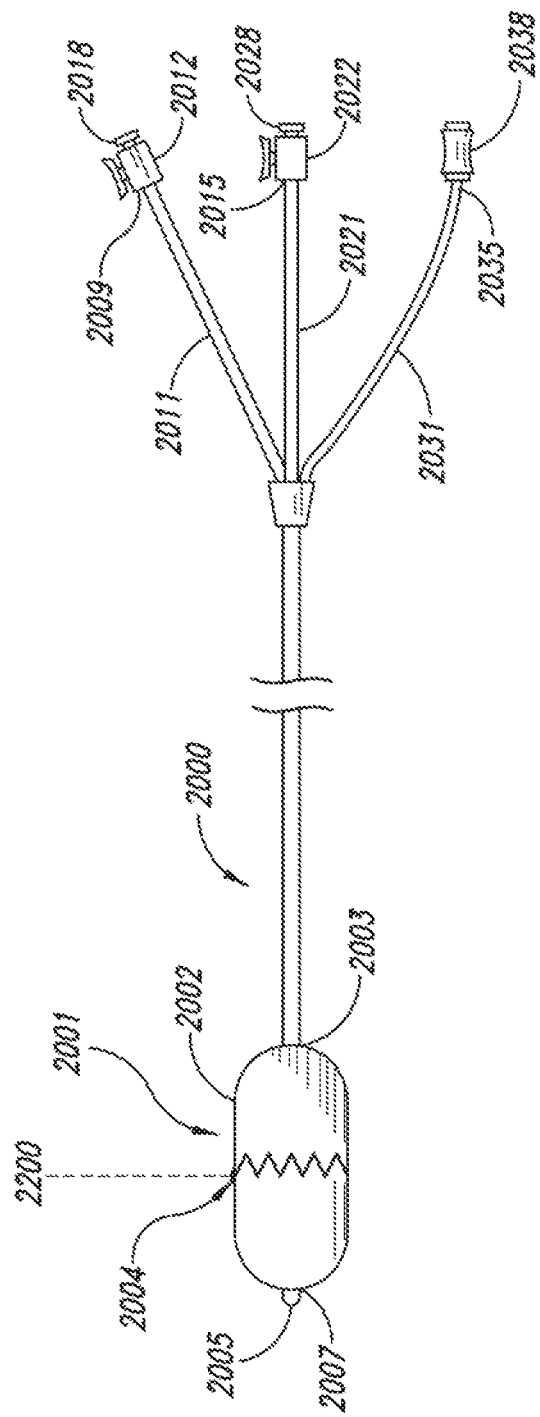
FIG. 15A is a side elevational view of a treatment system having an expandable assembly.

FIGS. 15A-19B illustrate treatment systems that can be generally similar to the treatment system 198A discussed in connection with FIGS. 5A-9, except as detailed below. FIG. 15A is a longitudinal side view of a treatment system 2000 in the form of a balloon expandable, fluid heated/cooled electrode catheter. FIG. 15B is a cross-sectional view of an expandable assembly 2001 of the system 2000. The illustrated expandable assembly 2001 is in an expanded state. Lines of flow 2100 represent the movement of fluid through the expanded assembly 2001. The expanded assembly 2001 includes an expandable member 2002 and an ablation electrode 2004. The ablation electrode 2004 can be collapsed inwardly when the treatment system 2000 is moved (e.g., pulled proximally or pushed distally) through a delivery assembly. When the treatment system 2000 is pushed out of the delivery assembly, the ablation electrode 2004 can be expanded outward by inflating the expandable member 2002.

The treatment system 2000 generally includes the expandable member 2002 (illustrated in the form of a distensible, thermally conductive balloon), an ablation electrode 2004, a conducting element 2031, an inflow line 2011, and an outflow line 2021. The ablation electrode 2004 is expandable and connected to a distal end 2033 of the conducting element 2031. A proximal end 2035 of the conducting element 2031 is connected to an electrical connector 2038. Energy is transferred from the electrical connector 2038 to the expandable electrode 2004 through the conducting element 2031. The conducting element 2031 can include, without limitation, one or more wires, conduits, or the like.

A proximal end 2009 of the inflow line 2011 has an inline valve 2012. A proximal end 2015 of the outflow line 2021 also has an outflow valve 2022. The inline valve 2011 can be connected to a fluid supply, such as a coolant source, by a connector 2018. Fluid flows through the inflow line 2011 into the balloon 2002, and exits the balloon 2002 via the outflow line 2021. The fluid can include, without limitation, temperature controlled fluid, such as water, saline, or other fluid suitable for use in a patient.

A lumen 2017 of the inflow line 2011 and a lumen 2019 of the outflow line 2021 provide fluid communication with the balloon 2002. Fluid can flow through the lumen 2017 into the balloon 2002. The fluid circulates within the balloon 2002 and flows out of the balloon 2002 via the lumen 2019. The fluid can pass through the connector 2028 to a fluid return system, which may cool the fluid and re-circulate the fluid to the fluid supply.

Different types of materials can be used to form different components of the system 2000. In some embodiments, the balloon 2002 is made, in whole or in part, of a distensible, chemically inert, non-toxic, electrically insulating, and thermally conductive material. For example, the balloon 2002 may be made of polymers, plastics, silicon, rubber, polyethylene, combinations thereof, or the like. In some embodiments, the inflow line 2011 and the outflow line 2021 are made, in whole or in part, of any suitable flexible, chemically inert, non-toxic material for withstanding operating pressures without significant expansion. The inflow line 2011 and the outflow line 2021 can have a suitable length to be passed into the lung and bronchial tree. For example, the lines 2011, 2021 can have a length of approximately 80 cm. Other lengths are also possible.

Figure 15B:
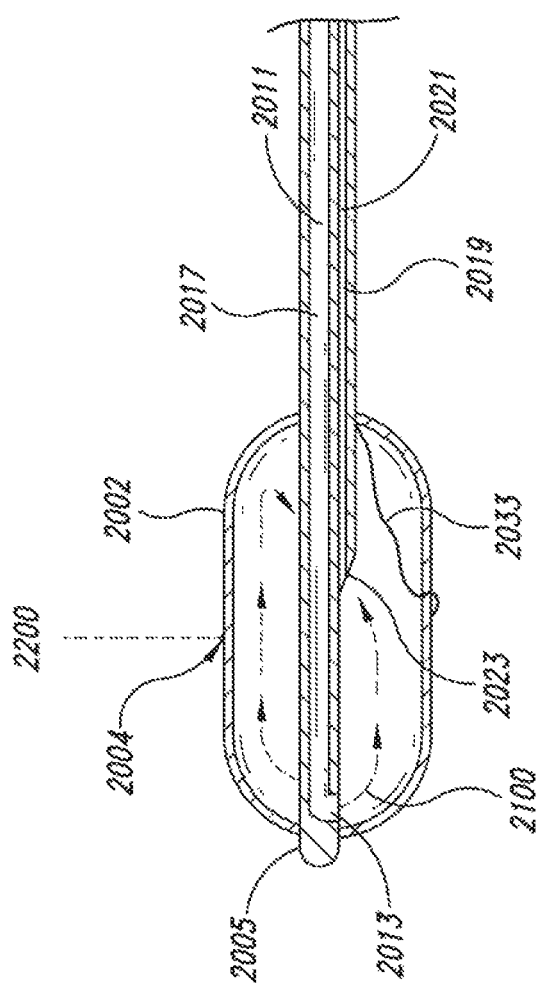
FIG. 15B is a cross-sectional view of the expandable assembly of FIG. 15A.

FIG. 15B shows the inflow line 2011 and the outflow line 2021 arranged to minimize, reduce, or substantially prevent cross flow, siphoning, or back flow between the two lines 2011, 2021. The illustrated inflow line 2011 carries the balloon 2004. The inflow line 2011 can enter a proximal end 2003 of the balloon 2002, extend through the length of the balloon 2002, and reach a distal end 2007 of the balloon 2002. The illustrated inflow line 2011 is connected to the distal end 2007 to keep the balloon 2002 in an elongated configuration.

A tip 2005 protrudes from the balloon 2002. The illustrated tip 2005 is an atruamatic tip positioned opposite the end of the inflow line 2011. Near the tip 2005, the inflow line 2011 has an aperture 2013 that releases fluid into the balloon 2002. The fluid flows within the balloon 2002 and is collected into the outflow line 2021. The illustrated outflow line 2021 has an opening 2023 for receiving the fluid. The opening 2023 is generally at the distal end of a portion of the outflow line 2021 in the balloon 2002 and collects fluid from any direction. Because the openings 2013, 2023 are at opposite ends of the balloon 2002, fluid can flow in generally one direction through the balloon 2002. This ensures that fluid at a desired temperature fills the balloon 2002.

The shapes of the electrode 2004 and the balloon 2002 can be selected such that the electrode 2004 and balloon 2004 expand/deflate together. When the balloon 2002 is inflated, the electrode 2004 is expanded with the balloon 2002. When the balloon 2002 is deflated, the electrode 2004 contracts with the balloon 2002. The electrode 2004 may be coupled to an exterior surface or interior surface of the balloon 2002 and may be made of different types of conductive materials, including, without limitation, any chemically inert, non-toxic, structurally resilient, electrically conducting material. In some embodiments, the electrode 2004 is coupled to the exterior of the balloon 2002 and made, in whole or in part, of a highly conductive, deformable material. Energy outputted by the electrode 2004 is outputted directly into the airway wall 100 without passing through the wall of the balloon 2002. The electrode 2004 can be a thin wire or band made mostly or entirely of copper. The wire can be coated or uncoated depending on the application. In other embodiments, the electrode 2004 is embedded in the wall of the balloon 2002. Any number of electrodes 2004 can be positioned along the balloon 2002. For example, an array of spaced apart electrodes can be positioned along the balloon to treat a length of an airway.

The electrical conducting element 2031 travels along side and generally parallel to one or both of the lines 2011, 2021. The electrode 2004 can be connected through the electrical conducting element 2031 and the electrical connector 2038 to an energy source, such as an RF electrical generator. If the energy source is an RF electrical generator, one lead can be coupled to the connector 2038. The other lead of the RF generator may be connected to an external electrode, such as the external electrode 623 shown in phantom in FIG. 10B, so that current flows between the expandable electrode 2004 and the external electrode.

The balloon expandable, fluid cooled electrode catheter 2000 can be delivered into the airways of the lung with the balloon 2002 deflated and the electrode 2004 contracted. The electrode 2004 can be kept in a collapsed or closed configuration to allow the catheter 2000 to pass easily through the lungs. The catheter 2000 is moved through the airways until the electrode 2004 is at the desired treatment location. Once in position, fluid (e.g., coolant) is allowed to flow through the inflow line 2011 and into the balloon 2002. The fluid inflates the balloon 2002 which in turn expands the electrode 2004. Outflow of the fluid through the outflow line 2021 can be regulated such that the balloon 2002 continues to inflate until the electrode 2004 is brought into contact with or proximate to the airway wall.

Treatment can begin with activation of the RF generator. When the RF generator is activated, RF energy is transmitted through the electrical connector 2038, through the electrical connection element 2031, through the expanded electrode 2004, and into the tissues of the airways. The RF energy heats tissue (e.g., superficial and deep tissue) of the airway wall and the fluid 2100 (e.g., a coolant) flowing through the balloon 2002 cools tissue (e.g., superficial tissues) of the airway wall. The net effect of this superficial and deep heating by RF energy and superficial cooling by the circulating coolant 2100 through the balloon 2002 is the concentration of heat in the outer layers of the airway wall 100. The coolant can be a chilled liquid. The temperature of the connective tissue can be higher than the temperatures of the epithelium, stroma, and/or smooth muscle. By example, the temperature of the connective tissue can be sufficiently high to cause damage to the nerve trunk tissue while other non-targeted tissues of the airway are kept at a lower temperature to prevent or limit damage to the non-targeted tissues. In other embodiments, heat can be concentrated in one or more of the internal layers (e.g., the stroma) of the airway wall or in the inner lining (e.g., the epithelium) of the airway wall.

Figure 16:
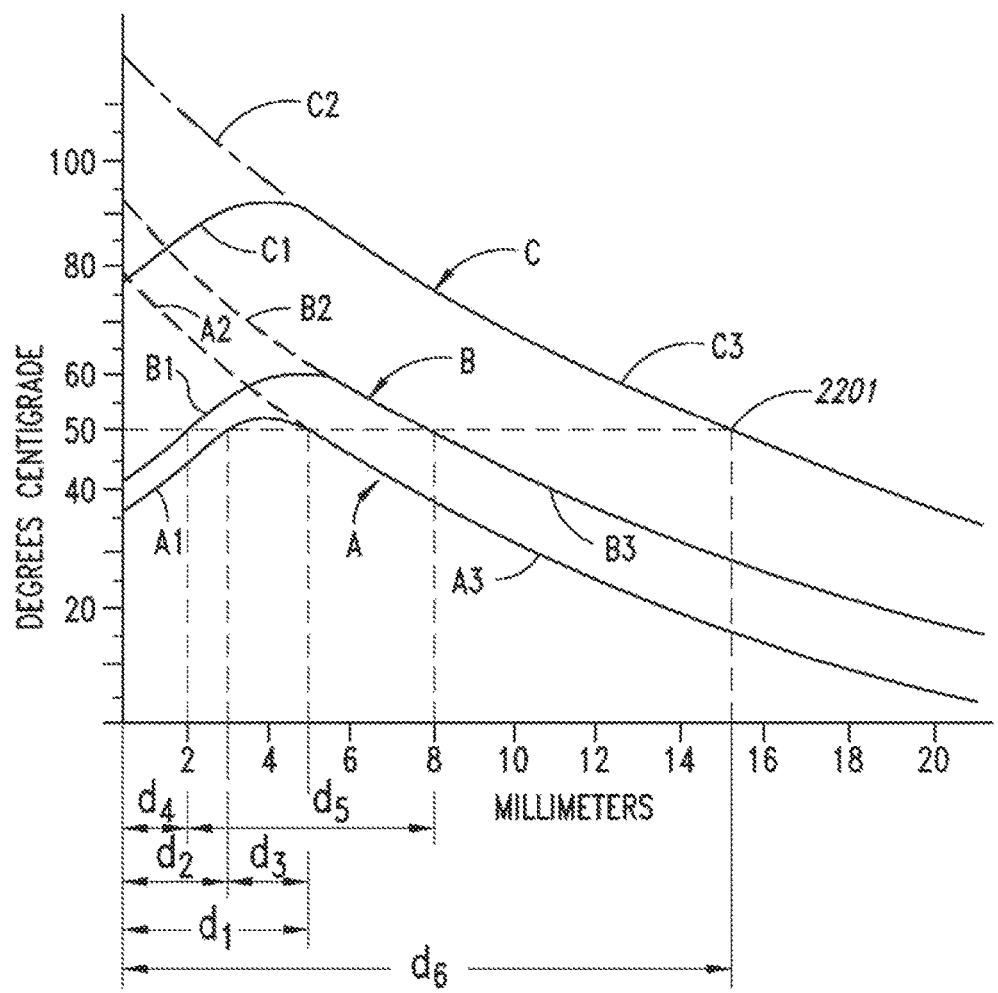
FIG. 16 is a graph of the depth of tissue versus temperature of the tissue.
Figure 17:
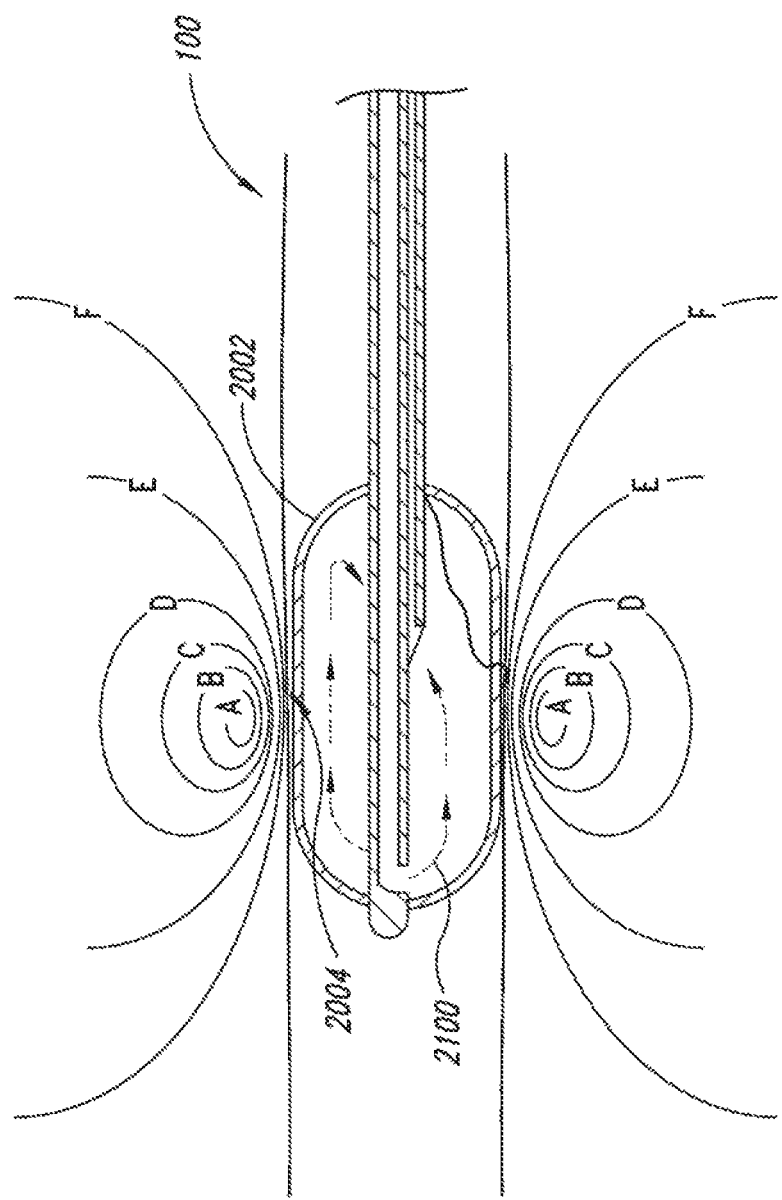
FIG. 17 is a side elevational view of the expandable assembly of FIG. 15A in an airway.

FIGS. 16 and 17 show the effect produced by superficial and deep heating by RF energy and superficial cooling by circulating coolant 2100 in the balloon 2002. FIG. 16 shows a cross-sectional temperature profile taken along a dashed line 2200 of FIG. 15B that is perpendicular to the long axis of the balloon 2002. FIGS. 16 and 17 are discussed in detail below.

FIG. 16 is a graph with a horizontal axis corresponding to the depth into the tissue of the airway wall from the point of contact or area of contact with the electrode 2004 in millimeters with a vertical axis corresponding to the temperature of the tissue in degrees Centigrade. The point "0" on the graph corresponds to the point or area of contact between the ablation electrode 2004 and the tissue of the airway wall. Three curves A, B, and C are shown in the graph and correspond to three different power levels of radio frequency energy being delivered into the tissue. The temperature on the graph is up to about 100° C. The temperature of about 100° C., or slightly less, has been shown because it is considered to be an upper limit for tissue temperature during RF ablation. At approximately 90° C., tissue fluids begin to boil and tissue coagulates and chars on the ablation electrode 2004, thereby greatly increasing its impedance and compromising its ability to transfer RF energy into the tissue of the airway wall. Thus, it may be desirable to have tissue temperatures remain below about 90° C. At about 50° C., a line 2201 represents the temperature above which tissue cell death occurs and below which tissues suffer no substantial long term effects (or any long term effects).

Curve A shown in FIG. 16 represents what occurs with and without cooling of the ablation electrode 2004 at a relatively low power level, for example, about 10 watts of RF energy. Curve A is divided into three segments A1, A2, and A3. The broken line segment A2 represents a continuation of the exponential curve A3 when no cooling applied. As can be seen by curve A, the temperature of the electrode-tissue interface without cooling reaches 80° C. and decreases exponentially as the distance into the tissue of the airway 100 increases. As shown, the curve A3 crosses the 50° C. tissue cell death boundary represented by the line 2201 at a depth of about 5 millimeters. Thus, without electrode cooling, the depth of cell death that would occur would be approximately 5 millimeters as represented by the distance d1. Further cell death would stop at this power level.

If active cooling is employed, the temperature drops to a much lower level, for example, about 35° C. as represented by the curve A1 at the electrode-tissue interface at 0 millimeters in distance. Since this temperature is below 50° C., cell death will not begin to occur until a distance of d2 at the point where the curve A2 crosses the cell death line at 50° C., for example, a depth of 3 millimeters from the surface. Cell death will occur at depths from 3 millimeters to 5 millimeters as represented by the distance d3. Such a cooled ablation procedure is advantageous because it permits cell death and tissue destruction to occur at a distance (or a range of distances) from the electrode-tissue interface without destroying the epithelium and the tissue immediately underlying the same. In some embodiments, the nerve tissues running along the outside of the airway can be ablated without damaging the epithelium or underlying structures, such as the stroma and smooth muscle cells.

The curve B represents what occurs with and without cooling of the electrode at a higher power level, for example, 20 watts of RF energy. Segment B2 of curve B represents a continuation of the exponential curve of the segment B3 without cooling. As can be seen, the temperature at the electrode-tissue interface approaches 100° C. which may be undesirable because that is a temperature at which boiling of tissue fluid and coagulation and charring of tissue at the tissue-electrode interface will occur, thus making significantly increasing the tissue impedance and compromising the ability to deliver additional RF energy into the airway wall. By providing active cooling, the curve B1 shows that the temperature at the electrode-tissue interface drops to approximately 40° C. and that cell death occurs at depths of two millimeters as represented by d4 to a depth of approximately 8 millimeters where the curve B3 crosses the 50° C. Thus, it can be seen that it is possible to provide a much deeper and larger region of cell death using the higher power level without reaching an undesirable high temperature (e.g., a temperature that would result in coagulation and charring of tissue at the electrode-tissue interface). The systems can be used to achieve cell death below the epithelia surface of the airway so that the surface need not be destroyed, thus facilitating early recovery by the patient from a treatment.

The curve C represents a still higher power level, for example, 40 watts of RF energy. The curve C includes segments C1, C2, and C3. The broken line segment C2 is a continuation of the exponential curve C3. Segment C2 shows that the temperature at the electrode-tissue interface far exceeds 100° C. and would be unsuitable without active cooling. With active cooling, the temperature at the electrode-tissue interface approaches 80° C. and gradually increases and approaches near 95° C. and then drops off exponentially to cross the 50° C. cell death line 2201 at a distance of about 15 millimeters from the electrode-tissue interface at the epithelial surface of the airway represented by the distance d6. Because the starting temperature is above the 50° C. cell death line 2201, tissue cell death will occur from the epithelial surface to a depth of about 15 millimeter to provide large and deep regions of tissue destruction.

FIG. 17 is a longitudinal cross-sectional view of the balloon expandable, fluid cooled electrode catheter 2000.

Lines of flow 2100 represent the movement of coolant through the expanded balloon 2002. Isothermal curves show the temperatures that are reached at the electrode 2004 on the outer surface of the balloon 2002 and at different depths into the airway wall 100 from the electrode-tissue interface when power is applied to the electrode 2004 and coolant (e.g., a room temperature saline solution) is delivered to the balloon 2002. By adjusting the rate of power delivery to the electrode 2004, the rate at which saline solution is passed into the balloon 2002, the temperature of the saline solution, and the size of the balloon 2002, the exact contour and temperature of the individual isotherms can be modified. For example, by selecting the proper temperature and flow rate of saline and the rate of power delivery to the electrode, it is possible to achieve temperatures in which isotherm A=60° C., B=55° C., C=50° C., D=45° C., E=40° C., and F=37° C. Further adjustments make it possible to achieve temperatures where isotherm A=50° C., B=47.5° C., C=45° C., D=42.5° C., E=40° C., and F=37° C. Only those areas contained within the 50° C. isotherm will be heated enough to induce cell death. Extrapolating into 3 dimensions the isotherms shown in FIG. 17, a circumferential band 2250 of tissue will potentially be heated above 50° C. sparing the tissue near the epithelial 110 of the airway 100. Different temperatures and isotherms can also be achieved.

Figure 18:
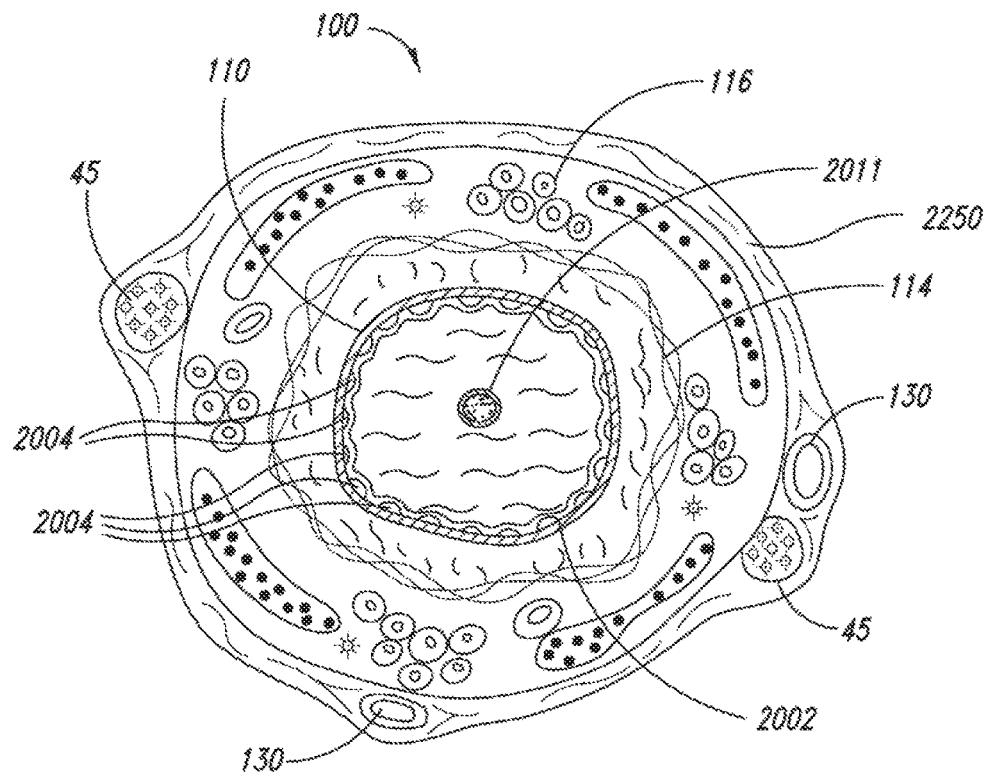
FIG. 18 is a cross-sectional view of the expandable assembly of FIG. 15A and an airway surrounding the expandable assembly.

FIG. 18 is a transverse cross-sectional view of a portion of the airway 100 and the balloon expandable, fluid cooled electrode catheter 2000 positioned in the airway 100. Because of the undulating shape of the expandable electrode 2004, the electrode appears as a multitude of ovals. The balloon 2002 is inflated to conform to both the expandable electrode 2004 and the epithelial surface of the airway 100. The electrode 2004 can be pressed against the airway 100. When RF energy is transmitted through the expanded electrode 2004 into the tissues of the airway 100 and the balloon 2002 is filled with flowing coolant 2100, the RF energy heats the superficial and deep tissue of the airway wall 100 and the connective tissue 124 while the coolant 2100 cools the superficial tissues of the airway wall 100. The net effect of this superficial and deep heating by RF energy and superficial cooling by the circulating coolant 2100 is the concentration of heat in the outer layers of the airway wall 100, such as the connective tissue 124. A band 2250 of tissue can be selectively heated above 50° C. For example, the temperature of the connective tissue 124 can be higher than the temperatures of the epithelium 110, stroma 112, and/or smooth muscle 114. Furthermore, one or more of the vessels of the bronchial artery branches 130 may be within the band 2250. The heat generated using the electrode 2004 can be controlled such that blood flowing through the bronchial artery branches 130 protects those branches 130 from thermal injury while nerve trunk tissue 45 is damaged, even if the nerve tissue is next to the artery branches.

The electrode catheter 2000 can treat tissue without forming an airway wall perforation at the treatment site to prevent or reduce the frequency of infections. It may also facilitate faster healing for the patient of tissue proximate the region of cell death. The catheter 2000 can produce relatively small regions of cell death. For example, a 2 to 3 millimeter band of tissue in the middle of the airway wall 100 or along the outer surface of the airway wall 100 can be destroyed. By the appropriate application of power and the appropriate removal of heat from the electrode, lesions can be created at any desired depth without damaging the inner surface of the airway.

Upon completion of the treatment process, coolant inflow into the balloon 2002 can be stopped. The balloon 2002 is deflated causing the expandable electrode 2004 to recoil away from the airway wall 100. When the balloon 2002 is completely deflated, the balloon expandable, fluid cooled electrode catheter 2000 may be repositioned for treating other locations in the lung or removed from the airway 100 entirely.

Figure 19A:
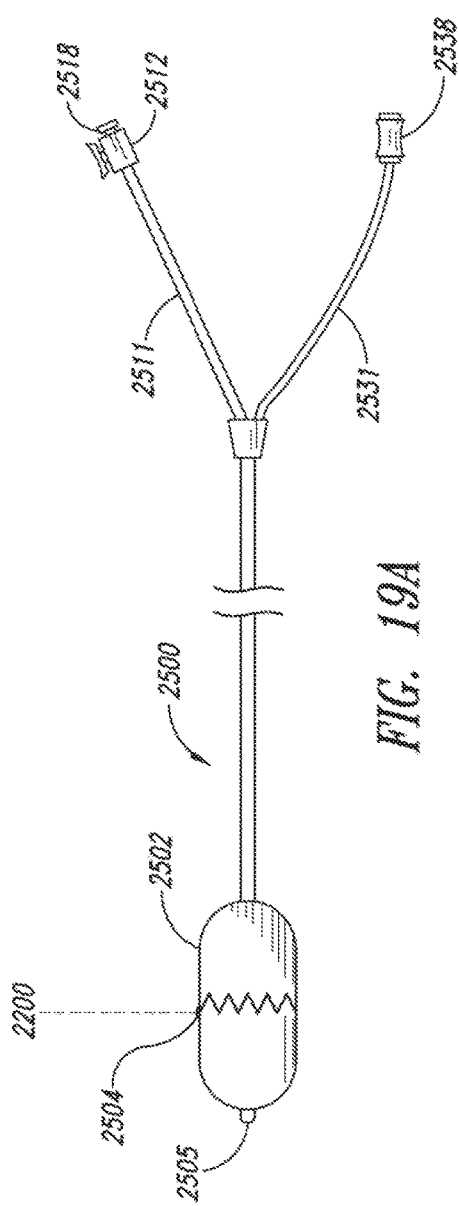
FIG. 19A is a side elevational view of a treatment system having an expandable assembly, in accordance with one embodiment.
Figure 19B:
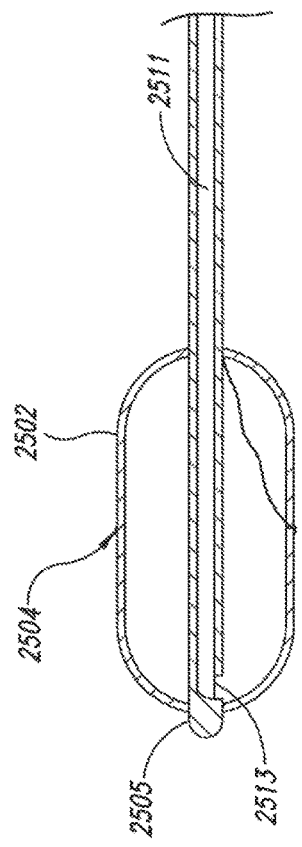
FIG. 19B is a cross-sectional view of the expandable assembly of FIG. 19A.

FIGS. 19A and 19B illustrate a treatment system that can be generally similar to the catheter 2000 discussed in connection with FIGS. 15A-18. A balloon expandable, fluid heat-sink electrode catheter 2500 has a single coolant line 2511 with associated inline valve 2512 and connector 2518 that provide for alternately inflow and outflow of heat-sink fluid into and out of a balloon 2502.

The balloon expandable, fluid heat-sink electrode catheter 2500 can be delivered into the airways of the lung with the balloon 2502 deflated and the electrode 2504 contracted. The catheter 2500 can be moved within the airways until the electrode 2504 is in a desired treatment location. Once in position, heat-sink fluid is passed through the line 2511 and into the balloon 2502, thereby inflating the balloon 2502 and expanding the electrode 2504. The fluid is passed into the balloon 2502 until the electrode 2504 is brought into contact with the airway wall 100.

The heat-sink fluid passed into the balloon 2502 of electrode catheter 2500 is generally static and acts as a heat-sink to stabilize the temperature of the electrode 2504 and the superficial tissues of the airway wall 100. The static heat sink provided by the fluid in the balloon 2502 can produce temperature profiles and isotherms similar to those shown in FIGS. 16 and 17. For example, the electrode catheter 2500 can cause a band of tissue cell death in the connective tissue of the airway while the epithelium, stroma, and/or smooth muscle are relatively undamaged. Thus, the nerve tissue can be damaged while other non-targeted tissues of the airway are protected.

Figure 21:
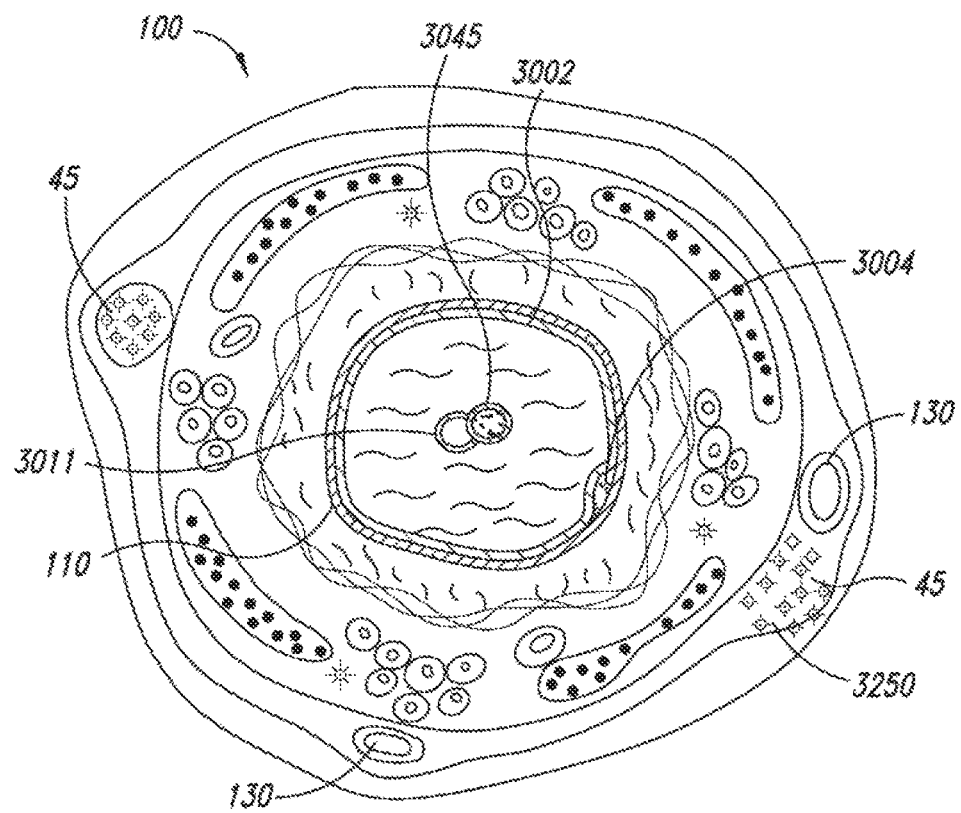
FIG. 21 is a cross-sectional view of the expandable assembly of FIG. 20A and an airway surrounding the expandable assembly.

FIGS. 20A-21 illustrate a treatment system that can be generally similar to the balloon expandable, fluid cooled electrode catheter 2000 shown in FIGS. 15A-18. FIG. 20A is a longitudinal side view of a radial ultrasound guided fluid cooled electrode catheter 3000. FIG. 20B is a partial longitudinal sectional view of the radial ultrasound guided fluid cooled electrode catheter 3000 taken through a balloon 3002 with lines of flow 3100 representing the movement of coolant through the expanded balloon 3002 and wavefronts 3047 of ultrasound imaging for guiding the ablation device.

The electrode catheter 3000 generally includes a distensible, thermally conductive balloon 3002, an electrode 3004, a conducting element 3031, an inflow line 3011, an outflow line 3021, and an ultrasound probe 3045. The expandable electrode 3004 is connected to a distal end of the conducting element 3031. A proximal end of the conducting element 3031 is connected to an electrical connector 3038 for transmission of energy (e.g., RF energy) to the electrode 3004. The proximal end of the coolant inflow line 3011 has an inline valve 3012. The proximal end of the coolant outflow line 3021 also has an outline valve 3022. The inflow valve 3012 can be connected to a coolant source by the connector 3018. The lumen of the inflow line 3011 and the lumen of the outflow line 3021 provide for fluid to flow from the fluid source to the inside of the balloon 3002 and for fluid flow through another connector 3028 to the coolant return, where the coolant may be re-cooled and re-circulated to the fluid supply.

The inflow line 3011 and outflow line 3021 have a suitable length to be passed into the lung and bronchial tree. For example, the catheter 3000 can have a length of approximately 80 cm. FIG. 20B shows a catheter 3000 is adapted to reduce, limit, or substantially prevent cross-flow, siphoning, or back-flow between the two lines within the balloon 3002. The inflow line 3011 enters the proximal end of the balloon 3002, extends through the length of the balloon 3002, reaches the distal end of the balloon 3002, and connects to the balloon 3002. The inflow line 3011 has an aperture 3013 near a tip 3005 that releases coolant into the balloon 3002. The fluid flows within the balloon 3002 and then is collected into the outflow line 3021 via an opening 3023. The opening 3023 is generally at the distal end of the outflow line 3021 and collects coolant from any direction.

The electrode 3004 is located on a surface of the balloon 3002 such that, when the balloon 3002 is inflated using fluid, the electrode 3004 is brought into contact with the airway wall 100. The electrical conducting element 3031 travels along side and parallel to the inflow line 3011, the outflow line 3021, and the ultrasound sheath 3041. The electrode 3004 can be connected through the electrical conducting element 3031 and the electrical connector 3038 to an RF generator. The other lead of the RF generator may be connected to an external electrode so that current flows between the expandable electrode 3004 and the external electrode.

The ultrasound probe 3045 may be an integral part of the ultrasound guided fluid cooled electrode catheter 3000 or it may be a separate, standard radial ultrasound probe, such as an Olympus UM-2R-3 or UM-3R-3 probe driven by a standard Olympus processor EU-M60, with the radial ultrasound guided fluid cooled electrode catheter 3000 configured to slip over the standard radial ultrasound probe.

The ultrasound system can include a broadband ultrasound transducer operating with a center frequency between about 7 MHz and about 50 MHz. If the ultrasound probe 3045 is an integral part of the electrode catheter 3000, the ultrasound probe 3045 may be contained within an acoustically matched ultrasound cover 3041 and connected to an ultrasound drive unit and processor by the ultrasound connector 3048. In operation, the ultrasound probe 3045 is rotated about its longitudinal axis within the ultrasound cover 3041 by the ultrasound drive unit and processor through the ultrasound connector 3048 allowing images (e.g., 360° radial images) to be taken. These images can be taken in a direction perpendicular to the long axis of the ultrasound probe 3045. The fluid in the balloon 3002 can acoustically couple the ultrasound probe 3045 to the airway wall.

The electrode catheter 3000 can be delivered into the airways of the lung with the balloon 3002 in a deflated state. The catheter 3000 is positioned within the airways near or at the desired treatment location. Once positioned, fluid flows through the inflow line 3011 and into the balloon 3002. The balloon 3002 inflates to bring the electrode 3004 into contact with the epithelial surface of the airway. Outflow of fluid through the outflow line 3021 can be regulated such that the balloon 3002 continues to inflate until the electrode 3004 is brought into contact with the airway wall 100.

The ultrasound drive unit and processor can be activated. The ultrasound probe 3045 can capture images. For example, the probe 3045, within the ultrasound cover 3041, can be rotated about its longitudinal axis to produce 360° radial images of the airway and vessels airway wall structures. The electrical connection wire 3031 can serve as a guide on the ultrasound images to the location of the electrode 3004. A section of the wire 3031 extending along (e.g., over the surface) of the balloon 3002 can be visible in the ultrasound images. The section of wire 3031 can therefore indicate the location of the electrode 3004. In some embodiments, the nerve trunks and bronchial blood can be identified in the ultrasound images and the ultrasound guided fluid cooled electrode catheter 3000 can be rotated until the electrode 3004 is brought into proximity with the first nerve trunk 45.

When the RF generator is activated, RF energy is transmitted by the generator through the electrical connector 3038, through the electrical connection wire 3031, through the expanded electrode 3004, and into the tissues of the airways. The RF energy heats the superficial and deep tissue of the airway wall 100 and the connective tissue 124 in the area immediately overlying the electrode 3004 and the coolant flowing 3100 through the balloon 3002 cools the superficial tissues of the airway wall 100. The net effect of this superficial and deep heating by RF energy and superficial cooling by the circulating coolant 3100 through the balloon 3002 is the concentration of heat in the outer layers of the airway wall 100 immediately overlying the electrode 3004. For example, the temperature of the connective tissue 124 in the area of a single nerve trunk 45 can be higher than the temperatures of the epithelium 110, stroma 112, and/or smooth muscle 114. By example, the temperature of the connective tissue can be sufficiently high to cause damage to the nerve tissue 45 while other non-targeted tissues of the airway 100 are kept at a lower temperature to prevent or limit damage to the non-targeted tissues. The treatment can be repeated in other areas as needed.

FIG. 21 is a transverse cross-sectional view of a portion of the airway 100 and the ultrasound guided fluid cooled electrode catheter 3000 positioned in the airway 100. The cross-section is taken through the electrode 3004 itself.

The balloon 3002 is conformable to both the electrode 3004 and the epithelial surface of the airway 100. When RF energy is transmitted through the electrode 3004 into the tissues of the airways and the balloon 3002 is filled with flowing coolant 3100, the RF energy heats the superficial and deep tissue of the airway wall 100 immediately overlying the electrode 3004. The coolant 3100 flows to control the temperature of the superficial tissues of the airway wall 100. The net effect is the concentration of heat in the outer layers of the airway wall 100 immediately over the electrode 3004 producing a single target volume 3250 of tissue heated above a treatment temperature (e.g., about 50° C.). For example, the temperature of the connective tissue 124 in the region of a single nerve trunk 45 in the region immediately over the electrode 3004 can be higher than the temperatures of the epithelium 110, stroma 112, and/or smooth muscle 114.

The vessels of the bronchial artery branches 130 may be within or near the volume of heating produced during application of RF energy. The heat generated by the electrode 3004 can be controlled such that blood flowing through the bronchial artery branches 130 protects those branches 130 from thermal injury while nerve tissue 45 is damaged, even if the nerve tissue is next to the artery branches.

The embodiments disclosed herein can be used in the respiratory system, digestive system, nervous system, vascular system, or other systems. For example, the elongate assemblies disclosed herein can be delivered through blood vessels to treat the vascular system. The treatment systems and its components disclosed herein can used as an adjunct during another medical procedure, such as minimally invasive procedures, open procedures, semi-open procedures, or other surgical procedures (e.g., lung volume reduction surgery) that preferably provide access to a desired target site. Various surgical procedures on the chest may provide access to lung tissue. Access techniques and procedures used to provide access to a target region can be performed by a surgeon and/or a robotic system. Those skilled in the art recognize that there are many different ways that a target region can be accessed.

The elongated assemblies disclosed herein can be used with guidewires, delivery sheaths, optical instruments, introducers, trocars, biopsy needles, or other suitable medical equipment. If the target treatment site is at a distant location in the patient (e.g., a treatment site near the lung root 24 of FIG. 1), a wide range of instruments and techniques can be used to access the site. The flexible elongated assemblies can be easily positioned within the patient using, for example, steerable delivery devices, such as endoscopes and bronchoscopes, as discussed above.

Semi-rigid or rigid elongated assemblies can be delivered using trocars, access ports, rigid delivery sheaths using semi-open procedures, open procedures, or other delivery tools/procedures that provide a somewhat straight delivery path. Advantageously, the semi-rigid or rigid elongated assemblies can be sufficiently rigid to access and treat remote tissue, such as the vagus nerve, nerve branches, nerve fibers, and/or nerve trunks along the airways, without delivering the elongated assemblies through the airways. The embodiments and techniques disclosed herein can be used with other procedures, such as bronchial thermoplasty.

The various embodiments described above can be combined to provide further embodiments. These and other changes can be made to the embodiments in light of the above-detailed description. The embodiments, features, systems, devices, materials, methods and techniques described herein may, in some embodiments, be similar to any one or more of the embodiments, features, systems, devices, materials, methods and techniques described in of U.S. Provisional Patent Application No. 61/052,082 filed May 9, 2008; U.S. Provisional Patent Application No. 61/106,490 filed Oct. 17, 2008; and U.S. Provisional Patent Application No. 61/155,449 filed Feb. 25, 2009. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned of U.S. Provisional Patent Application No. 61/052,082 filed May 9, 2008; U.S. Provisional Patent Application No. 61/106,490 filed Oct. 17, 2008; and U.S. Provisional Patent Application No. 61/155,449 filed Feb. 25, 2009. Each of these applications is hereby incorporated by reference in its entirety. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A system, comprising: a treatment controller; and a catheter comprising: an elongated body through which a coolant is capable of flowing; an electrode configured to output energy to ablate nerve tissue in an airway wall of an airway of a bronchial tree; and an expandable balloon having a collapsed state and an expanded state, wherein the expandable balloon in the expanded state is dimensioned to contact the airway wall of the bronchial tree, wherein the expandable balloon is coupled to the elongated body and configured to receive and contain the coolant such that the coolant cools the electrode and expandable balloon when the catheter is in contact with the airway wall to limit or prevent damage to tissue between the electrode and the nerve tissue, wherein the electrode is coupled to the expandable balloon such that the electrode is moved towards the airway wall as the expandable balloon moves from the collapsed state to the expanded state, wherein, when the expandable balloon is in the expanded state, portions of the expandable balloon are configured to contact an inner surface of the airway wall immediately adjacent to and on both proximal and distal sides of the electrode, wherein an axial dimension of the electrode is less than an axial dimension of each of the portions of the expandable balloon in contact with the inner surface of the airway wall, the axial dimension of the electrode and the axial dimension of each of the portions extending along a longitudinal axis of the airway; wherein the treatment controller is configured to control power to the electrode when coolant is circulated within the expandable balloon to output a sufficient amount of energy to damage the nerve tissue at a first location along the airway spaced radially outwardly from the inner surface of the airway wall at an electrode-tissue interface so as to attenuate transmission of signals to and/or from mucous producing cells at a second location along the airway so as to reduce a production of mucous from the mucous producing cells, while limiting damage to at least a portion of the tissue between the first location and the electrode-tissue interface and immediately adjacent the electrode-tissue interface.

2. The catheter of claim 1, wherein the electrode extends circumferentially about the expandable balloon when the expandable balloon is in the expanded state.

3. The catheter of claim 1, wherein the electrode is positioned outside of the expandable balloon such that the electrode is capable of outputting energy directly to the airway wall.

4. The catheter of claim 1, wherein the electrode is embedded in a wall of the expandable balloon.

5. The catheter of claim 1, wherein the electrode is coupled to an exterior surface of the expandable balloon or an interior surface of the expandable balloon.

6. The catheter of claim 1, further comprising a plurality of circumferentially spaced apart electrodes coupled to the expandable balloon and configured to output energy.

7. The catheter of claim 1, further comprising an ultrasound probe capable of outputting ultrasound energy through a wall of the expandable balloon for imaging.

8. The catheter of claim 1, wherein the electrode and the expandable balloon are configured to raise a temperature of the nerve tissue to cause cell death of the nerve tissue while maintaining a temperature of the tissue between the first location and the electrode-tissue interface and immediately adjacent the electrode-tissue interface below a temperature at which cell death occurs.

9. The catheter of claim 1, wherein the electrode and the expandable balloon are configured to cooperate to raise the temperature of tissue at a depth of 2 mm to 8 mm in the airway wall to cause cell death, while maintaining tissues at a depth less than 2 mm in the airway wall at a temperature below a temperature at which cell death occurs.

10. The system of claim 1, further comprising: a coolant source coupled to the catheter, and a radiofrequency generator coupled to the catheter and the controller; wherein the coolant source is configured to deliver coolant to the expandable balloon and the radiofrequency generator is configured to deliver energy to the electrode to concentrate heating in outer layers of the airway wall.

11. The system of claim 10, wherein the coolant source is configured to output a low temperature coolant that absorbs thermal energy to cool tissue contacting the expandable balloon.

12. The system of claim 10, further comprising:
a bronchoscope having a delivery lumen for receiving the catheter.

13. A method of treating an airway condition caused by excessive intraluminal mucus, mucous glands hypertrophy, or both, the method comprising:
using the system of claim 1, causing damage to nerve tissue at a first location along the airway so as to attenuate transmission of signals to and/or from mucous producing cells at a second location along the airway so as to reduce a production of mucous from the mucous producing cells.

14. The method of claim 13, wherein causing damage to nerve tissue comprises damaging efferent nerve tissue to inhibit signals from being transmitted from the brain to mucous producing cells of the airway.

15. The method of claim 13, wherein causing damage to nerve tissue disrupts a baseline level of mucous secretion.

16. The method of claim 13, wherein causing damage to nerve tissue attenuates transmission of signals traveling along vagus nerves that cause mucus production.

17. The method of claim 16, wherein attenuation of the transmission of signals comprises decreasing signal amplitude or weakening transmission of signals.

18. The method of claim 13, wherein attenuation of the transmission of signals comprises hindering, limiting, blocking, and/or interrupting transmission of signals.

19. The method of claim 13, wherein the method decreases a sufficient amount of mucus production to cause substantial decrease in coughing and/or airflow resistance.

20. The method of claim 13, wherein the method further comprises, after causing damage to nerve tissue:
providing a questionnaire or test to assess a subject's response to treatment by assessing a subject's quality of life and comparing the assessment to an assessment of the subject's quality of life before damaging the nerve tissue.

21. The method of claim 13, wherein causing damage to nerve tissue comprises: outputting energy from the electrode of the catheter positioned in the airway to heat and ablate the nerve tissue along the airway wall at the first location; and cooling a portion of the expandable balloon to cool an inner portion of the airway wall while outputting the energy to inhibit damage to the inner portion of the wall while the nerve tissue is ablated.

22. The method of claim 13, wherein causing damage to nerve tissue comprises: delivering energy from the electrode of the catheter positioned in the airway to destroy the nerve tissue along the wall of the airway while avoiding injury to airway tissue distal the damaged nerve tissue.

23. The method of claim 13, wherein the nerve tissue is positioned between a trachea and a lung of a subject.

24. The method of claim 13, wherein causing damage to nerve tissue includes ablating nerve tissue of a nerve trunk along a right main bronchus, a left main bronchus, or both.

* * * * *

UNITED STATES PATENT AND TRADEMARK OFFICE
CERTIFICATE OF CORRECTION

PATENT NO. : 10,149,714 B2
APPLICATION NO. : 15/427685
DATED : December 11, 2018
INVENTOR(S) : Mayse et al.

Page 1 of 2

It is certified that error appears in the above-identified patent and that said Letters Patent is hereby corrected as shown below:

In the Claims

Column 31, Line 57, Claim 1:
Indent paragraphs:
1. A system, comprising:
  a treatment controller; and
  a catheter comprising:
    an elongated body through which a coolant is capable of flowing;
    an electrode configured to output energy to ablate nerve tissue in an airway wall of an airway of a bronchial tree; and
    an expandable balloon having a collapsed state and an expanded state,
    wherein the expandable balloon in the expanded state is dimensioned to contact the airway wall of the bronchial tree,
    wherein the expandable balloon is coupled to the elongated body and configured to receive and contain the coolant such that the coolant cools the electrode and expandable balloon when the catheter is in contact with the airway wall to limit or prevent damage to tissue between the electrode and the nerve tissue,
    wherein the electrode is coupled to the expandable balloon such that the electrode is moved towards the airway wall as the expandable balloon moves from the collapsed state to the expanded state,
    wherein, when the expandable balloon is in the expanded state, portions of the expandable balloon are configured to contact an inner surface of the airway wall immediately adjacent to and on both proximal and distal sides of the electrode, wherein an axial dimension of the electrode is less than an axial dimension of each of the portions of the expandable balloon in contact with the inner surface of the airway wall, the axial dimension of the electrode and the axial dimension of each of the portions extending along a longitudinal axis of the airway;
    wherein the treatment controller is configured to control power to the electrode when coolant is circulated within the expandable balloon to output a sufficient amount of energy to damage the nerve tissue at a first location along the Signed and Sealed this
Eighth Day of October, 2019

Andrei Iancu
*Director of the United States Patent and Trademark Office* airway spaced radially outwardly from the inner surface of the airway wall at an electrode-tissue interface so as to attenuate transmission of signals to and/or from mucous producing cells at a second location along the airway so as to reduce a production of mucous from the mucous producing cells, while limiting damage to at least a portion of the tissue between the first location and the electrode-tissue interface and immediately adjacent the electrode-tissue interface.

<u>Column 32, Line 61, Claim 10</u>:
Indent paragraphs:
10. The system of claim 1, further comprising:
    a coolant source coupled to the catheter, and
    a radiofrequency generator coupled to the catheter and the controller;
    wherein the coolant source is configured to deliver coolant to the expandable balloon and the radiofrequency generator is configured to deliver energy to the electrode to concentrate heating in outer layers of the airway wall.